(12) United States Patent
Caplan et al.

(10) Patent No.: US 12,396,777 B2
(45) Date of Patent: Aug. 26, 2025

(54) ABLATION SYSTEMS, DEVICES AND METHODS FOR THE TREATMENT OF TISSUE

(71) Applicant: Fractyl Health, Inc., Burlington, MA (US)

(72) Inventors: Jay Caplan, Boston, MA (US); Philip S. Levin, Storrs, CT (US); Andrew Coats, Somerville, MA (US); Harith Rajagopalan, Wellesley Hills, MA (US); Mark A. Manasas, Lexington, MA (US); J. Christopher Flaherty, Nottingham, NH (US)

(73) Assignee: Fractyl Health, Inc., Burlington, MA (US)

( * ) Notice: Subject to any disclaimer, the term of this patent is extended or adjusted under 35 U.S.C. 154(b) by 0 days.

(21) Appl. No.: 19/007,206

(22) Filed: Dec. 31, 2024

(65) Prior Publication Data

US 2025/0127551 A1    Apr. 24, 2025

Related U.S. Application Data

(63) Continuation of application No. 18/786,113, filed on Jul. 26, 2024, which is a continuation of application
(Continued)

(51) Int. Cl.
*A61B 18/04*    (2006.01)
*A61B 18/06*    (2006.01)
(Continued)

(52) U.S. Cl.
CPC .............. *A61B 18/04* (2013.01); *A61B 18/06* (2013.01); *A61M 25/1002* (2013.01);
(Continued)

(58) Field of Classification Search
CPC ............ A61B 18/04; A61B 2018/0017; A61B 2018/00011; A61B 2018/00494;
(Continued)

(56) References Cited

U.S. PATENT DOCUMENTS 5,084,044 A    1/1992    Quint
5,190,540 A    3/1993    Lee
(Continued)

FOREIGN PATENT DOCUMENTS

CA    2666661 C    1/2015
CN    1771888 A    5/2006
(Continued)

OTHER PUBLICATIONS

Co-pending U.S. Appl. No. 17/096,855, inventors Rajagopalan; Harith et al., filed Nov. 12, 2020.
(Continued)

*Primary Examiner* — Jenna Zhang
(74) *Attorney, Agent, or Firm* — Wolf, Greenfield & Sacks, P.C.

(57) ABSTRACT

A device for ablating target tissue of a patient with an ablative fluid is provided. An elongate shaft includes a proximal portion and a distal portion, and at least one fluid delivery element is attached to the distal portion. The device can be configured to ablate the duodenal mucosa of a patient while avoiding damage to the duodenal adventitial tissue. Systems and methods of treating target tissue are also provided.

20 Claims, 11 Drawing Sheets

Related U.S. Application Data

No. 17/192,671, filed on Mar. 4, 2021, now Pat. No. 12,089,887, which is a continuation of application No. 14/609,334, filed on Jan. 29, 2015, now Pat. No. 10,973,561, which is a continuation of application No. PCT/US2013/054219, filed on Aug. 8, 2013.

(60) Provisional application No. 61/681,502, filed on Aug. 9, 2012.

(51) Int. Cl.
| | | |
|---|---|---|
| *A61M 25/10* | (2013.01) | |
| *A61B 17/00* | (2006.01) | |
| *A61B 18/00* | (2006.01) | |
| *A61B 18/02* | (2006.01) | |
| *A61B 18/14* | (2006.01) | |
| *A61B 18/24* | (2006.01) | |
| *A61N 7/02* | (2006.01) | |

(52) U.S. Cl.
CPC .......... *A61M 25/1011* (2013.01); *A61B 2017/00269* (2013.01); *A61B 2018/00011* (2013.01); *A61B 2018/00017* (2013.01); *A61B 2018/0022* (2013.01); *A61B 2018/00494* (2013.01); *A61B 2018/00577* (2013.01); *A61B 2018/00994* (2013.01); *A61B 2018/0212* (2013.01); *A61B 2018/046* (2013.01); *A61B 2018/048* (2013.01); *A61B 18/1492* (2013.01); *A61B 18/24* (2013.01); *A61M 2025/1015* (2013.01); *A61M 2025/105* (2013.01); *A61N 7/022* (2013.01)

(58) Field of Classification Search
CPC .... A61B 2018/00577; A61B 2018/046; A61B 2018/048; A61B 2017/00269
See application file for complete search history.

(56) References Cited

U.S. PATENT DOCUMENTS

| | | | |
|---|---|---|---|
| 5,423,754 A | 6/1995 | Cornelius et al. | |
| 5,471,982 A | 12/1995 | Edwards et al. | |
| 5,496,311 A | 3/1996 | Abele et al. | |
| 5,515,100 A | 5/1996 | Nogo | |
| 5,542,928 A | 8/1996 | Evans et al. | |
| 5,549,559 A | 8/1996 | Eshel | |
| 5,575,772 A | 11/1996 | Lennox | |
| 5,704,934 A | 1/1998 | Neuwirth et al. | |
| 5,730,719 A | 3/1998 | Edwards | |
| 5,800,484 A | 9/1998 | Gough et al. | |
| 5,827,269 A | 10/1998 | Saadat | |
| 5,859,037 A | 1/1999 | Whitcomb | |
| 5,869,037 A | 2/1999 | Crystal et al. | |
| 5,871,525 A | 2/1999 | Edwards et al. | |
| 5,879,347 A | 3/1999 | Saadat | |
| 5,957,962 A | 9/1999 | Wallsten et al. | |
| 5,964,753 A | 10/1999 | Edwards | |
| 6,009,877 A | 1/2000 | Edwards | |
| 6,053,937 A | 4/2000 | Edwards et al. | |
| 6,056,744 A | 5/2000 | Edwards | |
| 6,066,132 A | 5/2000 | Chen et al. | |
| 6,077,257 A | 6/2000 | Edwards et al. | |
| 6,112,123 A | 8/2000 | Kelleher et al. | |
| 6,293,909 B1 | 9/2001 | Chu et al. | |
| 6,325,777 B1 | 12/2001 | Zadno-Azizi et al. | |
| 6,325,798 B1 | 12/2001 | Edwards et al. | |
| 6,338,726 B1 | 1/2002 | Edwards et al. | |
| 6,358,245 B1 | 3/2002 | Edwards et al. | |
| 6,402,744 B2 | 6/2002 | Edwards et al. | |
| 6,405,732 B1 | 6/2002 | Edwards et al. | |
| 6,409,723 B1 | 6/2002 | Edwards | |
| 6,425,887 B1 | 7/2002 | McGuckin et al. | |
| 6,443,947 B1 | 9/2002 | Marko et al. | |
| 6,544,226 B1 | 4/2003 | Gaiser et al. | |
| 6,673,070 B2 | 1/2004 | Edwards et al. | |
| 6,712,814 B2 | 3/2004 | Edwards et al. | |
| 6,802,841 B2 | 10/2004 | Utley et al. | |
| 6,905,496 B1 | 6/2005 | Ellman et al. | |
| 6,962,587 B2 | 11/2005 | Johnson et al. | |
| 6,974,456 B2 | 12/2005 | Edwards et al. | |
| 7,077,841 B2 | 7/2006 | Gaiser et al. | |
| 7,111,627 B2 | 9/2006 | Stack et al. | |
| 7,122,031 B2 | 10/2006 | Edwards et al. | |
| 7,125,407 B2 | 10/2006 | Edwards et al. | |
| 7,156,860 B2 | 1/2007 | Wallsten | |
| 7,165,551 B2 | 1/2007 | Edwards et al. | |
| 7,241,295 B2 | 7/2007 | Maguire | |
| 7,326,207 B2 | 2/2008 | Edwards | |
| 7,371,215 B2 | 5/2008 | Colliou et al. | |
| 7,387,626 B2 | 6/2008 | Edwards et al. | |
| 7,422,587 B2 | 9/2008 | Bek et al. | |
| 7,507,234 B2 | 3/2009 | Utley et al. | |
| 7,507,238 B2 | 3/2009 | Edwards et al. | |
| 7,530,979 B2 | 5/2009 | Ganz et al. | |
| 7,556,628 B2 | 7/2009 | Utley et al. | |
| 7,585,296 B2 | 9/2009 | Edwards et al. | |
| 7,632,268 B2 | 12/2009 | Edwards et al. | |
| 7,632,291 B2 | 12/2009 | Stephens et al. | |
| 7,648,500 B2 | 1/2010 | Edwards et al. | |
| 7,758,623 B2 | 7/2010 | Dzeng et al. | |
| 7,762,977 B2 | 7/2010 | Porter et al. | |
| 7,947,038 B2 | 5/2011 | Edwards | |
| 7,959,627 B2 | 6/2011 | Utley et al. | |
| 7,993,336 B2 | 8/2011 | Jackson et al. | |
| 7,997,278 B2 | 8/2011 | Utley et al. | |
| 8,012,149 B2 | 9/2011 | Jackson et al. | |
| 8,066,689 B2 | 11/2011 | Mitelberg et al. | |
| 8,152,803 B2 | 4/2012 | Edwards et al. | |
| 8,177,853 B2 | 5/2012 | Stack et al. | |
| 8,192,426 B2 | 6/2012 | Stern et al. | |
| 8,251,992 B2 | 8/2012 | Utley et al. | |
| 8,273,012 B2 | 9/2012 | Wallace et al. | |
| 8,323,229 B2 | 12/2012 | Shin et al. | |
| 8,364,237 B2 | 1/2013 | Stone et al. | |
| 8,377,055 B2 | 2/2013 | Jackson et al. | |
| 8,486,005 B2 | 7/2013 | Yodfat et al. | |
| 8,641,711 B2 | 2/2014 | Kelly et al. | |
| 8,740,894 B2 | 6/2014 | Edwards | |
| 8,790,705 B2 | 7/2014 | Geigle et al. | |
| 9,364,283 B2 | 6/2016 | Utley et al. | |
| 9,555,020 B2 | 1/2017 | Pasricha et al. | |
| 9,615,880 B2 | 4/2017 | Gittard et al. | |
| 9,757,535 B2 | 9/2017 | Rajagopalan et al. | |
| 9,844,641 B2 | 12/2017 | Rajagopalan et al. | |
| 10,232,143 B2 | 3/2019 | Rajagopalan et al. | |
| 10,299,857 B2 | 5/2019 | Rajagopalan et al. | |
| 10,349,998 B2 | 7/2019 | Levin et al. | |
| 10,610,663 B2 | 4/2020 | Rajagopalan et al. | |
| 10,765,474 B2 | 9/2020 | Kadamus et al. | |
| 10,864,352 B2 | 12/2020 | Rajagopalan et al. | |
| 10,869,718 B2 | 12/2020 | Rajagopalan et al. | |
| 10,973,561 B2 | 4/2021 | Caplan et al. | |
| 10,980,590 B2 | 4/2021 | Rajagopalan et al. | |
| 10,987,149 B2 | 4/2021 | Rajagopalan et al. | |
| 12,089,887 B2 | 9/2024 | Caplan et al. | |
| 2002/0013581 A1 | 1/2002 | Edwards et al. | |
| 2002/0077594 A1 | 6/2002 | Chien et al. | |
| 2002/0115992 A1 | 8/2002 | Utley et al. | |
| 2002/0192162 A1 | 12/2002 | Green | |
| 2003/0040804 A1* | 2/2003 | Stack | A61F 5/0069 623/902 |
| 2003/0093072 A1 | 5/2003 | Friedman | |
| 2003/0153905 A1 | 8/2003 | Edwards et al. | |
| 2003/0233065 A1 | 12/2003 | Steward et al. | |
| 2004/0082859 A1* | 4/2004 | Schaer | A61B 18/1492 600/459 |
| 2004/0087936 A1 | 5/2004 | Stern et al. | |
| 2004/0133256 A1 | 7/2004 | Callister | |
| 2004/0148034 A1 | 7/2004 | Kagan et al. | |
| 2004/0204768 A1 | 10/2004 | Geitz | |
| 2004/0215180 A1 | 10/2004 | Starkebaum et al. | |

(56) References Cited

U.S. PATENT DOCUMENTS

| | | |
|---|---|---|
| 2004/0215296 A1 | 10/2004 | Ganz et al. |
| 2004/0220559 A1 | 11/2004 | Kramer et al. |
| 2005/0096638 A1 | 5/2005 | Starkebaum et al. |
| 2005/0154386 A1 | 7/2005 | West et al. |
| 2005/0165437 A1 | 7/2005 | Takimoto |
| 2005/0171524 A1 | 8/2005 | Stern et al. |
| 2005/0192652 A1 | 9/2005 | Cioanta et al. |
| 2005/0203489 A1 | 9/2005 | Saadat et al. |
| 2005/0222558 A1 | 10/2005 | Baxter et al. |
| 2005/0245943 A1 | 11/2005 | Zvuloni et al. |
| 2005/0251116 A1 | 11/2005 | Steinke et al. |
| 2005/0273090 A1 | 12/2005 | Nieman et al. |
| 2006/0070631 A1 | 4/2006 | Scopton et al. |
| 2006/0118127 A1 | 6/2006 | Chinn |
| 2006/0135963 A1 | 6/2006 | Kick et al. |
| 2006/0155261 A1 | 7/2006 | Bek et al. |
| 2006/0205992 A1 | 9/2006 | Lubock et al. |
| 2006/0247683 A1 | 11/2006 | Danek et al. |
| 2006/0259030 A1 | 11/2006 | Utley et al. |
| 2006/0293742 A1 | 12/2006 | Dann et al. |
| 2007/0016262 A1 | 1/2007 | Gross et al. |
| 2007/0032788 A1 | 2/2007 | Edwards et al. |
| 2007/0100355 A1 | 5/2007 | Bonde et al. |
| 2008/0045785 A1 | 2/2008 | Oyatsu |
| 2008/0107744 A1 | 5/2008 | Chu |
| 2008/0119788 A1 | 5/2008 | Winter |
| 2008/0125760 A1 | 5/2008 | Gilboa |
| 2008/0125803 A1 | 5/2008 | Sadamasa et al. |
| 2008/0147056 A1 | 6/2008 | van der Weide et al. |
| 2008/0207994 A1 | 8/2008 | Gonon |
| 2008/0243112 A1 | 10/2008 | De Neve |
| 2008/0275445 A1* | 11/2008 | Kelly ............... A61B 18/1492 606/45 |
| 2008/0319504 A1 | 12/2008 | Loushin et al. |
| 2009/0012469 A1* | 1/2009 | Nita ............... A61B 17/22012 604/113 |
| 2009/0012512 A1 | 1/2009 | Utley et al. |
| 2009/0012518 A1 | 1/2009 | Utley et al. |
| 2009/0018533 A1 | 1/2009 | Perkins et al. |
| 2009/0018604 A1 | 1/2009 | Mitelberg et al. |
| 2009/0048593 A1 | 2/2009 | Ganz et al. |
| 2009/0069805 A1 | 3/2009 | Fischer et al. |
| 2009/0270851 A1 | 10/2009 | Babkin et al. |
| 2010/0022891 A1 | 1/2010 | Zuluaga et al. |
| 2010/0030190 A1 | 2/2010 | Singh |
| 2010/0114087 A1 | 5/2010 | Edwards et al. |
| 2010/0114325 A1 | 5/2010 | Yang et al. |
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1 | 8/2010 | Gostout et al. |
| 2010/0234840 A1 | 9/2010 | Jackson et al. |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0184401 A1 | 7/2011 | Iwata et al. |
| 2011/0319809 A1 | 12/2011 | Smith |
| 2012/0004654 A1 | 1/2012 | Jackson et al. |
| 2012/0016364 A1 | 1/2012 | Mayse et al. |
| 2012/0059364 A1 | 3/2012 | Baust et al. |
| 2012/0197245 A1 | 8/2012 | Burnett et al. |
| 2012/0271277 A1 | 10/2012 | Fischell et al. |
| 2012/0271301 A1 | 10/2012 | Fischell et al. |
| 2012/0289952 A1 | 11/2012 | Utley et al. |
| 2013/0071466 A1 | 3/2013 | Chancellor et al. |
| 2013/0178910 A1 | 7/2013 | Azamian et al. |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 | 6/2014 | Goldsmith |
| 2014/0187619 A1 | 7/2014 | Pasricha et al. |
| 2014/0255458 A1 | 9/2014 | Li et al. |
| 2014/0324037 A1 | 10/2014 | Hoey et al. |
| 2014/0371736 A1 | 12/2014 | Levin et al. |
| 2015/0045825 A1 | 2/2015 | Caplan et al. |
| 2015/0141987 A1 | 5/2015 | Caplan et al. |
| 2015/0148738 A1 | 5/2015 | Caplan et al. |
| 2015/0359594 A1 | 12/2015 | Ben-Oren et al. |
| 2016/0008050 A1 | 1/2016 | Rajagopalan et al. |
| 2016/0310200 A1 | 10/2016 | Wang |
| 2016/0354144 A1 | 12/2016 | Caplan et al. |
| 2017/0007324 A1 | 1/2017 | Kadamus et al. |
| 2017/0014596 A1 | 1/2017 | Rajagopalan et al. |
| 2017/0191035 A1 | 7/2017 | Sia et al. |
| 2017/0333122 A1 | 11/2017 | Rajagopalan et al. |
| 2018/0193590 A1 | 7/2018 | Rajagopalan et al. |
| 2018/0221622 A1 | 8/2018 | Rajagopalan et al. |
| 2020/0001047 A1 | 1/2020 | Rajagopalan et al. |
| 2020/0060758 A1 | 2/2020 | Rajagopalan et al. |
| 2020/0060942 A1 | 2/2020 | Rajagopalan et al. |
| 2020/0138505 A1 | 5/2020 | Levin et al. |
| 2020/0155217 A1 | 5/2020 | Morneau et al. |
| 2020/0261144 A1 | 8/2020 | Caplan et al. |
| 2020/0305972 A1 | 10/2020 | Kadamus et al. |
| 2020/0405388 A1 | 12/2020 | Rajagopalan et al. |
| 2021/0008336 A1 | 1/2021 | Rajagopalan et al. |
| 2021/0085390 A1 | 3/2021 | Kadamus et al. |
| 2021/0137995 A1 | 5/2021 | Rajagopalan et al. |

FOREIGN PATENT DOCUMENTS

| | | |
|---|---|---|
| CN | 101212932 A | 7/2008 |
| EP | 1698296 A1 | 9/2006 |
| EP | 1886634 A1 | 2/2008 |
| EP | 3071286 A1 | 9/2016 |
| JP | 2002503512 A | 2/2002 |
| JP | 2003520068 A | 7/2003 |
| JP | 2004500184 A | 1/2004 |
| JP | 2004180934 A | 7/2004 |
| JP | 2006509536 A | 3/2006 |
| JP | 2006136726 A | 6/2006 |
| JP | 2007502690 A | 2/2007 |
| JP | 2014503256 A | 2/2008 |
| JP | 2008515464 A | 5/2008 |
| JP | 2010142661 A | 7/2010 |
| JP | 2010533036 A | 10/2010 |
| JP | 2011517599 A | 6/2011 |
| JP | 2013543423 A | 12/2013 |
| KR | 20080013945 A | 2/2008 |
| WO | WO 1994/18896 A1 | 9/1994 |
| WO | WO 1999/12489 A2 | 3/1999 |
| WO | WO 02/007628 A2 | 1/2002 |
| WO | WO 02/058577 A1 | 8/2002 |
| WO | WO 02/096327 A2 | 12/2002 |
| WO | WO 02/102453 A2 | 12/2002 |
| WO | WO 03/033045 A2 | 4/2003 |
| WO | WO 03/092609 A2 | 11/2003 |
| WO | WO 2004/064600 A2 | 8/2004 |
| WO | WO 2006/020370 A2 | 2/2006 |
| WO | WO 2007/044244 A2 | 4/2007 |
| WO | WO 2007/067919 A2 | 6/2007 |
| WO | WO 2008/002654 A2 | 1/2008 |
| WO | WO 2010/042461 A1 | 4/2010 |
| WO | WO 2010/125570 A1 | 11/2010 |
| WO | WO 2011/060301 A1 | 5/2011 |
| WO | WO 2012/009486 A2 | 1/2012 |
| WO | WO 2012/099974 A2 | 7/2012 |
| WO | WO 2013/130655 A1 | 9/2013 |
| WO | WO 2013/134541 A2 | 9/2013 |
| WO | WO 2013/159066 A1 | 10/2013 |
| WO | WO 2014/022436 A1 | 2/2014 |
| WO | WO 2014/026055 A1 | 2/2014 |
| WO | WO 2014/055997 A1 | 4/2014 |
| WO | WO 2014/070136 A1 | 5/2014 |
| WO | WO 2015/038973 A1 | 3/2015 |
| WO | WO 2015/077571 A1 | 5/2015 |
| WO | WO 2015/148541 A1 | 10/2015 |

(56) References Cited

FOREIGN PATENT DOCUMENTS

| WO | WO 2016/011269 A1 | 1/2016 |
|----|-------------------|--------|
| WO | WO 2017/004432 A1 | 1/2017 |
| WO | WO 2018/089773 A1 | 5/2018 |
| WO | WO 2019/018362 A1 | 1/2019 |
| WO | WO 2019/136240 A1 | 7/2019 |

OTHER PUBLICATIONS

Co-pending U.S. Appl. No. 202017095108, inventors Rajagopalan; Harith et al., filed Nov. 11, 2020.
U.S. Appl. No. 14/609,332, filed Jan. 29, 2015.
U.S. Appl. No. 61/603,475, filed Feb. 27, 2012.
U.S. Appl. No. 61/635,810, filed Apr. 19, 2012.
U.S. Appl. No. 61/681,502, filed Aug. 9, 2012.
European Search Report and Search Opinion dated Aug. 4, 2015 for EP Application No. 13755156.0.
European Search Report and Search Opinion dated Nov. 25, 2015 for EP Application No. 13777572.2.
European Search Report and Search Opinion dated Mar. 8, 2016 for EP Application No. 13825257.2.
European Search Report and Search Opinion dated Mar. 17, 2016 for EP Application No. 13827149.9.
The Extended European Search Report dated Nov. 22, 2016 for EP Application No. EP12736438.8.
European Search Report with Written Opinion dated Dec. 2, 2016 for EP Application No. 14807116.
The Extended European Search Report dated Apr. 25, 2017 for EP Application No. EP14844285.8.
European Search Report and Search Opinion dated Aug. 7, 2017 for European Patent Application No. EP14864511.2.
European Search Report and Search Opinion dated Aug. 7, 2017 for European Patent Application No. EP15768945.6.
European Search Report with Written Opinion dated Feb. 1, 2018 for EP Application No. 15822378.
The Extended European Search Report dated Aug. 17, 2020 for EP Application No. EP20159816.6.
The Extended European Search Report dated Aug. 20, 2020 for EP Application No. EP20150391.9.
International Search Report and Written Opinion dated Jul. 13, 2012 for PCT Application No. US2012/021739.
International Search Report and Written Opinion dated Jun. 21, 2013 for PCT Application No. US2013/028082.
International Search Report and Written Opinion dated Aug. 8, 2013 for PCT Application No. US2013/037485.
International Search Report and Written Opinion dated Nov. 8, 2013 for PCT Application No. US2013/052786.
International Search Report and Written Opinion dated Nov. 11, 2013 for PCT Application No. US2013/054219.
International Search Report and Written Opinion dated Dec. 30, 2013 for PCT Application No. US2013/063753.
International Search Report and Written Opinion dated Dec. 3, 2014 for PCT Application No. US2014/040957.
International Search Report and Written Opinion dated Dec. 24, 2014 for PCT Application No. US2014/055514.
International Search Report and Written Opinion dated Feb. 20, 2015 for PCT/US14/66829.
International Search Report and Written Opinion dated Feb. 20, 2015 for PCT Application No. US2014/711601.
International Search Report and Written Opinion dated Jun. 26, 2015 for PCT Application No. US2015/022293.
International Search Report and Written Opinion dated Oct. 23, 2015 for PCT/US2015/040775.
International Search Report and Written Opinion dated Sep. 22, 2016 for International PCT Patent Application No. PCT/US2016/040512.
International Search Report and Written Opinion dated Jan. 9, 2018 for PCT/US2017/061074.
International Search Report and Written Opinion dated Sep. 14, 2018 for PCT/US2018/042438.
International Search Report and Written Opinion dated Apr. 15, 2019 for PCT/US2019/012338.
Final Office action dated Mar. 22, 2019 for U.S. Appl. No. 14/917,243.
Final Office action dated Apr. 5, 2019 for U.S. Appl. No. 14/609,334.
Final Office action dated Jun. 17, 19 for U.S. Appl. No. 14/609,332.
Final Office action dated Jul. 10, 2019 for U.S. Appl. No. 15/274,948.
Office Action date Jul. 11, 2018 for U.S. Appl. No. 14/917,243.
Office Action date Aug. 9, 2018 for U.S. Appl. No. 14/673,565.
Office action dated Jan. 8, 2018 for U.S. Appl. No. 14/609,334.
Office Action dated Jan. 13, 2017 for U.S. Appl. No. 14/609,332.
Office Action dated Feb. 29, 2016 for U.S. Appl. No. 14/609,334.
Office action dated Mar. 7, 2019 for U.S. Appl. No. 13/945,138.
Office Action dated Mar. 7, 2017 for U.S. Appl. No. 15/274,764.
Office Action dated Mar. 7, 2017 for U.S. Appl. No. 15/274,809.
Office action dated Mar. 7, 2019 for U.S. Appl. No. 14/673,565.
Office Action dated Mar. 12, 2015 for U.S. Appl. No. 13/945,138.
Office action dated Mar. 19, 2018 for U.S. Appl. No. 14/470,503.
Office Action dated Mar. 23, 2017 for U.S. Appl. No. 13/945,138.
Office Action dated Mar. 28, 2016 for U.S. Appl. No. 14/673,565.
Office action dated Apr. 4, 2018 for U.S. Appl. No. 15/156,585.
Office action dated May 16, 19 for U.S. Appl. No. 14/515,324.
Office Action dated May 18, 2018 for U.S. Appl. No. 14/956,710.
Office Action dated May 31, 2017 for U.S. Appl. No. 15/274,764.
Office action dated Jun. 6, 2019 for U.S. Appl. No. 15/683,713.
Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
Office Action dated Aug. 5, 2015 for U.S. Appl. No. 13/945,138.
Office action dated Sep. 7, 2018 for U.S. Appl. No. 14/609,332.
Office Action dated Sep. 23, 2016 for U.S. Appl. No. 14/515,324.
Office action dated Oct. 4, 2018 for U.S. Appl. No. 14/515,324.
Office Action dated Oct. 7, 2016 for U.S. Appl. No. 13/945,138.
Office Action dated Nov. 2, 2017 for U.S. Appl. No. 15/156,585.
Office action dated Nov. 2, 2018 for U.S. Appl. No. 14/609,334.
Office Action dated Nov. 15, 2016 for U.S. Appl. No. 14/609,334.
Office action dated Nov. 16, 2017 for U.S. Appl. No. 14/609,332.
Office Action dated Nov. 30, 2015 for U.S. Appl. No. 13/945,138.
Office Action dated Nov. 30, 2017 for U.S. Appl. No. 14/673,565.
Office Action dated Dec. 17, 2015 for U.S. Appl. No. 14/515,324.
Office action dated Dec. 18, 2017 for U.S. Appl. No. 14/515,324.
Office action dated Dec. 18, 2018 for U.S. Appl. No. 14/470,503.
Office action dated Dec. 19, 2017 for U.S. Appl. No. 13/945,138.
Notice of Allowance dated Jul. 7, 2017 for U.S. Appl. No. 15/274,764.
Notice of Allowance dated Sep. 14, 2017 for U.S. Appl. No. 15/274,809.
U.S. Appl. No. 14/917,243 Office Action dated Jun. 5, 2020.
U.S. Appl. No. 13/945,138 Notice of Allowance dated Dec. 22, 2020.
U.S. Appl. No. 14/515,324 Office Action dated Dec. 4, 2020.
U.S. Appl. No. 14/609,334 Notice of Allowance dated Dec. 10, 2020.
U.S. Appl. No. 14/609,334 Office Action dated Oct. 29, 2020.
U.S. Appl. No. 14/673,565 Office Action dated Dec. 24, 2020.
U.S. Appl. No. 14/673,565 Office Action dated Jun. 12, 2020.
U.S. Appl. No. 15/274,948 Notice of Allowance dated May 14, 2020.
U.S. Appl. No. 15/274,948 Office Action dated Nov. 20, 2018.
U.S. Appl. No. 15/406,572 Notice of Allowance dated Oct. 28, 2020.
U.S. Appl. No. 15/406,572 Office Action dated Apr. 14, 2020.
U.S. Appl. No. 15/406,572 Office Action dated Feb. 7, 2019.
U.S. Appl. No. 15/406,572 Office Action dated Nov. 15, 2019.
U.S. Appl. No. 15/917,480 Notice of Allowance dated Dec. 17, 2020.
U.S. Appl. No. 15/917,480 Office Action dated Nov. 20, 2020.
U.S. Appl. No. 16/267,771 Notice of Allowance dated Aug. 10, 2020.
U.S. Appl. No. 16/711,236 Office Action dated Dec. 10, 2020.
U.S. Appl. No. 16/900,563 Notice of Allowance dated Dec. 17, 2020.
U.S. Appl. No. 16/900,563 Office Action dated Nov. 9, 2020.
U.S. Appl. No. 13/945,138 Office Action dated Dec. 10, 2019.

(56) References Cited

OTHER PUBLICATIONS

U.S. Appl. No. 14/470,503 Notice of Allowance dated Feb. 27, 2019.
U.S. Appl. No. 14/515,324 Office Action dated Mar. 31, 2020.
U.S. Appl. No. 14/609,334 Office Action dated Jan. 8, 2020.
U.S. Appl. No. 14/956,710 Notice of Allowance dated Jan. 9, 2019.
U.S. Appl. No. 15/683,713 Notice of Allowance dated Mar. 10, 2020.
U.S. Appl. No. 15/683,713 Notice of Allowance dated Nov. 27, 2019.
U.S. Appl. No. 15/683,713 Office Action dated Oct. 10, 2019.
U.S. Appl. No. 15/917,480 Office Action dated Jan. 10, 2020.
U.S. Appl. No. 16/267,771 Office Action dated Feb. 6, 2020.
Adams et al., Theoretical design and evaluation of endoluminal ultrasound applicators for thermal therapy of pancreatic cancer under image guidance. AIP Conference Proceedings. Mar. 17, 2017; 1821 (1):110002. doi: http://dx.doi.org/10.1063/1.4977640.
Chathadi et al., The role of endoscopy in ampullary and duodenal adenomas. Gastrointest Endosc. Nov. 2015;82(5):773-81. doi: 10.1016/j.gie.2015.06.027. Epub Aug. 7, 2015.
Cherrington et al., Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.
Galvao Neto et al., Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
Grikscheit, et al. Tissue-engineered small intestine improves recovery after massive small bowel resection. Ann Surg., 2004, 240:748-754.
Miyawaki et al., Inhibition of gastric inhibitory polypeptide signaling prevents obesity. Nat Med. Jul. 2002;8(7):738-42. doi: 10.1038/nm727. Epub Jun. 17, 2002.
Rajagopalan et al., Endoscopic Duodenal Mucosal Resurfacing for the Treatment of Type 2 Diabetes: 6-Month Interim Analysis From the First-in-Human Proof-of-Concept Study. Diabetes Care. Dec. 2016;39(12):2254-2261. doi: 10.2337/dc16-0383. Epub Aug. 12, 2016.
Rubino et al., Potential of surgery for curing type 2 diabetes mellitus. Ann Surg. Nov. 2002;236(5):554-9. doi: 10.1097/00000658-200211000-00003.
Sarria et al., Morphometric study of the layers of the canine small intestine at five sampling sites. Vet J. Jun. 2012;192(3):498-502. doi: 10.1016/j.tvjl.2011.06.041. Epub Nov. 3, 2011.
Semkova et al., Autologous transplantation of genetically modified iris pigment epithelial cells: a promising concept for the treatment of age-related macular degeneration and other disorders of the eye. Proc Natl Acad Sci U S A. Oct. 1, 2002;99(20):13090-5. doi: 10.1073/pnas.202486199. Epub Sep. 18, 2002.
Sen et al., Autologous transplantation of endothelial progenitor cells genetically modified by adeno-associated viral vector delivering insulin-like growth factor-1 gene after myocardial infarction. Hum Gene Ther. Oct. 2010;21(10):1327-34. doi: 10.1089/hum.2010.006.
Tolman et al., Spectrum of liver disease in type 2 diabetes and management of patients with diabetes and liver disease. Diabetes Care. Mar. 2007;30(3):734-43. doi: 10.2337/dc06-1539.
Tomizawa et al., Clinical Outcome of Endoscopic Mucosal Resection (EMR) of Sporadic, Non-Ampullary Duodenal Adenoma (SNADA) : Predictor Analysis of Safety and Efficacy From a High Volume U.S. Tertiary Referral Center. Gastrointestinal Endoscopy. 377. May 2017, vol. 85, Issue 5, Supplement, p. AB72. doi: http://dx.doi.org/10.1016/j.gie.2017.03.089.
Van Baar et al., Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. doi: http://dx.doi.org/10.1016/S0016-5085(17)32851-2.

\* cited by examiner

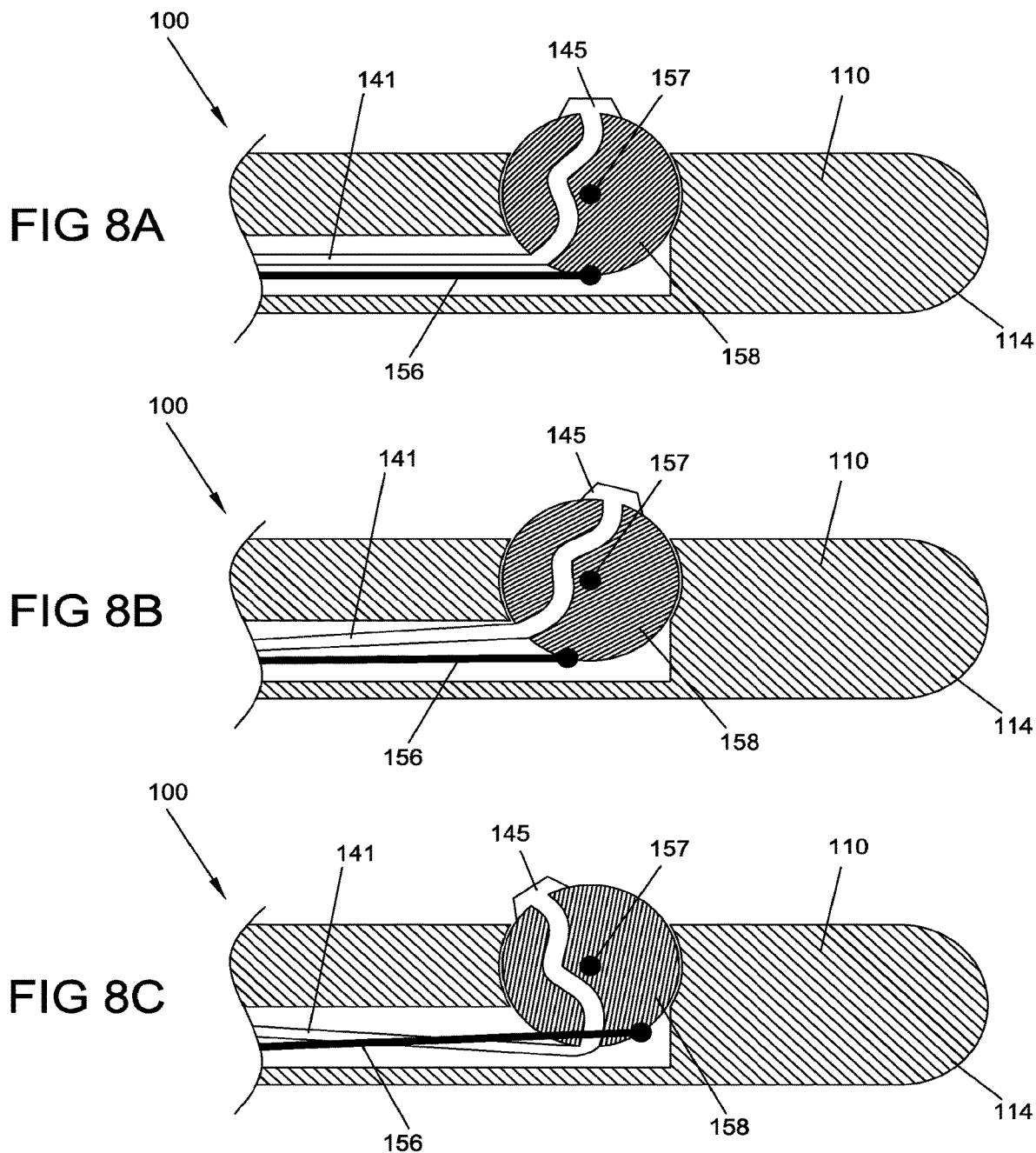

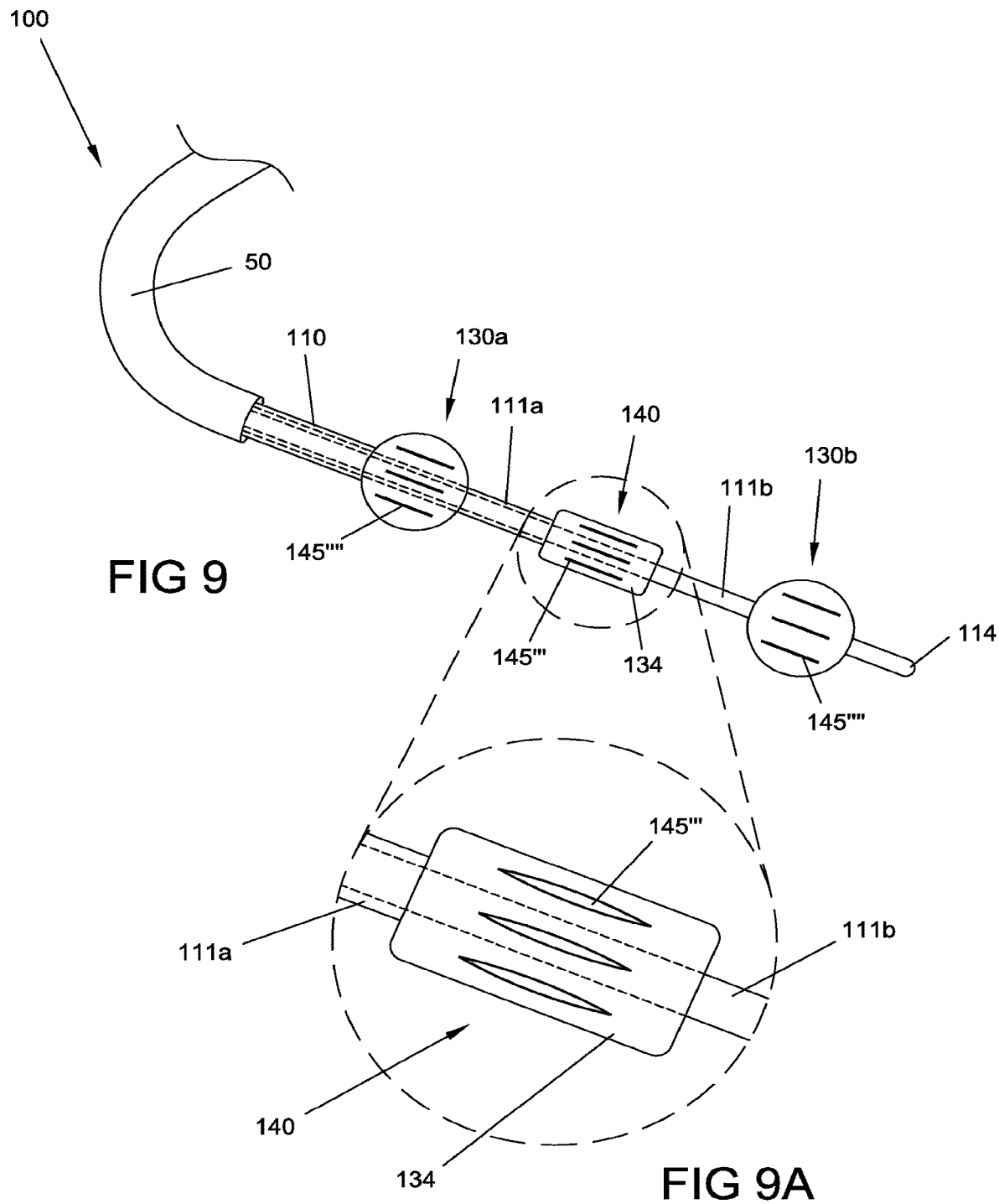

ABLATION SYSTEMS, DEVICES AND METHODS FOR THE TREATMENT OF TISSUE

RELATED APPLICATIONS

This application is a continuation of U.S. patent application Ser. No. 18/786,113, filed Jul. 26, 2024, which is a continuation of Ser. No. 17/192,671, filed Mar. 4, 2021, which is a continuation of U.S. patent application Ser. No. 14/609,334, filed Jan. 29, 2015, now U.S. Pat. No. 10,973,561, issued Apr. 13, 2021, which is a continuation of International Patent Application No. PCT/US2013/054219, filed Aug. 8, 2013, which claims the benefit of U.S. Provisional Application Ser. No. 61/681,502, filed Aug. 9, 2012, the entire contents of each of which is incorporated herein by reference in its entirety.

U.S. patent application Ser. No. 14/609,334, filed Jan. 29, 2015, is also related to PCT/US2012/021739, filed on Jan. 18, 2012, which claimed the benefit of U.S. Provisional Application Ser. No. 61/434,319, entitled "Method and System for Treatment of Diabetes", filed Jan. 19, 2011, and of U.S. Provisional Application Ser. No. 61/538,601, entitled "Devices and Methods for the Treatment of Tissue", filed Sep. 23, 2011; U.S. Provisional Application Ser. No. 61/603,475, entitled "Heat Ablation Systems, Devices and Methods for the Treatment of Tissue", filed Feb. 27, 2012; and U.S. Provisional Application Ser. No. 61/635,810, entitled "Tissue Expansion Devices, Systems and Methods", filed Apr. 19, 2012; U.S. Provisional Application Ser. No. 61/677,422, entitled "Electrical Energy Ablation Systems, Devices and Methods for the Treatment of Tissue", filed Jul. 30, 2012; the contents of which are each incorporated herein by reference in their entirety.

TECHNICAL FIELD

The embodiments disclosed herein relate generally to systems, devices and methods for treating tissue, particularly gastrointestinal tissue.

BACKGROUND

Diabetes is a metabolic disease in which a person develops high blood sugar because the person's body does not produce enough insulin or the cells of the body are incapable of effectively responding to the produced insulin. Primarily, diabetes is of two types: Type-1 and Type-2. Type-1 diabetes results due to the body's failure to produce enough insulin, and Type-2 diabetes results from the body's autoimmune destruction of pancreatic beta cells and, consequently, the body's failure to produce enough insulin. Type 2 diabetes is a complex metabolic derangement that causes hyperglycemia through insulin resistance (in which the body's cells fail to properly utilize the produced insulin) and inadequate insulin production to meet the body's needs.

Currently, there are several procedures aimed at treating diabetes based on the above concept. The procedures require major surgery, removal of portions of the GI tract, and/or long-term implants. As with any major surgery, gastric bypass surgery carries a risk of complications.

Devices have been developed to delivery energy to the body. For example, cardiac ablation devices have been designed to delivery ablative energy to coronary tissue. Additionally, urethral resection devices have been designed to burn or cut away portions of a prostate. Each of these technologies has been modified and adapted toward effective usage in the particular portion of the body to be treated as well as the particular disease to be treated.

There is a need for systems and methods that can provide a therapeutic treatment of the GI tract by the application of energy to the GI tract. Specifically, there is a need to provide a treatment of diabetes with a procedure in the GI tract that is less invasive than gastric bypass surgery and has other advantages for patients.

SUMMARY

According to one aspect of the present inventive concepts, a device for ablating tissue of a patient with a delivered vapor is provided. The device includes an elongate shaft having a proximal portion and a distal portion and at least one fluid delivery element positioned on the elongate shaft distal portion. The fluid delivery element is configured to deliver ablative fluid to target tissue. The device is configured to ablate duodenal mucosal tissue while avoiding damaging duodenal adventitial tissue.

The device can be configured to ablate at least an outer layer of duodenal submucosal tissue. The device can be configured to avoid or otherwise not ablate at least the outermost 100 microns of duodenal submucosal tissue, or at least the outermost 200 microns of duodenal submucosal tissue. The device can be configured to ablate ileal mucosal tissue and/or gastric mucosal tissue. The device can be configured to minimize damage to at least one of the pylorus or the ampulla of Vater, for example where the device includes an advanceable sheath configured to prevent ablative fluid from damaging at least one of the pylorus or the ampulla of Vater. The device can be configured to identify the ampulla of Vater. The device can be configured to minimize distension of duodenal tissue, for example where the device limits the forces applied to the duodenal wall to a level at or below 1.0 psi, below 0.5 psi, or below 0.3 psi. The device can be configured to create scar tissue. The device can be further configured to also avoid damaging tissue including the duodenal muscularis layer; ampulla of Vater; bile duct; pancreas; pylorus; muscularis externae; serosa; and combinations of these. The device can be configured to desiccate the target tissue and/or the device can be configured to perform a non-desiccating treatment of the target tissue.

The device can be configured to ablate duodenal mucosal tissue in a curved segment of duodenum. The device can be configured to ablate a tissue layer of at least 500 microns in thickness, or at least 1 mm in thickness. The device can be configured to ablate a volume of tissue comprising a surface area and a depth where the magnitude of the depth is less than approximately 1.0% of the magnitude of the surface area, or where the magnitude of the depth is less than approximately 0.1% of the magnitude of the surface area.

The device can be configured to treat substantially the entire length of the duodenum simultaneously. The device can be configured to treat a first length of duodenum in a first ablative fluid application and a second length of duodenum in a second ablative fluid application, for example where the first length of duodenum overlaps the second length of duodenum.

The elongate shaft can be configured to be passed through a working channel of an endoscope such as a 6.0 mm working channel, a 4.2 mm working channel, a 3.8 mm working channel, a 3.2 mm working channel, or a 2.8 mm working channel. Alternatively or additionally, the elongate shaft can be configured to pass or otherwise be positioned alongside an endoscope, such as an endoscope that has been placed in a gastrointestinal tract. The device can be configured for over-the-wire delivery.

In some embodiments, the device does not include a barrier positioned between the delivered ablative fluid and the target tissue, such as when the delivered fluid directly contacts the target tissue.

The device can be configured to deliver a first volume of ablative fluid during a first time period, deliver no ablative fluid during a subsequent second time period, and then deliver a second volume of ablative fluid during a subsequent third time period. In some embodiments, the first volume of ablative fluid and the second volume of ablative fluid are configured to cause a non-desiccating ablation of target tissue. In some embodiments, the first volume of ablative fluid delivered includes a different quantity of energy delivered than the second volume of ablative fluid delivered, for example the first volume of ablative fluid delivered includes a greater quantity of energy delivered than the second volume of ablative fluid delivered. In some embodiments, the first volume of ablative fluid delivered includes a greater volume of fluid than the second volume of ablative fluid delivered. In some embodiments, the first time period is a different length of time than the third time period. In some embodiments, the first volume of ablative fluid delivered includes a temperature profile of fluid different than a temperature profile of fluid for the second volume of ablative fluid delivered, for example where the difference includes a different relatively constant temperature of delivered fluid, or where the difference includes a different range of temperatures of delivered fluid. In some embodiments, the first volume of ablative fluid includes a different fluid than the second volume of ablative fluid. In some embodiments, the first volume of ablative fluid and the second volume of ablative fluid are configured to cause agitation of ablative fluid. In some embodiments, the first volume of ablative fluid is delivered to a first tissue portion and the second volume of ablative fluid is also delivered to the first tissue portion. Alternatively, the first volume of ablative fluid can be delivered to a first tissue portion and the second volume of ablative fluid can be delivered to a second tissue portion comprising different tissue than the first tissue portion. In some embodiments, the second time period is no more than 45 seconds, no more 25 seconds, or no more than 10 seconds.

The device can further include a radially expandable element attached to the elongate shaft distal portion. Examples of radially expandable elements include: balloon; radially deployable arms; expandable cage; and combinations of these. The radially expandable element can be configured to position the at least one fluid delivery element relative to the target tissue. In some embodiments, the device further includes at least one centering member positioned on the radially expandable element and configured to position the at least one fluid delivery element relative to the target tissue. The at least one centering member can include at least one ridge on the radially expandable element, and in some embodiments, the at least one centering member can include multiple ridges. The at least one centering element can include a height of at least 250 microns. The at least one fluid delivery element can include a first top surface, and the centering element can include a second top surface offset from the first top surface by at least 250 microns. The radially expandable element can be configured to position the at least one fluid delivery element away from a luminal wall, for example at least 1 mm from a luminal wall. In some embodiments, the at least one fluid delivery element is mounted to the radially expandable element. The at least one fluid delivery element can be positioned a distance of at least 1 mm from target tissue when the radially expandable element is expanded.

In some embodiments, the radially expandable element includes a balloon having an external surface. The at least one fluid delivery element can be mounted to and/or pass through the external surface of the balloon. The at least one fluid delivery element can include an opening in the external surface of the balloon, for example a hole and/or a slit such as a slit that is configured to open when the expandable element is pressurized above a threshold. The balloon can include a dog-bone shaped balloon. The balloon can include a non-compliant balloon. The balloon can include a hydrophilic coating on its external surface.

In some embodiments, the radially expandable element includes an expandable cage. The device can further include a deployment shaft operably connected to the expandable cage, for example where the deployment shaft is configured such that retraction and/or advancement of the shaft causes the expandable cage to radially expand.

In some embodiments, the radially expandable element includes radially deployable arms.

In some embodiments, the radially expandable element includes a helical coil. The at least one fluid delivery element can include multiple nozzles positioned along the helical coil.

The radially expandable element can be configured to position at least a portion of the at least one fluid delivery element in the approximate center of a duodenum. The radially expandable element can be configured to manipulate tissue, for example where the tissue manipulation includes a manipulation selected from the group consisting of: linearizing curvilinear tissue; distending tissue; expanding tissue; and combinations of these. The radially expandable element can be configured to occlude a body lumen, such as a tubular tissue portion of the gastrointestinal tract.

The device can further include a second radially expandable element. The at least one fluid delivery element can include a first fluid delivery element attached to the first radially expandable element and a second fluid delivery element attached to the second radially expandable element. The first fluid delivery element can be configured to deliver a first ablative fluid to target tissue and the second fluid delivery element can be configured to deliver a second ablative fluid to target tissue. The first ablative fluid can be similar or dissimilar to the second ablative fluid. The second radially expandable element can be configured to manipulate tissue, for example to at least linearize or distend tissue. The first and/or second radially expandable elements can be configured to occlude a body lumen.

The at least one fluid delivery element can include an element selected from the group consisting of: nozzle; opening; hole; slit; permeable membrane; misting element; vaporizer; and combinations of these. The at least one fluid delivery element can be further configured to deliver a second fluid, where the second fluid can include a fluid selected from the group consisting of: washing fluid; counter-acting fluid; second ablative fluid; cooling fluid; warming fluid; and combinations of these. The at least one fluid delivery element can be configured to deliver the second fluid to tissue and/or to at least a portion of the device.

The at least one fluid delivery element can include a first fluid delivery element and a second fluid delivery element, where the first fluid delivery element can be configured to deliver the ablative fluid to target tissue. The first fluid delivery element can be configured to deliver a first ablative fluid to target tissue, and the second fluid delivery element can be configured to deliver a second ablative fluid to target tissue. The first and second ablative fluids can be similar or dissimilar. The second fluid delivery element can be configured to deliver a cooling fluid; a washing fluid; a counteracting fluid; and combinations of these.

The device can further include a centering assembly configured to position the at least one fluid delivery element at a relatively fixed distance from target tissue. The target tissue can include tubular tissue. The centering element can include a radially expandable element and/or radially deployable arms.

The device can include at least one fluid delivery tube fluidly connected to the at least one fluid delivery element. In some embodiments, the at least one fluid delivery tube includes a first delivery tube and a second delivery tube, and the at least one fluid delivery element includes a first fluid delivery element fluidly connected to the first delivery tube and a second fluid delivery element fluidly connected to the second delivery tube, for example where the first fluid delivery element is configured to deliver a first ablative fluid and the second fluid delivery element is configured to deliver a second ablative fluid. In some embodiments, the at least one fluid delivery tube includes a first delivery tube, and the at least one fluid delivery element includes a first fluid delivery element fluidly connected to the first delivery tube and a second fluid delivery element fluidly connected to the first delivery tube. The at least one fluid delivery tube includes a length and a diameter, where the diameter can be reduced along the length. In some embodiments, the at least one fluid delivery element includes a first fluid delivery element and a more distal second fluid delivery element, where the at least one fluid delivery tube diameter is reduced such that the rate of fluid delivered out of the first fluid delivery element approximates the rate of fluid delivered out of the second fluid delivery element.

The at least one fluid delivery element can be configured to deliver a near 360° delivery of fluid, for example where the at least one fluid delivery element includes a circumferential array of multiple fluid delivery elements and/or a rotating fluid delivery element such as a rotating nozzle. The at least one fluid delivery element can be configured to deliver ablative fluid to a 450° to 350° circumferential portion of target tissue. In these embodiments, the device can be configured to be rotated to treat a 360° segment of target tissue. In some embodiments, the at least one fluid delivery element can be constructed and arranged to prevent formation of a full circumferential scar. The at least one fluid delivery element can include an array of fluid delivery elements that can be configured to deliver the ablative fluid to less than or equal to a 350° circumferential portion of target tissue, for example to a 300° to 350° circumferential portion of target tissue.

In some embodiments, the at least one fluid delivery element includes at least one rotating and/or translating fluid delivery element. The device can be configured such that an operator can manually rotate and/or translate the at least one fluid delivery element. Alternatively or additionally, the device can be configured to automatically rotate and/or translate the at least one fluid delivery element. In some embodiments, the device is constructed and arranged to translate the at least one fluid delivery element at a rate of at least 10 cm/min, or at least 20 cm/min.

In some embodiments, the at least one fluid delivery element can include at least one nozzle, such as at least one nozzle configured to deliver a cone-shaped spray of ablative fluid.

The at least one fluid delivery element can be configured to self-position the at least one fluid delivery element relative to luminal wall tissue, such as with reactive forces that result when fluid is delivered through the at least one fluid delivery element. For example, the at least one fluid delivery element can include multiple nozzles configured to position the at least one fluid delivery element relative to luminal wall tissue with multiple reactive forces that result when fluid is delivered through the multiple nozzles such as where the multiple nozzles include a first nozzle and a second nozzle, and the fluid delivered through the first and second nozzles is varied to move at least the first nozzle.

The ablative fluid can include steam.

The ablative fluid can include a fluid at a temperature less than 100° C., for example at a temperature between 60° C. and 90° C.

The ablative fluid can include a gas, for example a gas between 60° C. and 99° C., or between 70° C. and 90° C. The ablative fluid can include a gas above 100° C. In some embodiments, the at least one fluid delivery element can be further configured to deliver a cooling gas to the target tissue.

The ablative fluid can include a chemical agent. Examples of chemical agents include: sclerotic agent; acid; base; saline; alcohol; carbon dioxide; nitrous oxide; nitrogen; acetic acid; glycerol; and combinations of these. The chemical agent can include a mixture of one or more liquids mixed with one or more types of abrasive particles. The device can further include a counteracting agent, for example an agent configured to provide an effect on the chemical agent selected from the group consisting of: neutralize, impede; reduce and combinations of these. The at least one fluid delivery element can be configured to deliver the counteracting agent. The at least one fluid delivery element can include a first fluid delivery element configured to deliver the ablative fluid and a second fluid delivery element configured to deliver the counter-acting agent. Examples of counteracting agents include: anti-sclerotic agent; base; acid; buffer solution; saline; water; and combinations of these.

The ablative fluid can include a visualizable material, for example a material selected from the group consisting of: radiopaque agent; ultrasonically visible material; magnetically visible material; and combinations of these. The device can be configured to assess the status of tissue ablation based on visualization of the visualizable material.

The elongate shaft distal portion can be at least one of deflectable or steerable. The elongate shaft can include a first fluid delivery tube in fluid connection with the at least one fluid delivery element. The first fluid delivery tube can include a lumen of the elongate shaft. The first fluid delivery tube can include a hollow tube, such as a hollow tube that passes within or alongside the elongate shaft. The first fluid delivery tube can include a lumen fluidly connected to a hollow tube. The device can further include an insulator layer surrounding at least a portion of the first fluid delivery tube. The device can further include a second fluid delivery tube, for example where the first delivery tube can be configured to deliver a first ablative fluid and the second fluid delivery tube can be configured to deliver a second ablative fluid. The second fluid delivery tube can surround at least a portion of the first fluid delivery tube. The second fluid delivery tube can be configured to reduce heat transfer across the first fluid delivery tube, such as when the second fluid delivery tube is constructed and arranged to function as an insulator.

The elongate shaft can further include an outer surface and an insulator layer, where the insulator layer can be configured to reduce heat transfer to the elongate shaft outer surface.

The device can further include at least one sensor configured to provide a signal. The device can be configured to deliver the ablative fluid based on the at least one sensor signal. Examples of sensors include: temperature sensors such as thermocouples, thermistors, resistance temperature detectors and optical temperature sensors; strain gauges; impedance sensors such as tissue impedance sensors; pressure sensors; blood sensors; optical sensors such as light sensors; sound sensors such as ultrasound sensors; electromagnetic sensors such as electromagnetic field sensors; visual sensors; and combinations of these. The at least one sensor can include a visual sensor configured to provide an image of tissue, for example where the visual sensor comprises an imaging device selected from the group consisting of: visible light camera; infrared camera; CT scanner; magnetic resonance imager (MRI); and combinations of these. The device can be configured to deliver the ablative fluid based on the visual sensor signal, for example based on a change in tissue color.

The device can further include a heat generator configured to add energy to the ablative fluid. The heat generator can include one or more heating coils. The device can further include a balloon, where the heating coil can be positioned in the balloon and the at least one fluid delivery element can be attached to the balloon. The heat generator can include at least one of a heating coil or a wire configured to turn water to steam, or to add heat to a vaporized liquid. The heat generator can be positioned at a location selected from the group consisting of: in a radially expandable element; on a radially expandable element; proximal to a radially expandable element; proximal to the elongate shaft; proximate the at least one fluid delivery element; within the at least one fluid delivery element; within the elongate shaft; and combinations of these.

The device can further include a cooling generator configured to cool the target tissue. The cooling generator can be configured to cool the target tissue at a time selected from the group consisting of: prior to delivery of ablative fluid; during the delivery of ablative fluid; after delivery of ablative fluid; between a first ablative fluid delivery and a second ablative fluid delivery; and combinations of these. The cooling generator can include a cooling element positioned to contact tissue and remove heat from the contacted tissue, for example target tissue. The cooling generator can be configured to deliver a cooling fluid to the target tissue, for example a fluid delivered at a temperature below 37° C., between 0° C. and 7° C., or below 0° C.

The device can further include an agitating assembly configured to agitate the ablative fluid. The agitating assembly can be configured to cause the ablative fluid to be arranged as a relatively uniform dispersion of fluid. The agitating assembly can be configured to create turbulence within a volume of ablative fluid. The agitating assembly can be configured to agitate the ablative fluid after it is delivered from the at least one fluid delivery element. The agitating assembly can be configured to perform at least one of: rapidly evacuate fluids from or rapidly deliver fluids to a segment of gastrointestinal lumen. The agitating assembly can be configured to move the at least one fluid delivery element, for example in a motion selected from the group consisting of: rotation about an axis of gastrointestinal tract; translation along an axis of gastrointestinal tract; advancement toward gastrointestinal luminal wall; retraction from gastrointestinal luminal wall; and combinations of these. The agitating assembly can include a balloon configured to be inflated and deflated to agitate delivered ablative fluid. The agitating assembly can include a proximal gastrointestinal lumen sealing element and a distal gastrointestinal lumen sealing element, where the agitating assembly can be configured to move at least one of the proximal sealing element or the distal sealing element to cause agitation of delivered ablative fluid. The agitating assembly can be configured to vary the delivery rate of the ablative fluid, for example where the at least one fluid delivery element comprises a first fluid delivery element and a second fluid delivery element and where the agitating assembly varies the flow rate of at least the first fluid delivery element. The device can be configured to cause a non-desiccating treatment of tissue, and the agitating assembly can be configured to improve the duodenal mucosal tissue ablation, for example when the at least one fluid delivery element is configured to deliver the ablative fluid for at least three seconds.

The device can further include an outflow drain configured to remove fluid from at least one of the device or a gastrointestinal lumen. The device can be constructed and arranged to recirculated the removed fluid. The removed fluid can include ablative fluid. The device can further include an agitating assembly configured to vary the distance between the at least one fluid delivery element and the outflow drain to cause agitation of the ablative fluid. The at least one fluid delivery element can be constructed and arranged to remove fluid.

The device can further include a lumen sealing assembly configured to seal a portion of a gastrointestinal tract. In some embodiments, the lumen sealing assembly can be configured to place an occluding element in the gastrointestinal tract, and the device can be configured to deliver the ablative fluid proximal to the occluding element. In some embodiments, the lumen sealing assembly can include a first occluding element and a second occluding element, where the device is configured to place the first occluding element at a proximal gastrointestinal location and the second occluding element at a distal gastrointestinal location. In this embodiment, the device can be configured to deliver the ablative fluid between the first occluding element and the second occluding element. In some embodiments, the lumen sealing assembly can include a vacuum applying element. The lumen sealing assembly can be configured to apply a seal selected from the group consisting of: a pressure seal; a cryogenically applied seal such as an ice ball seal; a vacuum seal; and combinations of these. In some embodiments, the lumen sealing assembly can include a deployable sealing balloon, for example where the sealing balloon is configured to be deflated and left in the gastrointestinal tract for physiologic removal. The lumen sealing assembly can be configured to seal a portion of the gastrointestinal tract to protect one or more tissue locations such as the ampulla of Vater or the pylorus.

The device can further include a fluid removal assembly configured to remove fluid from the gastrointestinal tract. The removed fluid can include delivered ablative fluid; condensate of ablative fluid; ablative fluid; chyme; digestive fluids; gas; and combinations of these. The fluid removal assembly can include a vacuum applying element. The device can further include a fluid recycling assembly configured to recirculated and/or deliver the removed fluid through a fluid delivery element.

The device can further include a gas jet assembly configured to deliver gas toward a wall of the gastrointestinal tract. The gas jet assembly can be further configured to cause agitation of ablative fluid in a body lumen. The gas jet assembly can include the at least one fluid delivery element, and the at least one fluid delivery element can be configured to deliver the gas. The delivered gas can include dehumidified gas, for example gas having a relative humidity less than 20% or less than 10%. The gas jet assembly can be configured to move fluid from one location in the gastrointestinal tract to another location in the gastrointestinal tract. The gas jet assembly can be configured to deliver gas at a temperature below 37° C., for example between 0° C. and 7° C., or between 2° C. and 7° C. such as at a temperature of approximately 4° C. The gas jet assembly can be configured to deliver the gas for at least 30 seconds, for at least 20 seconds, or for at least 10 seconds. The gas jet assembly can be configured to deliver gas at a temperature below 0° C. for less than or equal to 20 seconds, for less than or equal to 10 seconds, or for less than or equal to 5 seconds. The gas jet assembly can be configured to deliver carbon dioxide below 37° C. The gas jet assembly can be configured to deliver gas at a temperature above 42° C. such as when the gas jet assembly is configured to dehumidify one or more portions of the gastrointestinal tract.

The device can further include a gravimetric sensor. The device can be configured to orient the at least one fluid delivery element based on a signal from the gravimetric sensor, for example in a relatively upward and/or side-ways direction, such as to allow gravity to move the ablative fluid along a tissue wall after delivery. The orientation of the at least one fluid delivery element can be manual and/or automatic. The device can further comprise a fluid removal element, where the device is configured to orient the fluid removal element based on a signal from the gravimetric sensor.

The at least one fluid delivery element can include a first fluid delivery element and a second fluid delivery element. The second fluid delivery element can include a nozzle. In some embodiments, the first fluid delivery element can be configured to deliver ablative fluid to target tissue, and the second fluid delivery element can be configured to deliver cooling fluid to tissue, for example where the second fluid delivery element can be configured to deliver the cooling fluid to limit the volume of tissue effected by the delivered ablative fluid. The second fluid delivery element can be configured to deliver the tissue cooling fluid to stop or reduce ablation of tissue. The second fluid delivery element can be configured to deliver the tissue cooling fluid to cool a component of the device. In some embodiments, the first fluid delivery element can be configured to deliver ablative fluid to target tissue, and the second fluid delivery element can be configured to deliver a washing fluid to wash at least a portion of the device and/or tissue.

The device can further include a tissue expansion assembly. For example, the tissue expansion assembly can be configured to expand submucosal tissue. In some embodiments, the tissue expansion assembly can include at least one needle configured to deliver fluid to duodenal tissue to cause duodenal submucosal tissue expansion. In some embodiments, the tissue expansion assembly can include at least one fluid jet nozzle configured to deliver fluid that penetrates duodenal tissue and causes duodenal submucosal tissue expansion.

The device can further include a cooling fluid delivery element configured to deliver a cooling fluid. The cooling fluid delivery element can include the at least one fluid delivery element. In some embodiments, the at least one fluid delivery element can include a first fluid delivery element configured to deliver the ablative fluid to target tissue and a second delivery element configured to deliver the cooling fluid. The cooling fluid can include a fluid below 37° C., or a fluid below 20° C. The cooling fluid can include a fluid selected from the group consisting of: a liquid; a gas; and combinations of these. The cooling fluid can be delivered prior to and/or after delivering the ablative fluid. In some embodiments, the device can be configured to deliver the ablative fluid in a first volume followed by a second volume, and the cooling fluid can be delivered between the delivery of the first volume and the second volume. For example, the ablative fluid can include steam, and the three fluid deliveries can be configured to achieve an average temperature between 70° C. and 90° C.

The device can further include at least one non-fluid delivery ablation element. Examples of non-fluid delivery ablation elements include: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these.

According to another aspect of the present inventive concepts, a system for ablating tissue with delivered vapor includes an ablation device, where the ablation device can be the same or similar to the ablation device described hereabove, and an energy delivery unit configured to deliver ablative fluid to the ablation device at least one fluid delivery element.

The system can be configured to deliver ablative fluid to tissue and avoid desiccation of the tissue. The system can be configured to deliver ablative fluid to tissue and avoid detachment of tissue particles. The system can be configured to deliver ablative fluid for at least one second to treat at least a portion of the tissue, or for at least three seconds. The system can be configured to deliver ablative fluid to tissue and to cause desiccation of the tissue. The system can be configured to deliver ablative fluid to tissue and to cause tissue particles to detach from a gastrointestinal surface.

The energy delivery unit can be configured to heat the ablative fluid. The energy delivery unit can include a pump, for example a pump configured to deliver the ablative fluid at a flow rate of at least 500 ml/min, or at least 750 ml/min. The energy delivery unit can be configured to provide pulse-width modulated delivery of ablative fluid, for example so as to precisely control the temperature of the target tissue.

The energy delivery unit can be configured to maintain the temperature of the target tissue below 100° C., such as between 60° C. and 90° C., or between 75° C. and 85° C. The energy delivery unit can configured to maintain the temperature of the target tissue at a setpoint temperature and to produce ablative fluid at a temperature above the setpoint temperature, for example where the setpoint temperature is between 60° C. and 75° C. In some embodiments, the setpoint temperature can vary over time.

The energy delivery unit can include a first heat source and a second heat source. The first heat source can provide fluid at a variable temperature and the second heat source can provide fluid at a fixed temperature.

The system can include a pre-heating assembly configured to pre-heat at least a portion of the ablation device. The ablation device can further include a fluid delivery tube in fluid communication with the at least one fluid delivery element, and the pre-heating assembly can be configured to pre-heat at least the fluid delivery tube. The ablation device shaft can include a lumen in fluid communication with the at least one fluid delivery element, and the pre-heating assembly can be configured to pre-heat at least the ablation device shaft lumen. The pre-heating assembly can be configured to pre-heat at least a portion of the shaft and/or at least a portion of the at least one fluid delivery element. The ablation device can include an insulator configured to reduce the transfer of heat to the shaft during the pre-heating of the at least a portion of the ablation device. The pre-heating assembly can circulate and/or recirculate pre-heating fluid through at least a portion of the shaft. The pre-heating assembly can deliver a pre-heating gas such as when the ablative fluid includes a liquid.

The system can include a second ablation device. The second ablation device can be similar to or the same as the first ablation device of the system, or a dissimilar ablation device. In some embodiments, the first ablation device at least one fluid delivery element includes a first set of multiple nozzles in a first pattern, and the second ablation device at least one fluid delivery element includes a second set of multiple nozzles in a second pattern different than the first pattern. The second ablation device can include an ablation device selected from the group consisting of: hot fluid filled balloon device; vapor ablation device; cryoablation device; laser ablation device; and combinations of these.

The system can include a fluid cooling assembly configured to cool one or more fluids, such as one or more liquids or gases. The cooled fluid can be delivered to a device component and/or tissue such as target tissue. The cooled fluid can be delivered to tissue for at least two seconds. In some embodiments, the system can be configured to deliver a first volume of cooling fluid at a first temperature followed by a second volume of cooling fluid at a second temperature, for example where the first temperature is lower than the second temperature.

The system can include a cooled fluid delivery device configured to deliver fluid below 37° C. to target tissue. The cooled fluid can be delivered prior to the delivery of the ablative fluid, during the delivery of the ablative fluid and/or after the delivery of the ablative fluid.

The system can include an endoscope.

The system can include a tissue expansion device, for example a tissue expansion device configured to expand one or more submucosal tissue layers of the duodenum.

The system can include an insufflation device. In some embodiments, the system includes an endoscope having a fluid delivery tube, and the fluid delivery tube includes the insufflation device.

The system can include a lumen diameter measurement assembly. The lumen diameter measurement assembly can include an expandable element configured to expand to contact a body lumen wall. The expandable element can include an element selected from the group consisting of: balloon; radially deployable arms; expandable cage; and combinations of these. The lumen diameter measurement assembly can be configured to provide lumen diameter information based on an image. The lumen diameter measurement assembly can be configured to provide lumen diameter information based on an achieved force. The lumen diameter measurement assembly can include an imaging device configured to provide an image including lumen diameter information. The device can further include a control rod configured to expand an assembly, where the control rod position correlates to lumen diameter.

BRIEF DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

FIGS. 8A-8C are side sectional views of the distal portion of an ablation device comprising a rotatable fluid delivery element, consistent with the present inventive concepts.

FIG. 9 is a side view of the distal portion of an ablation device comprising multiple expandable assemblies, consistent with the present inventive concepts.

FIG. 9A is a magnified side view of the fluid delivery element of the ablation device of FIG. 9, consistent with the present inventive concepts.

DETAILED DESCRIPTION OF THE DRAWINGS

Figure 1:
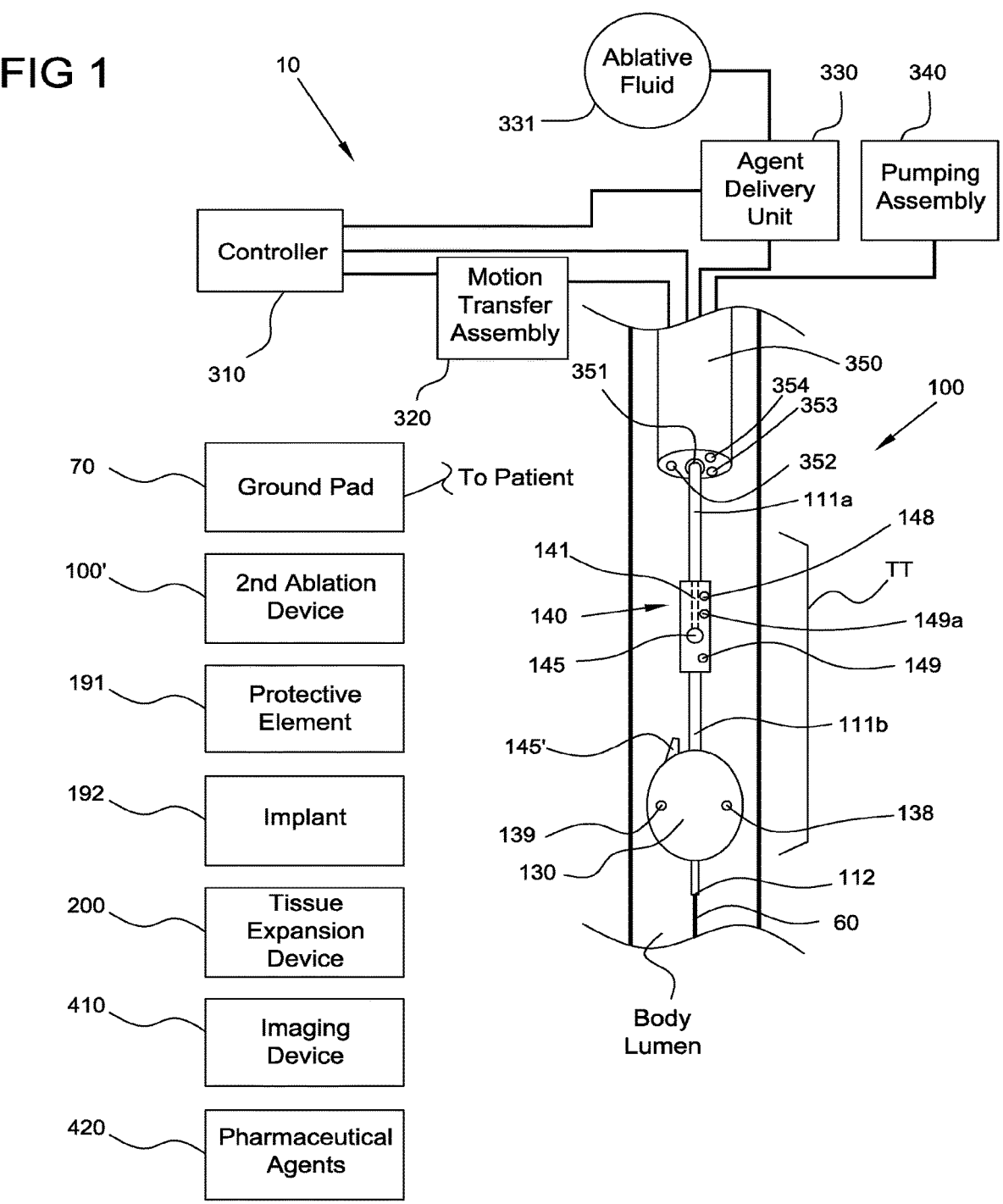
FIG. 1 is a schematic view of a system for ablating or otherwise treating target tissue, consistent with the present inventive concepts.

Reference will now be made in detail to the present embodiments of the inventive concepts, examples of which are illustrated in the accompanying drawings. Wherever practical, the same reference numbers will be used throughout the drawings to refer to the same or like parts.

Reference will now be made in detail to the present embodiments of the inventive concepts, examples of which are illustrated in the accompanying drawings. Wherever practical, the same reference numbers will be used throughout the drawings to refer to the same or like parts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is an object of the present inventive concepts to provide systems, methods and devices for safely and effectively ablating a volume of tissue (the "target tissue"), such as one or more layers of a portion of tubular or solid tissue, such as tissue of an organ or tissue of the gastrointestinal (GI) tract of a patient. The systems and devices of the present inventive concepts include one or more treatment assemblies configured to treat the target tissue, such as an assembly comprising a fluid delivery element configured to deliver ablative fluid, such as a heated fluid or chemically active fluid, directly onto the target tissue. Alternatively or additionally, other forms of treatment assemblies and/or treatment elements can be included. In some embodiments, the treatment assemblies and/or the one or more treatment elements contained therein are configured as described in applicant's co-pending International PCT Application Serial Number PCT/US12/21739, entitled "Devices and Methods for the Treatment of Tissue", filed Jan. 18, 2012, the contents of which is incorporated herein by reference in its entirety.

A treatment assembly can be configured to treat target tissue in one or more locations of the patient, such as one or more contiguous or discontiguous tissue locations. The target tissue comprises a three dimensional volume of tissue, and can include a first portion, a treatment portion, whose treatment has a therapeutic benefit to a patient, as well as a second portion, a "safety-margin" portion, whose treatment has minimal or no adverse effects to the patient. Non-target tissue can be identified (e.g. prior to and/or during the medical procedure), wherein the non-target tissue comprises tissue whose treatment by the treatment assembly should be reduced or avoided such as to reduce or prevent an undesired effect.

The target tissue treatment can cause one or more effects to the target tissue such as an effect selected from the group consisting of: modification of cellular function; cell death; apoptosis; instant cell death; cell necrosis; denaturing of cells; removal of cells; and combinations of these. In some embodiments, the target tissue treatment is configured to create scar tissue. Target tissue can be selected such that after treatment the treated target tissue and/or the tissue that replaces the target tissue functions differently than the pre-treated target tissue, such as to have a therapeutic benefit. The modified and/or replacement tissue can have different secretions and/or quantities of secretions than the pre-treated target tissue, such as to treat diabetes and/or obesity. The modified and/or replacement tissue can have different absorptive properties than the target tissue, such as to treat diabetes, obesity and/or hypercholesterolemia. The effect of the treatment can occur acutely, such as within twenty four hours, or after longer periods of time such as greater than twenty four hours or greater than one week.

Target tissue to be treated can comprise two or more tissue portions, such as a first tissue portion treated with a first treatment and/or a first treatment assembly, and a second tissue portion treated with a second treatment and/or a second treatment assembly. The first and second tissue portions can be directly adjacent and they can contain overlapping portions of tissue. The first and second treatment and/or treatment assemblies can be similar or dissimilar. Dissimilarities can include type and/or amount of energy to be delivered by an energy delivery based treatment assembly. Other dissimilarities can include but are not limited to: target tissue area treated; target tissue volume treated; target tissue length treated; target tissue depth treated; target tissue circumferential portion treated; ablative fluid type delivered; ablative fluid volume delivered; energy delivery type; energy delivery rate and/or amount; peak energy delivered; average temperature of target tissue treatment; maximum temperature achieved during target tissue treatment; temperature profile of target tissue treatment; duration of target tissue treatment; and combinations of these.

Target tissue can include tissue of the duodenum, such as tissue including all or a portion of the mucosal layer of the duodenum, such as to treat diabetes and/or obesity while leaving the duodenum anatomically connected after treatment. Replacement tissue can comprise cells that have migrated from one or more of: gastric mucosa; jejunal mucosa; an untreated portion of the duodenum whose mucosal tissue functions differently than the treated mucosal tissue functions prior to treatment; and combinations of these. Replacement tissue can include one or more tissue types selected from the group consisting of: scar tissue; normal intestinal mucosa; gastric mucosa; and combinations of these. In some embodiments, target tissue includes a treatment portion comprising the mucosal layer of the duodenum, and a safety-margin portion comprising a near-full or partial layer of the submucosal layer of the duodenum. In some embodiments, the target tissue comprises nearly the entire length of the mucosal layer of the duodenum, and can include a portion of the pylorus contiguous with the duodenal mucosa and/or a portion of the jejunum contiguous with the duodenal mucosa. Treatment of duodenal tissue can be performed to treat a disease and/or disorder selected from the group consisting of: diabetes; obesity; insulin resistance; a metabolic disorder and/or disease; and combinations of these. A near full circumferential portion (e.g. approximately 360°) of the mucosal layer of one or more segments of gastrointestinal tissue can be treated. In some embodiments, less than 360° of tubular tissue is treated, such as one or more circumferential portions less than 350°, or between 300° and 350°, such as to prevent a full circumferential scar from being created.

Target tissue can comprise tissue of the terminal ileum, such as to treat hypercholesterolemia and/or diabetes. In these embodiments, the target tissue can extend into the proximal ileum and/or the colon.

Target tissue can comprise gastric mucosal tissue, such as tissue regions that produce ghrelin and/or other appetite regulating hormones, such as to treat obesity and/or an appetite disorder.

Target tissue can comprise bladder wall tissue, such as to treat a disease and/or disorder selected from the group consisting of: interstitial cystitis; bladder cancer; bladder polyps; pre-cancerous lesions of the bladder; and combinations of these.

Target tissue can comprise tissue selected from the group consisting of: large and/or flat colonic polyps; margin tissue remaining after a polypectomy; and combinations of these. These tissue locations can be treated to treat residual cancer cells.

Target tissue can comprise airway lining tissue, such as to treat a disease and/or disorder selected from the group consisting of: bronchioalveolar carcinoma; other lung cancers; pre-cancerous lung lesions; and combinations of these.

Target tissue can comprise at least a portion of the intestinal tract afflicted with inflammatory bowel disease, such that Crohn's disease and/or ulcerative colitis can be treated.

Target tissue can comprise tissue of the oral cavity, such as to treat one or more of: oral cancers and a pre-cancerous lesion of the oral cavity.

Target tissue can comprise tissue of the nasopharynx, such as to treat nasal polyps.

Target tissue can comprise gastrointestinal tissue selected to treat Celiac disease and/or to improve intestinal barrier function.

The treatment assemblies, systems, devices and methods of the present inventive concepts can be configured to avoid ablating or otherwise adversely affecting certain tissue, termed "non-target tissue" herein. Depending on the location of tissue intended for treatment (i.e. target tissue), different non-target tissue can be applicable. In certain embodiments, non-target tissue can comprise tissue selected from the group consisting of: gastrointestinal adventitia; duodenal adventitia; the tunica serosa; the tunica muscularis; the outermost partial layer of the submucosa; ampulla of Vater such as during mucosal treatment proximate the ampulla of Vater; pancreas; bile duct; pylorus; and combinations of these.

As described herein, room pressure shall mean pressure of the environment surrounding the systems and devices of the present inventive concepts. Positive pressure includes pressure above room pressure or a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum.

The treatment assemblies and expandable elements of the present inventive concepts can be configured to automatically and/or manually expand in at least a radial direction. Typical expandable elements include but are not limited to: an inflatable balloon; a radially expandable cage or stent; one or more radially deployable arms; an expandable helix; an unfurlable compacted coiled structure; an unfurlable sheet; an unfoldable compacted structure; and combinations of these. In some embodiments, the expandable elements can comprise a radially expandable tube, such as a sheet of material resiliently biased in a radially expanded condition that can be compacted through a furling operation, or a sheet of material resiliently biased in a radially compact condition that can be expanded through an unfurling operation. The expandable elements can comprise a foldable sheet, such as a sheet configured to be folded to be radially compacted and/or to be unfolded to radially expand. In some embodiments, the expandable elements expand to contact tissue, such as to expand to a diameter similar to the diameter of the luminal wall tissue into which the expandable element has been placed. In some embodiments, the expandable elements expand to be closer to wall tissue, but remain at a distance (e.g. a fixed or pre-determined distance) from the tissue surface.

Each of the expandable assemblies of the present inventive concepts can include one or more fluid delivery elements, such as one or more nozzles configured to deliver ablative fluid to tissue. Each of the expandable assemblies of the present inventive concepts can include one or more other functional elements, such as are described in reference to the figures herebelow. The fluid delivery elements or other functional elements can be mounted on, within (e.g. within the wall) and/or inside of an expandable element such as a balloon or expandable cage. In some embodiments, the fluid delivery elements are not mounted to an expandable element, such as those attached to a shaft or other non-expandable ablation or other treatment device component.

In some embodiments, the treatment device comprises an ablation device including one or more fluid delivery elements configured for delivering ablative fluid to target tissue, the device further including one or more different types of ablation elements configured to treat target tissue. Examples of ablation elements include but are not limited to: a radiofrequency (RF) energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these.

The balloons of the present inventive concepts can be divided into two general categories: those that are composed of a substantially elastic material, such as silicone, latex, low-durometer polyurethane, and the like; and those that are composed of a substantially inelastic material, such as polyethylene terephthalate (PET), nylon, high-durometer polyurethane and the like. A third category includes balloons which include both elastic and inelastic portions. Within the category of elastic balloons, two subcategories exist: a first sub-category wherein a combination of material properties and/or wall thickness can be combined to produce a balloon that exhibits a measurable pressure-threshold for inflation, i.e. the balloon becomes inflated only after a minimum fluidic pressure is applied to the interior of the balloon; and a second sub-category, wherein the balloon expands elastically until an elastic limit is reached which effectively restricts the balloon diameter to a maximum value. It will be understood that the individual properties of the balloons in each of these categories can be applied to one or more advantages in the specific embodiments disclosed herein, these properties integrated singly or in combination. By way of example only, one or more of the following configurations can be employed: a highly elastic balloon can be used to achieve a wide range of operating diameters during treatment, e.g. during operation a desired balloon diameter can be achieved by adjustment of a combination of fluid temperature and pressure; a substantially inelastic balloon or a balloon that reaches its elastic limit within a diameter approximating a target tissue diameter (e.g. a duodenal mucosal diameter) can be used to achieve a relatively constant operating diameter that will be substantially independent of operating pressure and temperature; a balloon with a pressure-threshold for inflation can be used to maintain an uninflated diameter during relatively low pressure conditions of fluid flow and then achieve a larger operating diameter at higher pressure conditions of flow. Pressure-thresholded balloons can be configured in numerous ways. In one embodiment, a balloon is configured to have a relatively thick wall in its uninflated state, such as to maximize an electrically and/or thermally insulating effect while the balloon is maintained in this uninflated state. The balloon can be further configured such that its wall thickness decreases during radial expansion (e.g. to decrease an electrically and/or thermally insulating effect). In another embodiment, a balloon is configured to have a relatively small diameter in its uninflated state (e.g. a diameter that is small relative to the inner diameter of tubular target tissue such as the diameter of the mucosal layer of duodenal wall tissue), such as to minimize or completely eliminate apposition between the balloon and the surrounding tissue to minimize heat, RF and/or other energy transfer into the surrounding tissue until the balloon is fully inflated. In another embodiment, a balloon and an ablation system or device are configured to circulate a flow of fluid through the balloon (e.g. an elastic balloon or an inelastic balloon) at a sufficiently low enough pressure to prevent apposition of the balloon or other device component with target tissue, such as to pre-heat one or more surfaces of the ablation system or ablation device that are in fluid communication with the balloon. In this configuration, when the balloon or other ablation element is positioned to deliver energy to target tissue, the temperature of the balloon or other ablation element will be at a desired level or it will rapidly and efficiently reach the desired level for treatment (i.e. minimal heat loss to the fluid path components due to the pre-heating). These configurations provide a method of delivering energy to tissue with a hot fluid filled balloon, as well as a method of "thermal priming" prior to target tissue treatment, such as is described in applicant's U.S. Provisional Application Ser. No. 61/635,810, entitled "Tissue Expansion Devices, Systems and Methods", filed Apr. 19, 2012, the contents of which is incorporated herein by reference in its entirety.

Treatment Modality 1: APPOSITION BETWEEN A TREATMENT ASSEMBLY AND THE TARGET TISSUE IS ESTABLISHED BY ADJUSTING THE TREATMENT ASSEMBLY DIAMETER. At times during treatment when it is desirable to increase or otherwise modify the ablation of tissue by an ablation element (e.g. a fluid delivery element delivering ablative fluid, a hot fluid balloon delivering a thermal dose and/or an electrode delivering RF energy), the treatment assembly diameter (e.g. the diameter of a balloon, deployable cage, expandable tube or other expandable assembly) can be increased in situ to move an ablation element closer to or in contact with the native diameter of the target tissue, such as to the native diameter of tubular tissue such as duodenal wall tissue. At times during treatment when it is desirable to stop or otherwise decrease the amount of tissue ablation, the treatment assembly diameter can be reduced in situ, such as to prevent or reduce volume of fluid delivered by a fluid delivery element to tissue and/or reduce tissue contact of one or more ablation elements themselves (e.g. electrodes or hot fluid filled balloons). For those cases where the native diameter of the tissue varies substantially within the treatment zone, then a highly elastic or compliant balloon or other expandable element can be employed, such as a balloon or deployable cage which can be adjusted to achieve a wide range of operating diameters.

Treatment Modality 2: APPOSITION BETWEEN THE TREATMENT ASSEMBLY AND THE TARGET TISSUE IS ESTABLISHED BY CONTROLLING THE DIAMETER OF THE TARGET TISSUE. To initiate and/or increase tissue ablation by a treatment assembly, the diameter of the target tissue can be decreased in situ so as to cause one or more treatment assembly ablation elements (e.g. a fluid delivery element delivering ablative fluid, a hot fluid balloon delivering a thermal dose or an electrode delivering RF energy) to be closer to or to become in contact with the target tissue. To stop or otherwise decrease ablation of tissue, the diameter of tissue neighboring an ablation element can be increased in situ, so as to prevent or reduce volume of fluid delivered to tissue by a fluid delivery element and/or prevent or reduce contact of one or more ablative elements with tissue (e.g. target tissue and/or non-target tissue). The diameter of the tissue proximate an ablation element can be increased or decreased, independent of the treatment assembly diameter, by means of delivering and/or withdrawing a fluid, to and/or from a lumen surrounded by target tissue, such as by using standard gastrointestinal insufflation techniques. Typical insufflation fluids include but are not limited to: gases such as carbon dioxide or air; liquids such as water or saline solution; and combinations of these. The insufflation fluids can be introduced through the ablation device, through an endoscope such as an endoscope through which the ablation device is inserted, and/or via another device placed proximate the target tissue. Delivery of insufflation fluids can be performed to manipulate tissue, such as to distend and/or elongate tissue. Alternatively or additionally, delivery of insufflation fluids can be performed to move target tissue away from a treatment assembly, such as to stop transfer of energy to target tissue at the end of a thermal dose period as described hereabove. Removal of these insufflation fluids and/or the application of a vacuum or other negative pressure by one or more of the devices described hereabove, can be used to decrease the diameter of the target tissue, such as to bring the target tissue in close proximity to or contact with a treatment assembly. In this tissue diameter controlled approach, a balloon that can be maintained at a substantially constant diameter can be desirable, such as a substantially inelastic balloon such as a balloon with an elastic-limit.

Referring now to FIG. 1, a schematic view of a system for ablating or otherwise treating target tissue is illustrated, consistent with the present inventive concepts. System 10 is configured to treat target tissue TT. In the embodiment of FIG. 1, target tissue TT includes one or more tissue portions within a body lumen of a mammalian patient as has been described hereabove. In some embodiments, target tissue TT comprises a continuous or discontinuous circumferential segment of a duodenum, such as a volume of tissue comprising at least 50% of the duodenal mucosa. In some embodiments, target tissue TT comprises a treatment portion comprising duodenal mucosal tissue and a safety-margin portion comprising at least an innermost layer of the duodenal submucosa. System 10 can be configured to treat the duodenal mucosa while avoiding damage to duodenal adventitial tissue. System 10 can include one or more ablation devices, such as first ablation device 100 and second ablation device 100'. A supply of ablative fluid 331 is provided to at least ablation device 100 by agent delivery unit (ADU) 330. ADU 330 comprises one or more pumps or other fluid transport assemblies configured to deliver fluid, such as ablative fluid 331, to ablation device 100.

A device for delivering a second fluid, pumping assembly 340, can be included in system 10. Pumping assembly 340 can be configured to deliver one or more cooling, warming and/or other fluids. Pumping assembly 340 can be configured to provide fluid to modify the temperature of tissue and/or modify the temperature of one or more system 10 device components. Alternatively or additionally, pumping assembly 340 can be configured to deliver a reversing agent used to reverse, stop or minimize the ablative effects of an ablative fluid provided by ADU 330. Alternatively or additionally, pumping assembly 340 can be configured to extract or evacuate fluids, such as to extract or evacuate fluids from ablation device 100 and/or a body lumen into which ablation device 100 has been inserted. Pumping assembly 340 can be configured to recirculate one or more fluids through one or more tubes or lumens of device 100. A controlling interface, controller 310 can be operably attached to one or more components of system 10, such as ADU 330, pumping assembly 340 and/or another device or assembly of system 10, such as to control and/or monitor one or more parameters of the attached device or assembly.

As shown in FIG. 1, ablation device 100 includes coaxial shafts 111a and 111b. Shaft 111b has a distal end 112. Shafts 111a and 111b are sized and configured such that shaft 111a slidingly receives shaft 111b, such that they can be advanced and/or retracted in unison or independently. In some embodiments, device 100 comprises a flexible portion (e.g. a portion of shafts 111a and 111b including distal end 112) with a diameter less than 6 mm. In some embodiments, the flexible portion is configured to pass through a working channel of endoscope with a diameter of less than or equal to 6.0 mm, 4.2 mm, 3.8 mm, 3.2 mm or 2.8 mm. In some embodiments, device 100 comprises a shaft length of 100 cm or longer, or otherwise comprises a length sufficient to be orally and/or nasally inserted into a patient, and advanced to reach the esophagus, stomach, duodenum, jejunum or terminal ileum of that patient. In FIG. 1, shafts 111a and 111b have been inserted through a working channel (e.g. a 6 mm working channel), lumen 351, of endoscope 350, typically a gastrointestinal endoscope. Shafts 111a and/or 111b can be inserted over a standard interventional guidewire, such as guidewire 60 shown exiting distal end 112 of shaft 111b. In an alternative embodiment, shafts 111a and 111b are positioned in a side-by-side configuration, such as to be placed in two separate lumens of endoscope 350 or in two other non-coaxial locations. In some embodiments, one or both of shafts 111a or 111b can be inserted alongside endoscope 350 (i.e. not through lumen 351, traveling parallel with but external to endoscope 350). Shaft 111a and/or 111b can include deflection means configured to deflect and/or steer a distal portion of the shaft, such as via one or more proximal handle controlled pull wires that extend and are attached to the distal portion of the shaft, not shown but well known to those of skill in the art.

Ablation device 100 includes fluid delivery assembly 140 positioned on shaft 111a. Fluid delivery assembly 140 includes one or more fluid delivery elements, fluid delivery element 145. Fluid delivery element 145 can be positioned on, in, within or passing through one or more components of fluid delivery assembly 140, such as a balloon, cage, spline or other component as are described in detail herein. Fluid delivery element 145 is connected to one or more fluid delivery tubes, fluid delivery tube 141 which travels proximally through shaft 111a fluidly attaching to ADU 330 such that one or more ablative fluids can be delivered to the target tissue TT by fluid delivery element 145. Fluid delivery tube 141 can comprise one or more insulating layers configured to prevent transfer of heat into and/or out of fluid delivery tube 141. Fluid delivery tube 141 can include a surrounding lumen which receives a circulating fluid configured to provide an insulating, warming and/or cooling effect on fluid delivery tube 141 and/or any fluid contained within fluid delivery tube 141. Fluid delivery assembly 140 can be radially expandable, similar to expandable assembly 130 described herebelow. System 10 can be configured to allow expansion of fluid delivery assembly 140 to cause one or more fluid delivery elements 145 to be positioned at a fixed distance from the luminal wall of tubular tissue, such as at a fixed distance of at least 250 microns, at least 500 microns, or at least 1 mm from a tissue wall such as a duodenal wall. Fluid delivery assembly 140 can be configured to expand to a diameter less than the diameter of the target tissue TT. In addition to delivering ablative fluid 331 to treat tissue, fluid delivery assembly 140 can be configured in one or more various forms to modify, manipulate, measure and/or diagnose target tissue TT and/or other tubular or non-tubular tissue.

Fluid delivery tube 141 and/or another fluid delivery tube of system 10 can comprise one or more elongate hollow tubes, such as a hollow tube positioned within shaft 111a. Alternatively, fluid delivery tube 141 and/or another fluid delivery tube of system 10 can comprise a lumen within a shaft, such as a lumen within shaft 111a. In some embodiments, fluid delivery tube 141 and/or another fluid delivery tube of system 10 comprises a lumen and hollow tube that have been fluidly connected, such as in an end-to-end configuration. Ablative fluid 331 delivered by fluid delivery element 145 can be delivered directly to tissue, without any barriers between delivery element 145 and tissue, such that the ablative fluid 331 directly contacts the tissue. Fluid delivery tube 141 typically attaches to ADU 330 with one or more operator attachable fluid connection ports, such as a fluid connection port included in a handle positioned on the proximal end of shaft 111a, handle not shown but described herebelow in reference to FIG. 3A. Fluid delivery element 145 can include one or more fluid delivery elements selected from the group consisting of: nozzle such as a nozzle configured to deliver a cone or other shaped spray of fluid; opening; hole; slit; permeable membrane; misting element; vaporizer; and combinations of these. Fluid delivery element 145 can be fixed to shaft 111a, or it can be moveable, such as when fluid delivery element 145 is rotated and/or translated, prior to, during and/or after delivery of an ablative fluid, as is described in reference to FIGS. 8A-C herebelow. Fluid delivery element 145 can comprise multiple fluid delivery elements, such as multiple similar or dissimilar nozzles (e.g. multiple nozzles with similar or dissimilar spray patterns). Fluid delivery tube 141 can comprise one or more fluid delivery tubes, such as one or more flexible fluid delivery tubes. Fluid delivery tube 141 can comprise an insulating layer configured to minimize heat transfer into or out of fluid delivery tube 141. Fluid delivery tube 141 can include one or more valves, such as is described in reference to FIG. 4 herebelow, such as a valve used to regulate flow in either direction within fluid delivery tube 141.

In some embodiments, fluid delivery element 145 can be further configured to extract fluids, such as to extract previously administered ablative fluids from a body lumen. Alternatively or additionally, a fluid extraction element can be included, such as is described in reference to FIG. 7A herebelow. Fluid extraction can be performed prior to, during and or after delivery of one or more ablative fluids to target tissue TT.

Fluid delivery element 145 delivers ablative fluid 331 to target tissue TT to cause ablation of the target tissue. In some embodiments, agent delivery unit 330 does not modify the temperature of ablative fluid 331, such as when the temperature is modified by one or more components of device 100 or when ablative fluid 331 is delivered to target tissue TT without a temperature modification (e.g. at room or other ambient temperature). In some embodiments, fluids at elevated (e.g. above 60° C.) or reduced (e.g. below 0° C.) temperatures are delivered to ablate tissue via thermal ablation. Ablative fluid 331 can be provided at an ablative temperature, or one or more components or devices of system 10 can modify the ablative fluid 331 to be delivered at the ablative temperature, In some embodiments, at least one of the following adjust the temperature of ablative fluid 331: agent delivery assembly 330; fluid delivery element 145; fluid delivery assembly 140; a radially expandable element attached to shaft 111a and including fluid delivery element 145; a temperature modifying component mounted within shaft 111a; or a temperature modifying component mounted proximate fluid delivery element 145.

Agent delivery unit 330 can comprise multiple heat or cold sources used to modify the temperature of the ablative fluid 331. The heat or cold sources can be at a fixed temperature or they can be variable. In some embodiments, a first heat or cold source is at a fixed temperature and a second heat or cold source is at a variable temperature.

Ablative fluid 331 can comprise one or more liquids or gases that are delivered to target tissue TT at a temperature above or below a threshold that would ablate tissue. In some embodiments, ablative fluid 331 comprises steam, such as steam at a temperature of 100° C. or above. In some embodiments, ablative fluid 331 comprises a vaporized fluid at a temperature below 100° C., such as a vaporized fluid at a temperature between 70° C. and 90° C. In some embodiments, ablative fluid 331 comprises a gas, such as a gas between 60° C. and 99° C., such as a gas delivered to tissue at a temperature between 70° C. and 90° C. In some embodiments, ablative fluid 331 comprises a vaporized liquid, such as a vaporized liquid delivered to tissue at a temperature below 100° C., such as at a temperature between 70° C. and 90° C. In some embodiments, a cooling fluid is delivered, prior to, during and/or after the delivery of the ablative fluid, such as to precisely control target tissue ablation and avoid ablation of non-target tissue. The ablation provided by system 10 can comprise a non-desiccating or a desiccating ablation. In some embodiments, a non-desiccating ablation is performed for a first portion of target tissue TT and a desiccating ablation is performed for a second portion of target tissue TT. Non-desiccating ablations can be performed to treat over-lapping portions of target tissue TT, and/or to avoid creation of tissue debris if desired. Desiccating ablations can be performed to achieve a higher thermal gradient, to remove excess tissue, and/or to ablate rapidly if desired.

Alternatively or additionally, ablative fluid 331 can comprise one or more liquids or gases that cause tissue necrosis or otherwise treat target tissue TT as has been described hereabove, using one or more chemically active agents (e.g. ablation not primarily caused by delivery or removal of heat from tissue). In these embodiments, the agent can comprise an agent selected from the group consisting of: sclerotic agent; acid; base; saline; alcohol; carbon dioxide; nitrous oxide; nitrogen; acetic acid; glycerol; and combinations of these. In these embodiments, a counter-acting agent can be included, such as a counter-acting agent delivered by ablation device 100 or another device or component of system 10 that is used to neutralize, impede, reduce and/or limit tissue ablation caused by the delivery of a necrotic agent-based ablative fluid 331. The counter-acting agent can be delivered by the same component delivering ablative fluid 331 or another component. The counter-acting agent can comprise an agent selected from the group consisting of: anti-sclerotic agent; base; acid; buffer solution; saline; water; and combinations of these.

Agent delivery unit 330 and/or pumping assembly 340 can be configured to deliver a hot fluid to pre-heat one or more components of system 10. In some embodiments, the one or more components include a fluid delivery tube such as a tube within shaft 111a, a fluid delivery lumen such as a lumen within shaft 111a; shaft 111a; a fluid delivery element 145; and combinations of these. System 10 can be configured to pre-heat one or more components by circulating or recirculating hot fluid, such as a hot liquid or gas. In some embodiments, ablative fluid 331 comprises a heated liquid, and system 10 pre-heats one or more components with a hot gas. Alternatively or additionally, system 10 can comprise one or more insulators surrounding one or more components of device 100 or system 10, such as an insulator surrounding one or more fluid delivery tubes and/or shafts of system 10, and configured to prevent transfer of heat across (e.g. into or out of) the associated fluid delivery tube and/or shaft.

System 10 can be configured to deliver multiple volumes of ablative fluid 331 to tissue, such as multiple volumes comprising similar or dissimilar thermal energy amounts, and/or multiple volumes comprising similar or dissimilar necrotic agent amounts. In some embodiments, a first volume of ablative fluid 331 is delivered to a first portion of target tissue TT for a first time period, and a second volume of ablative fluid 331 is delivered to a second portion of target tissue TT for a second time period. The second volume of ablative fluid 331 delivered can occur immediately after the first volume is delivered, or after a time period in which no ablative fluid 331 is delivered. A second ablative fluid 331 volume can be delivered within 45 seconds of a first ablative fluid 331 volume, such as within 25 seconds, or within 10 seconds. A first ablative fluid 331 delivery can vary from a second ablative fluid 331 delivery by varying a parameter selected from the group consisting of: fluid delivery element used to deliver the volume; volume of fluid delivered, duration of fluid delivery; temperature profile of fluid delivery such as average or range of temperature delivered; type of fluid delivered; and combinations of these. System 10 can be configured to deliver multiple volumes of ablative fluid 331 to cause agitation of ablative fluid 331 within a body lumen, such as within a segment of the duodenum.

System 10 can be configured to provide ablative fluid 331 to target tissue TT using pulse-width modulated delivery. Pulse-width modulated delivery can include pulse-width modulation of a parameter selected from the group consisting of: temperature such as temperature of ablative fluid delivered; rate of delivery; volume of delivery; pH of delivery; and combinations of these. System 10 can be configured to maintain target tissue or other tissue below a threshold or within a temperature range, such as through the use of one or more sensors such as sensor 149 of fluid delivery assembly 140 or sensor 139 of expandable assembly 130, each described in detail herebelow. In some embodiments, tissue temperature is maintained below 100° C., such as between 60° C. and 90° C., or between 75° C. and 85° C. In some embodiments, system 10 is configured to maintain the temperature of target tissue TT at a setpoint and agent delivery unit 330 produces ablative fluid 331 above the setpoint temperature. The setpoint temperature can vary over time. System 10 can be configured to decrease the temperature of ablative fluid 331 delivered over time. In some embodiments, an ablative liquid and/or gas is delivered to cause the temperature of at least a portion of target tissue to rapidly rise to a setpoint (e.g. a setpoint between 60° C. and 75° C.). After the target tissue reaches the setpoint temperature, system 10 can deliver ablative fluid to maintain the setpoint temperature for an extended time period.

In some embodiments, agent delivery unit 330 is configured to heat or chill one or more fluids, such as one or more ablative fluids 331 or other fluids. In some embodiments, fluid delivery assembly 140 is configured to heat or chill one or more fluids. Applicable heating and cooling elements include but are not limited to heat exchangers, heating coils, peltier components, refrigeration assemblies, gas expansion coolers, and the like. Heating and cooling can be applied to a source of non-delivered fluid (e.g. a reservoir of ablative fluid 331), or to fluid that is withdrawn from device 100 (e.g. a recirculating fluid and/or a body extracted fluid such as recovered, previously delivered, ablative fluid). Agent delivery unit 330 and/or pumping assembly 340 can include one or more pumps configured to deliver and/or extract fluid at a particular flow rate, pressure, or other fluid delivery parameter. System 10 can be configured to deliver ablative fluid 331 at a sufficiently high temperature to ablate target tissue TT, after which a cooling fluid is delivered to remove thermal energy from target tissue TT and/or other tissue, such as cooling fluid delivered for a time period of at least 2 seconds, at least 5 seconds, at least 10 seconds or at least 20 seconds.

In some embodiments, ablative fluid 331 is delivered to target tissue TT for at least 1 second, such as for at least 3 seconds, such as to fully or partially treat at least a portion of target tissue TT. System 10 can be configured to deliver ablative fluid 331 to target tissue TT while avoiding one or more of: tissue desiccation; detachment of tissue particles; and combinations of these. Alternatively, system 10 can be configured to cause tissue desiccation and/or cause tissue particles to detach, such as to cause mucosal tissue to detach from a gastrointestinal wall.

Ablation device 100 further includes a radially expandable assembly, expandable assembly 130, mounted to shaft 111b. Expandable assembly 130 can be configured in one or more various forms to treat, modify, manipulate, measure and/or diagnose target tissue TT and/or other tubular tissue. Expandable assembly 130 can comprise an expandable element selected from the group consisting of: an inflatable balloon; a radially expandable stent or cage; an array of splines; one or more radially deployable arms; a spiral or other helical structure; a furlable structure such as a furlable sheet; an unfurlable structure such as an unfurlable sheet; a foldable structure such as a foldable sheet; an unfoldable structure such as an unfoldable sheet; and combinations of these. Expandable assembly 130 can be positioned distal to fluid delivery assembly 140 as shown in FIG. 1, or alternatively, expandable assembly 130 can be positioned proximal to fluid delivery assembly 140, such as when fluid delivery assembly 140 is mounted to shaft 111b and expandable assembly 130 is mounted to shaft 111a.

Expandable assembly 130 can be configured to seal a body lumen location, such as to create an occlusive barrier at a location within the duodenum or other location in the gastrointestinal tract. System 10 can be configured to cause a fluid or other seal comprising a seal selected from the group consisting of: a pressure seal; a cryogenically applied seal such as an ice ball seal; a vacuum seal; and combinations of these. In some embodiments, ablative fluid 331 is delivered to target tissue TT located proximal or distal to the occlusive barrier. System 10 can include multiple expandable assemblies configured to seal a body lumen location, such as a first expandable assembly which provides a seal at a proximal end of a segment of tubular tissue, and a second expandable assembly which provides a seal at a distal end of the tubular tissue segment. In some embodiments, ablative fluid 331 is delivered to target tissue TT located between the two sealed locations, such as between two locations of the duodenum, each duodenal location sealed by an expandable component or assembly of device 100. One or more expandable assemblies can be configured to occlude a first location of a body lumen, followed by subsequent occlusions of one or more different locations within the body lumen. System 10 can be configured to apply a vacuum between two occlusive elements, such as a vacuum applied by one or more fluid delivery elements 145, via one or more functional elements 138 and/or 148 (attached to expandable assembly 130 and fluid delivery assembly 140, respectively, each functional element described in detail herebelow) and/or by another device or component of system 10. Applied vacuum can be used to modify (e.g. change the shape of) the tubular tissue between the two occlusive elements and/or to increase the sealing force. In some embodiments, system 10 is configured to deploy a detached-balloon configured to occlude a body lumen, where the detached-balloon can later be punctured or otherwise deflated for physiologic removal by the gastrointestinal tract. Deployed balloons or other occlusive elements of system 10 can be positioned to protect tissue, such as to protect the ampulla of Vater and/or the pylorus from adverse effects of contact with ablative fluid 331.

In some embodiments, in addition to expandable assembly 130, fluid delivery assembly 140 can be radially expandable and/or include one or more radially expandable elements, such as those described hereabove in reference to expandable assembly 130. In some embodiments, fluid delivery assembly 140 is configured to radially expand and cause fluid delivery element 145 to move closer to and/or become in contact with target tissue TT. Expansion of fluid delivery assembly 140 can occur prior to, during and/or after delivery of ablative fluid to target tissue TT by fluid delivery element 145. Fluid delivery element 145 can be mounted on, within and/or inside of an expandable assembly, such as on, within and/or inside of an expandable balloon.

In some embodiments, expandable assembly 130 and/or fluid delivery assembly 140 comprise a length of at least 10 mm, such as a length between 10 mm and 40 mm, a length between 15 mm and 30 mm, or a length between 20 mm and 25 mm. In some embodiments, expandable assembly 130 and/or fluid delivery assembly 140 comprise a length less than or equal to 15 mm, such as when configured to treat curvilinear portions of the gastrointestinal tract. Multiple assemblies positioned on shafts 111*a* and/or 111*b* (e.g. between two and twenty fluid delivery assemblies and/or expandable assemblies), such as expandable assembly 130 and fluid delivery assembly 140, can be separated along a shaft by a distance less than or equal to 25 mm, such as a distance less than or equal to 20 mm. This separation distance can comprise the distance between a distal end of a tissue contacting portion of a first expandable element, and the neighboring proximal end of a tissue contacting portion of a second expandable element. In some embodiments, expandable assembly 130 comprises a length, and the separation distance between expandable assembly 130 and fluid delivery assembly 140 is less than or equal to the expandable assembly 130 length. In these embodiments, fluid delivery assembly 140 can comprise a similar length to that of expandable assembly 130, such as when both expandable assembly 130 and fluid delivery assembly 140 comprise an ablation element as is described herebelow.

Expandable assembly 130 can include another fluid delivery element, shown as nozzle 145', connected to one or more fluid delivery tubes, not shown but traveling proximally within shafts 111*b* and/or 111*a* and fluidly connected to agent delivery unit 330, such as via a connectable port on a handle of device 100. Nozzle 145' can be directed toward one or more device 100 components or assemblies, such as fluid delivery assembly 140 and fluid delivery element 145 as shown in FIG. 1. Nozzle 145' can be used to perform various functions such as the washing or removing of material from a device 100 component, or to cool or warm the temperature of a device 100 component. Alternatively or additionally, nozzle 145' can be directed toward or otherwise deliver fluid to tissue proximate device 100. Nozzle 145' can be configured to deliver a non-ablative fluid, such as a non-ablative fluid delivered to tissue or to a component of device 100. Non-ablative fluids can comprise a fluid selected from the group consisting of: a washing fluid; a counteracting fluid such as a fluid used to neutralize or otherwise reduce the effects of an ablative fluid such as an acid or sclerotic agent; a cooling fluid such as fluid for cooling tissue or a component of device 100; a warming fluid such as a fluid for warming tissue or a component of device 100; and combinations of these.

Expandable assembly 130 and/or fluid delivery assembly 140 can be configured to expand to a diameter of at least 15 mm, such as a diameter of at least 20 mm, 25 mm or at least 30 mm. Expandable assembly 130 and/or fluid delivery assembly 140 can be resiliently biased, such as in a radially expanded or radially compacted state. Expandable assembly 130 and/or fluid delivery assembly 140 can be expanded and/or compacted by a control shaft, not shown but described in detail in reference to FIG. 3B herebelow. Expandable assembly 130 and/or fluid delivery assembly 140 can be configured to achieve a round or non-round shape (e.g. a football shape) when expanded. Expandable assembly 130 and/or fluid delivery assembly 140 can approximate a tubular shape when expanded, such as a unidiameter or varying diameter tube shape. Expandable assembly 130 and/or fluid delivery assembly 140 can be configured to un-fold to a radially expanded state, or to fold to a radially compacted state.

Expandable assembly 130 can comprise at least one functional element 138, and fluid delivery assembly 140 can comprise at least one functional element 148. Functional elements 138 and/or 148 can be elements selected from the group consisting of: an ablation element such as one or more electrodes configured to deliver electrical energy such as radiofrequency (RF) energy; a sensor; a transducer; a fluid delivery element such as a needle, a fluid jet, a permeable membrane and/or an exit port; a heating element; a cooling element; and combinations of these.

In some embodiments, expandable assembly 130 is configured to ablate tissue, such as via functional element 138. Functional element 138 of expandable assembly 130 can comprise one or more ablation elements, such as those described in applicant's co-pending International PCT Application Serial Number PCT/US12/21739, entitled "Devices and Methods for the Treatment of Tissue", filed Jan. 18, 2012, the contents of which is incorporated herein by reference in its entirety. In some embodiments, functional element 138 comprises an ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these. In these embodiments, either or both expandable assembly 130 or fluid delivery assembly 140 can be used to ablate target tissue TT. ADU 330 or another component of system 10 can be configured to deliver RF or other energy to functional element 138. System 10 can include ground pad 70, such as a standard RF energy delivery ground pad typically placed on the patient's back, such that ADU 330 can supply RF energy to functional element 138 and/or any other electrodes of system 10 in monopolar, bipolar and/or combined monopolar-bipolar energy delivery modes.

In some embodiments, expandable assembly 130 is configured to perform at least one non-ablative function. Expandable assembly 130 can be configured to occlude or partially occlude a lumen surrounded by tissue, such as a lumen of the gastrointestinal tract to be occluded during an insufflation procedure. Expandable assembly 130 can be configured to manipulate tissue, such as to linearize and/or distend gastrointestinal tissue by frictionally engaging (e.g. when expanded) and applying forces to the tissue (e.g. by advancing and/or retracting shaft 111*b*). In some embodiments, one or more expandable assemblies 130 can perform a function, singly or in combination, selected from the group consisting of: linearizing curvilinear tissue; distending tissue; expanding tissue; occluding a body lumen; and combinations of these. Expandable assembly 130 can be configured to test and/or diagnose tissue, such as when expandable assembly 130 is used to measure a diameter of tubular tissue into which it has been inserted. Diameter measurements can be performed in various ways, including but not limited to: injection of a radiopaque fluid into assembly 130 and fluoroscopic measurement of the injected fluid; controlled inflation of assembly 130 to a pressure whose level corresponds to a luminal diameter; and combinations of these. In some embodiments, device 100 includes an expandable assembly that can be expanded with one or more control rods, such as expandable assembly 130 of FIG. 3B. A diametric measurement of tubular tissue can be performed by precision measurement of control rod advancement (e.g. when control rod position correlates to expandable assembly diameter). Alternatively or additionally, tubular tissue diameter can be determined by measuring the diameter of an expandable assembly when it initially, circumferentially contacts the wall of tubular tissue (e.g. when a specific radial force is achieved and/or when contact is observed such as using fluoroscopy or ultrasound visualization devices). In some embodiments, system 10 includes a separate device, such as a balloon catheter, used to perform a diameter measurement. One or more energy delivery or other ablation parameters can be adjusted based on the measured diameter of target tissue TT and/or a target tissue portion.

In some embodiments, expandable assembly 130 is configured to expand or otherwise modify one or more layers of tissue, such as when functional element 138 comprises a needle and/or water jet configured to expand submucosal tissue of the gastrointestinal tract, such as is described in applicant's U.S. Provisional Application Ser. No. 61/635, 810, entitled "Tissue Expansion Devices, Systems and Methods", filed Apr. 19, 2012, the contents of which is incorporated herein by reference in its entirety. Alternatively or additionally, system 10 can include a separate tissue expansion device, tissue expansion device 200. Tissue expansion can greatly alleviate the need for precision of treatment, such as precision of ablative fluid 331 and/or energy delivery, due to the increased size (e.g. increased depth) of the target tissue TT including an associated safety-margin of tissue to which treatment causes no significant adverse event (e.g. an expanded submucosal layer prior to a mucosal layer ablation).

Figure 3A:
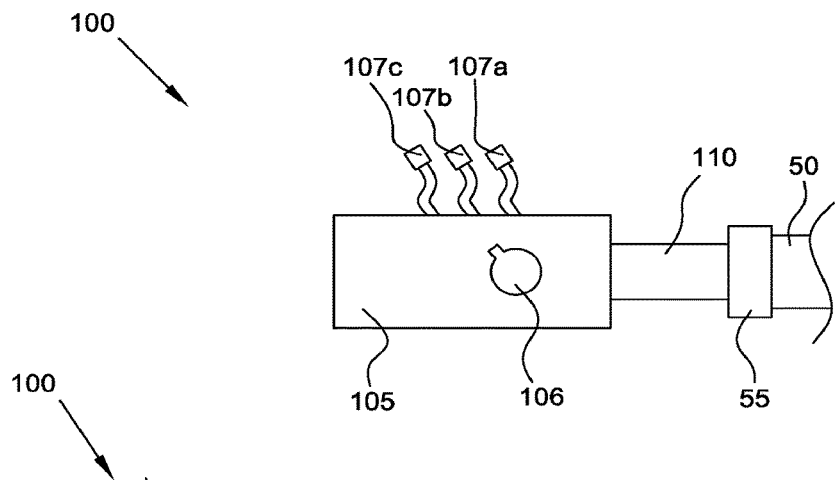
FIGS. 3A and 3B are side views of the proximal and distal portions, respectively, of an ablation device comprising multiple fluid delivery tubes, consistent with the present inventive concepts.
Figure 3B:
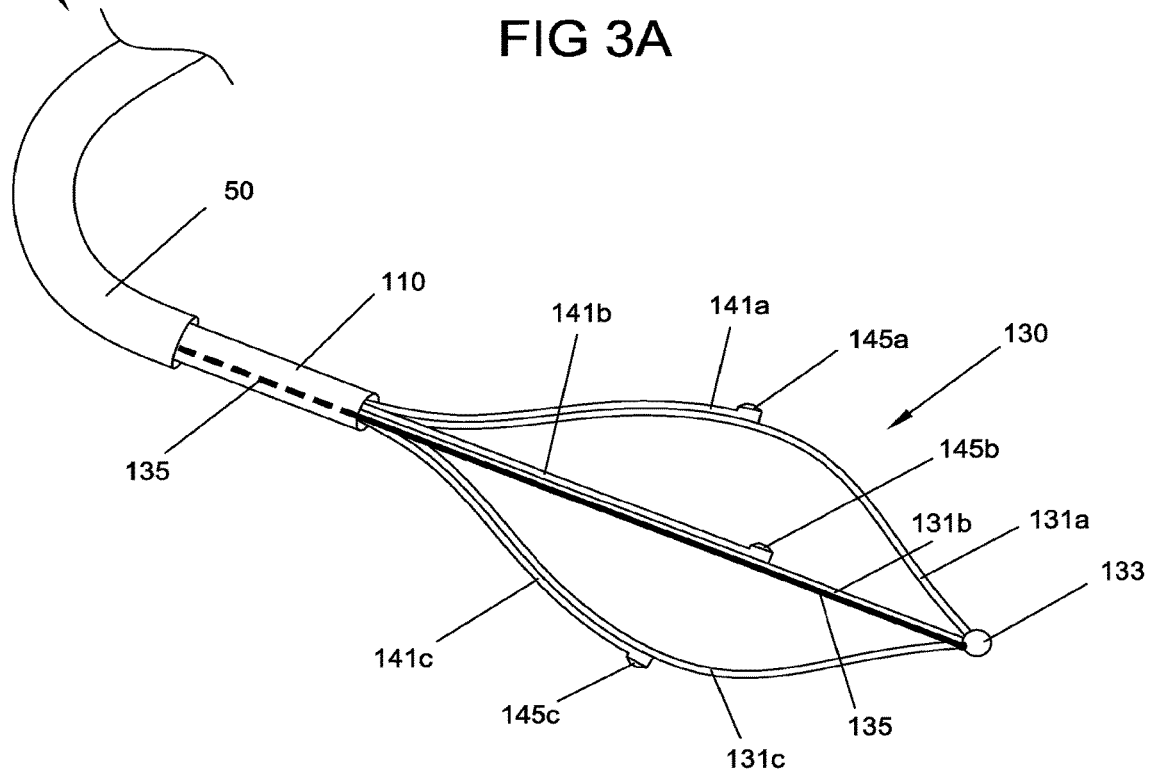

In some embodiments, expandable assembly 130 and/or fluid delivery assembly 140 comprise a shape that can be adjusted by an operator, such as via a control rod as is described in reference to FIG. 3B herebelow. In some embodiments, the shape of the arrangement of fluid delivery element 145 (e.g. arrangement between two separate fluid delivery elements of fluid delivery element 145) can be operator modified by adjusting the shape of fluid delivery assembly 140.

Fluid delivery element 145 is configured to deliver one or more ablative fluids to ablate various thickness of gastrointestinal tissue, such as at least the innermost 500 microns of duodenal tissue, or at least the innermost 1 mm of duodenal tissue. In some embodiments, fluid delivery element 145 can be configured to ablate a thickness of at least 600 microns, at least 1 mm or at least 1.25 mm, such as when treating the mucosa of the stomach. Fluid delivery element 145 can be configured to deliver one or more ablative fluids to ablate a volume of tissue comprising a surface area and a depth, where the ratio of magnitude of the depth to the magnitude of the surface area is less than or equal to 1 to 100 (e.g. less than 1%), or less than or equal to 1 to 1000 (e.g. less than 0.1%). In some embodiments, expandable assembly 130 and/or fluid delivery assembly 140 are configured to be in a relatively rigid state, such as during delivery of ablative fluid 331 to target tissue TT.

Fluid delivery element 145 and/or other fluid delivery or other ablation elements of the present inventive concepts can be arranged in various patterns, such that ADU 330 can deliver one or more ablative fluids in associated patterns.

Fluid delivery element 145 and/or other ablation elements of the present inventive concepts can be arranged in an array of elements, such as a circumferential or linear array of elements. The circumferential array can comprise a partial circumferential array of fluid delivery elements 145, such as an array covering approximately 45° to 300° of circumferential area. Partial circumferential arrays of fluid delivery elements 145 can treat a first target tissue portion and a second target tissue portion in two sequential steps, where the array is rotated between ablative fluid deliveries. The circumferential array can comprise a full 360° array of fluid delivery elements 145, such that a full circumferential volume of target tissue TT can be treated in a single or multiple deliveries of ablative fluid that do not require repositioning of fluid delivery assembly 140. In some embodiments, less than 360° of tubular tissue is treated, such as by delivering ablative fluid 331 to a circumferential portion of tissue comprising less than or equal to a 350°, or between 300° and 350°, such as to prevent a full circumferential scar from being created.

Two or more fluid delivery elements 145 can be arranged in a helical array. In some embodiments, at least three, four or five fluid delivery elements independently deliver (e.g. via independent fluid delivery tubes 141) one or more similar or dissimilar ablative fluids, simultaneously or sequentially, as supplied by ADU 330.

Figure 4:
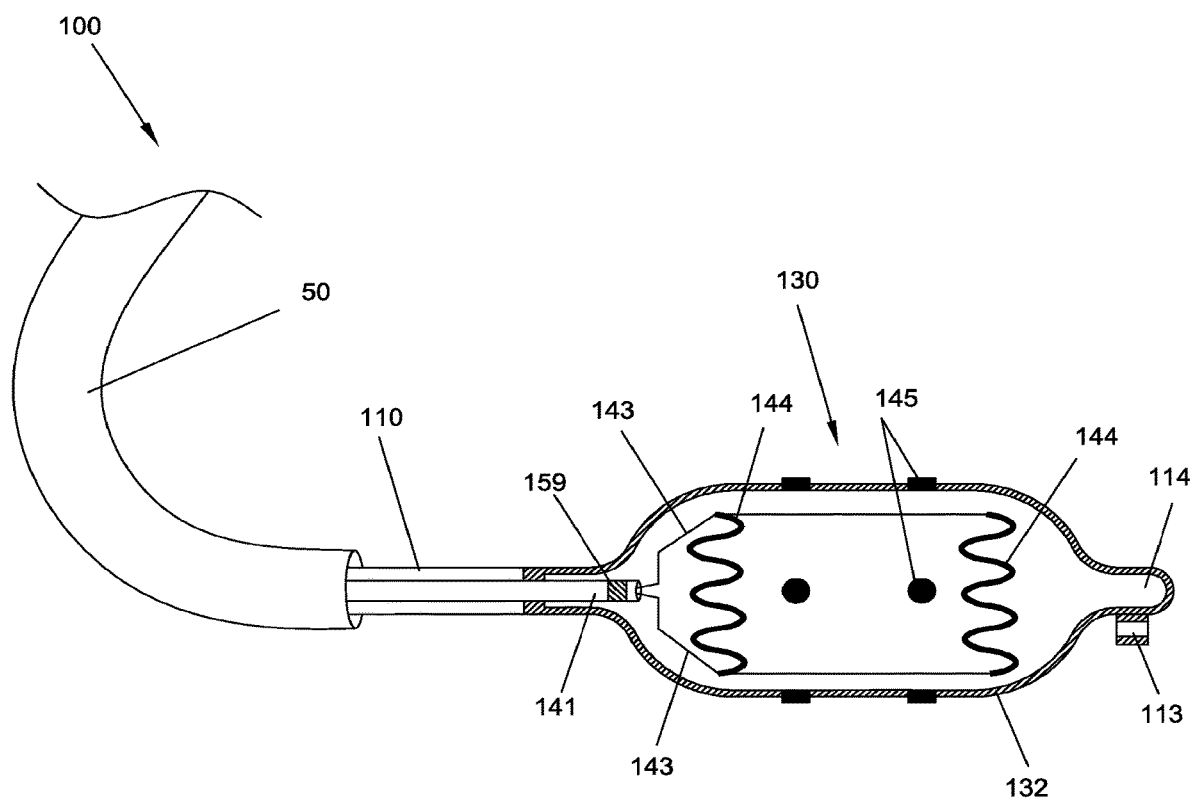
FIG. 4 is a side sectional view of the distal portion of an ablation device comprising a distal heating element, consistent with the present inventive concepts.

In some embodiments, ADU 330 or other device or component of system 10 provides electrical or other energy to a component of ablation device 100, such as electrical energy provided to a heating coil in a distal portion of device 100, such as is described in reference to FIG. 4 herebelow. ADU 330 or other device or component of system 10 can provide energy such as electrical energy to one or more of functional element 138 and/or functional element 148 such as when either comprises a transducer or other powered component.

Fluid delivery element 145 can comprise one or more fluid delivery elements configured to deliver ablative fluid 331 along a sufficient length of tissue to treat substantially the entire length of the duodenum simultaneously and/or without having to reposition ablation device 100, such as when fluid delivery element 145 comprises an array of fluid delivery elements positioned along substantially the entire length of the duodenum or when fluid delivery element 145 comprises at least one fluid delivery element configured to rotate and/or translate along substantially the entire length of the duodenum. Fluid delivery element 145 and/or other ablation elements of the present inventive concepts can be configured to treat at least 50% of the entire length of the duodenum simultaneously and/or without having to reposition ablation device 100. Fluid delivery element 145 and/or other ablation elements of the present inventive concepts can be configured to treat a first portion of target tissue TT followed by a second portion of target issue TT. The first and second treated tissue portions can be overlapping and they can have non-parallel central axes (e.g. tissue portions in a curved portion of the duodenum). Three or more target tissue portions can be treated, such as to cumulatively ablate at least 30% or at least 50% of the duodenal mucosa.

In some embodiments, expandable assembly 130 and/or fluid delivery assembly 140 comprise inflatable or otherwise expandable balloons, such as one or more of: a compliant balloon; a non-compliant balloon; a balloon with a pressure threshold; a balloon with compliant and non-compliant portions; a balloon with a fluid entry port; a balloon with a fluid exit port; and combinations of these. In some embodiments, expandable assembly 130 and/or fluid delivery assembly 140 comprise a balloon which is fluidly attached to an inflation tube, such as an inflation tube which travels proximally through shaft 111a and/or 111b and is attached to an inflation port, not shown but typically attached to a handle on the proximal end of ablation device 100.

In some embodiments, functional element 138 of expandable assembly 130 comprises an abrasive element configured for abrading target tissue, such as an abrasive element attached to a balloon or expandable cage.

Shafts 111a and 111b can include one or more lumens passing therethrough, and can comprise wires and/or optical fibers for transfer of data and/or energy such as RF energy to functional element 138 and/or 148. Shafts 111b and/or 111a can comprise one or more shafts, such as one or more concentric shafts configured to deliver and/or recirculate hot and/or cold fluid through expandable assembly 130 and/or fluid delivery assembly 140, respectively. In some embodiments, a heated fluid is used to pre-heat one or more ablation device 100 components and/or to deliver a bolus of hot fluid energy, each as described in applicant's U.S. Provisional Application Ser. No. 61/603,475, entitled "Heat Ablation Systems, Devices and Methods for the Treatment of Tissue", filed Feb. 27, 2012, the contents of which is incorporated herein by reference in its entirety. Device 100 can comprise multiple expandable assemblies 130, such as a first expandable assembly positioned proximal to fluid delivery assembly 140 (not shown) and a second expandable assembly positioned distal to fluid delivery assembly 140 (assembly 130 as shown in FIG. 1).

Figure 2:
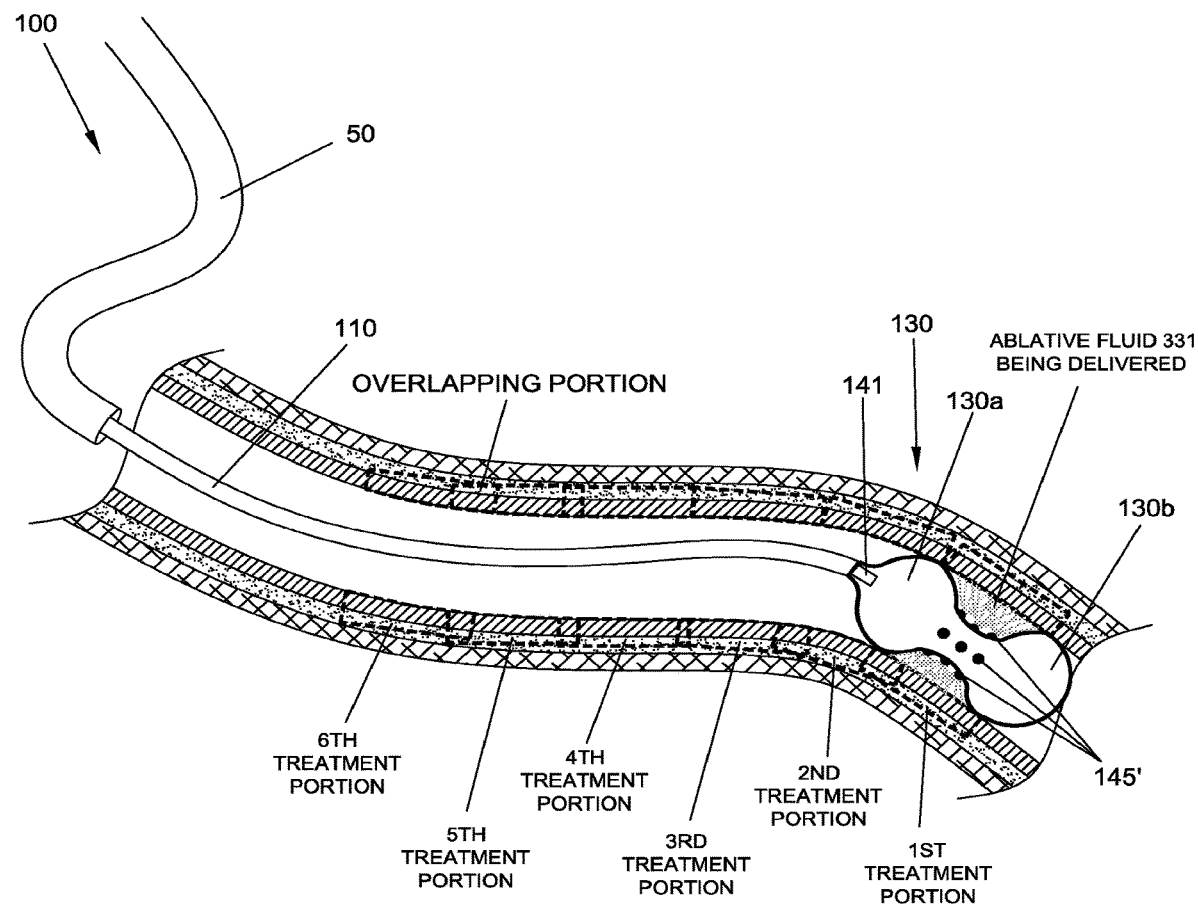
FIG. 2 is a side sectional view of the distal portion of an ablation device inserted into a curvilinear section of duodenum, consistent with the present inventive concepts.

Fluid delivery assembly 140 and/or expandable assembly 130 can be configured to ablate tissue or otherwise perform a function while positioned in a curved segment of the gastrointestinal tract, such as is described in reference to FIG. 2 herebelow.

System 10 is configured to ablate or otherwise treat target tissue TT, such as duodenal mucosal tissue, while avoiding damaging non-target tissue, such as the gastrointestinal adventitia. Target tissue TT can include at least a portion of safety-margin tissue comprising tissue whose ablation causes minimal or no adverse effect to the patient, such as sub-mucosal tissue of the gastrointestinal tract. Target tissue TT can comprise one or more portions of tissue that are treated simultaneously or sequentially. In some embodiments, the target tissue TT comprises the majority of the length of the duodenal mucosa, such as at least 30% or at least 50% of the duodenal mucosa. In some embodiments, the target tissue TT comprises at least 90% of the duodenal mucosa, or at least 95% of the duodenal mucosa. In some embodiments, the target tissue TT includes the full mucosal thickness of at least a portion of duodenal tissue, as well as at least the innermost 100 microns of submucosal duodenal tissue, or at least the innermost 200 microns of submucosal duodenal tissue. The target tissue TT can include at least one of ileal mucosal tissue or gastric mucosal tissue.

Endoscope 350 can be a standard endoscope, such as a standard gastrointestinal endoscope, or a customized endoscope, such as an endoscope including sensor 353 configured to provide information related to the tissue treatment of the present inventive concepts. Endoscope 350 can include camera 352, such as a visible light, ultrasound and/or other visualization device used by the operator of system 10 prior to, during and/or after the treatment of target tissue TT, such as during insertion and/or removal of endoscope 350 and/or shafts 111a and 111b of ablation device 100. Camera 352 can provide direct visualization of internal body spaces and tissue, such as the internal organs of the gastrointestinal tract. Endoscope 350 can be coupled with or otherwise include a guidewire, e.g. guidewire 60, such as to allow insertion of endoscope 350 into the jejunum and/or advancement of ablation device 100.

System 10 can be constructed and arranged to perform insufflation of a body lumen, such as insufflation of a segment of the gastrointestinal tract. The body lumen can be pressurized, such as by using one or more standard insufflation techniques. Insufflation fluid can be introduced through second lumen 354 of endoscope 350. Second lumen 354 travels proximally and connects to a source of insufflation liquid and/or gas, such as pumping assembly 340, and typically a source of air, carbon dioxide, water and/or saline. Alternatively or additionally, insufflation fluid can be delivered by ablation device 100, such as through shaft 111a and/or 111b, and/or through a port in expandable assembly 130 and/or fluid delivery assembly 140, such as when functional elements 138 and/or 148, respectively, comprise a fluid delivery port attached to a source of insufflation liquid and/or gas (e.g. provided by pumping assembly 340). Alternatively or additionally, a separate device configured to be inserted through endoscope 350 and/or to be positioned alongside endoscope 350, can have one or more lumens configured to deliver the insufflation fluid. System 10 can include one or more occlusive elements and/or devices, such as expandable assembly 130, fluid delivery assembly 140 and/or another expandable device configured to radially expand such as to fully or partially occlude a body lumen, such that insufflation pressure can be achieved and/or maintained over time (e.g. reduce or prevent undesired migration of insufflation fluid). The one or more occlusive elements and/or devices can be positioned proximal to and/or distal to the luminal segment to be insufflated.

Pumping assembly 340 and/or agent delivery unit 330 can be configured to remove fluid from a body lumen such as a segment of the gastrointestinal tract. Removed fluids include but are not limited to: ablative fluid 331; condensate of ablative fluid 331; insufflation fluids; excess bodily fluids; chyme; digestive fluids; gas; and combinations of these. Fluids can be removed prior to, during and/or after delivery of the ablative fluid 331 to the target tissue TT. Pumping assembly 340 and/or agent delivery unit 330 can be configured to apply a vacuum, such as to remove fluid via at least one fluid delivery element 145, an outflow drain such as drain 155 of FIG. 7A, or other fluid extraction port of system 10. In some embodiments, extracted fluids are recycled, such as for subsequent delivery by at least one fluid delivery element 145 to target tissue TT.

Pumping assembly 340 and/or ADU 330 can be configured to deliver one or more gases (e.g. carbon dioxide, nitrogen, nitrous oxide and/or air) to at least one fluid delivery element 145 or another gas delivering component of system 10. In some embodiments, at least one fluid delivery element 145 comprises a gas jet nozzle configured to deliver gas to target tissue, such as a gas that has been processed to remove moisture or otherwise be dry (e.g. less than the dew point of air, or at a relative humidity less than 20% or less than 10%). In some embodiments, system 10 is configured to deliver gas to cause agitation of ablative fluid previously delivered within a body lumen. System 10 can be configured to deliver dry or other gas to move ablative fluid in a body lumen. The delivered gas can comprises a cooling gas, such as a gas below 37° C., a gas between 0° C. and 7° C. such as a gas between 2° C. and 7° C., and/or a gas at approximately 4° C. System 10 can deliver cooling gas for a time period of at least 10 seconds, at least 20 seconds or at least 30 seconds. In some embodiments, system 10 delivers cooling gas at a temperature less than 0° C. for a time period less than or equal to 20 seconds, less than or 10 seconds, or less than or equal to 5 seconds. In some embodiments, system 10 is configured to deliver gas at a temperature at or above 42° C., such as to remove moisture or otherwise dry a tissue wall of the gastrointestinal tract. System 10 can be configured to deliver carbon dioxide gas.

Functional element 138 and/or functional element 148 can comprise a sensor. In some embodiments, functional element 138, functional element 148, sensor 353 and/or another sensor of system 10, such as sensor 139 positioned on expandable assembly 130 and/or sensor 149 positioned on fluid delivery assembly 140, can comprise a sensor selected from the group consisting of: temperature sensors such as thermocouples, thermistors, resistance temperature detectors and optical temperature sensors; strain gauges; impedance sensors such as tissue impedance sensors; pressure sensors; blood sensors; optical sensors such as light sensors; sound sensors such as ultrasound sensors; electromagnetic sensors such as electromagnetic field sensors; visual sensors; and combinations of these. The sensors can be configured to provide information to one or more components of system 10, such as to controller 310 and/or ADU 330, such as to monitor the treatment of target tissue TT and/or to treat target tissue TT in a closed loop configuration. Ablative fluid delivery from ADU 330 can be initiated, stopped and/or modified based on one or more sensor readings. In one embodiment, an algorithm of controller 310 and/or ADU 330 processes one or more sensor signals to modify the amount of ablative fluid delivered, rate of ablative fluid delivery, energy delivered, power of energy delivered, voltage of energy delivered, current of energy delivered and/or temperature of ablative fluid or energy delivery.

Fluid delivery assembly 140 can include gravimetric sensor 149a. In some embodiments, gravimetric sensor 149a comprises an accelerometer or other sensor configured to provide a signal representing the orientation of fluid delivery assembly 140 and/or fluid delivery element 145 as it relates to the force of earth's gravity. The signal provided by gravimetric sensor 149a can provide information for manual and/or automated control of ablative fluid delivery direction. In some embodiments, gravimetric orientation of device 100 is provided to an operator, such as via a screen on controller 310. In some embodiments, the signal from gravimetric sensor 149a is recorded by controller 310, such as to adjust the spray pattern delivered by fluid delivery assembly 140 and/or fluid delivery element 145. Based on a signal from gravimetric sensor 149a, fluid delivery element 145 and/or shaft 11a can be positioned to deliver ablative fluid 331 in upward and/or side-ways (i.e. horizontal) directions, such as to allow delivered fluid to flow across the walls of a lumen in a downward direction. Controller 310 can be configured to adjust the flow pattern of ablative fluid delivery by adjusting the rotation and/or translation of fluid delivery assembly 140 (e.g. by creating an asymmetric movement). Controller 310 can be configured to adjust the flow pattern of ablative fluid delivery by adjusting which of multiple fluid delivery elements 145 deliver ablative fluid (e.g. by turning on one or more electronic fluid valves) or by adjusting a nozzle direction or nozzle flow path geometry of fluid delivery element 145 (e.g. when fluid delivery element 145 comprises a rotatable nozzle and/or a nozzle with an adjustable orifice). In some embodiments, controller 310 utilizes a signal from gravimetric sensor 149a to manipulate one or more fluid delivery elements 145 to deliver fluid in a relatively upward direction. In some embodiments, system 10 includes a fluid removal element, such as a fluid delivery element 145 configured to remove fluid or an outflow drain (e.g. outflow drain 155 of FIG. 7A), and the fluid removal element is gravimetrically oriented by a signal provided by gravimetric sensor 149a.

A sensor such as a chemical detection sensor can be included, such as to confirm proper apposition of expandable assembly 130 and/or fluid delivery assembly 140. In this configuration, a chemical sensor such as a carbon dioxide sensor can be placed distal to expandable assembly 130 and/or fluid delivery assembly 140, and a fluid such as carbon dioxide gas is introduced proximal to the expandable assembly 130 and/or fluid delivery assembly 140. Detection of the introduced fluid can indicate inadequate apposition of expandable assembly 130 and/or fluid delivery assembly 140, such as to prevent inadequate transfer of ablative fluid or energy to target tissue TT and/or prevent inadequate measurement, modification, manipulation and/or diagnosis of target tissue TT.

Functional element 138, functional element 148, sensor 353 and/or another sensor of system 10 can be a sensor configured to provide information related to the tissue treatment performed by fluid delivery assembly 140 and/or expandable assembly 130, such as a visual sensor mounted to fluid delivery assembly 140 and/or expandable assembly 130 that is configured to differentiate tissue types that are proximate fluid delivery assembly 140 and/or expandable assembly, such as to differentiate mucosal and submucosal tissue. Applicable visible sensors include but are not limited to: visible light camera; infrared camera; CT Scanner; MRI; and combinations of these. In some embodiments, ablative fluid delivered by fluid delivery element 145 and/or energy delivered by other ablation elements of system 10 is based on one or more signals from the visible sensor, such as a sensor providing a signal correlating to tissue color wherein the ablative fluid delivered is modified based on a tissue color change. Functional elements 138 and/or 148 can comprise a sensor configured to provide information related to the tissue treatment performed by fluid delivery assembly 140 and/or expandable assembly 130, such as a temperature sensor configured to monitor the temperature of treatment provided by fluid delivery assembly 140 and/or expandable assembly 130 and/or tissue proximate fluid delivery assembly 140 and/or expandable assembly 130. Functional elements 138 and/or 148 can comprise multiple temperature sensors, such as multiple temperature sensors positioned on fluid delivery assembly 140 and/or expandable assembly 130, respectively, with a spacing of at least one sensor per square centimeter. Ablative fluid 331 and/or other ablative energy delivered by ADU 330 can be based on signals recorded by the multiple temperature sensors.

Functional element 138 and/or functional element 148 can comprise a transducer. In these and other embodiments, functional element 138, functional element 148, and/or another transducer of system 10 can be a transducer selected from the group consisting of: a heat generating element; a drug delivery element such as an iontophoretic drug delivery element; a magnetic field generator; an ultrasound wave generator such as a piezo crystal; a light producing element such as a visible and/or infrared light emitting diode; and combinations of these.

ADU 330 is configured to deliver ablative fluid 331 to fluid delivery element 145 and one or more other fluid delivery elements of system 10. ADU 330 can include one or more ablative liquids or gases as has been described hereabove. In some embodiments, ADU 330 is configured to deliver multiple, different ablative fluids, such as to a single fluid delivery element 145 or different fluid delivery elements. The different ablative fluids can be delivered independent or mixed, and they can be delivered simultaneously or sequentially to two or more fluid delivery elements. Ablative fluid delivery can comprise continuous and/or pulsed fluid delivery, and can be delivered in a closed-loop fashion as described hereabove. Fluid delivery parameters such as volume, rate, temperature, pressure and pH can be held relatively constant or they can be varied by ADU 330. Ablative fluid delivery can be varied from a first tissue location (e.g. a first portion of target tissue) to a second location (e.g. a second portion of target tissue), such as a decrease in ablation level (e.g. decrease in volume, rate, temperature, pressure and/or acidity) from a first treated location to a second treated location when the second treated location is thinner than the first treated location. Alternatively or additionally, ablative fluid delivery can be varied during a single application of ablative fluid to a single tissue location, such as by adjusting one or more ablative fluid delivery parameters during a continuous energy delivery.

In some embodiments, ADU 330 or another device of component of system 10 is configured to deliver a visualizable material, such as a visualizable material included in ablative fluid 331 and delivered to one or more fluid delivery elements 145. In some embodiments, visualizable material is included in ablative fluid 331 to assist in the treatment of tissue, such as to assess the status of tissue ablation. In some embodiments, the visualizable material is selected from the group consisting of: radiopaque agent; ultrasonically visible material; magnetically visible material; and combinations of these. An imaging device of system 10, such as imaging device 410, can be used to create an image of the visualizable material during and/or after delivery of the visualizable material.

In some embodiments, ADU 330 or another device of component of system 10 is configured to deliver abrasive particles, such as abrasive particles included in ablative fluid 331 delivered to one or more fluid delivery elements 145. In some embodiments, visualizable material is also included in ablative fluid 331 to assist in the treatment of tissue, such as to improve ablation caused by a mechanical abrasion treatment.

In some embodiments, ADU 330 is configured to also deliver at least RF energy, and system 10 includes ground pad 70 configured to be attached to the patient (e.g. on the back of the patient), such that RF energy can be delivered in monopolar delivery mode to one or more electrodes of ablation catheter 100 or another device of system 10. Alternatively or additionally, ADU 330 can be configured to deliver energy in a bipolar RF mode, such as bipolar energy delivered between any two electrodes of ablation device 100 or other device of system 10. Alternatively or additionally, ADU 330 can be configured to deliver energy in a combined monopolar-bipolar mode.

ADU 330 can be configured to deliver RF and/or other forms of energy to one or more ablation elements of fluid delivery assembly 140 and/or expandable assembly 130. In some embodiments, ADU 330 delivers energy selected from the group consisting of: RF energy; microwave energy; plasma energy; ultrasound energy; light energy; and combinations of these. Energy can be continuous and/or pulsed, and can be delivered in a closed-loop fashion as described hereabove. Energy delivery parameters such as power, voltage, current and frequency can be held relatively constant or they can be varied by ADU 330. Energy delivery can be varied from a first tissue location (e.g. a first portion of target tissue TT) to a second location (e.g. a second portion of target tissue TT), such as a decrease in energy from a first treated location to a second treated location when the second treated location is thinner than the first treated location. Alternatively or additionally, energy delivery can be varied during a single application of energy to a single tissue location, such as by adjusting one or more energy delivery parameters during a continuous energy delivery.

System 10 can be further configured to deliver and extract one or more fluids from fluid delivery assembly 140 and/or expandable assembly 130, such as to pre-heat fluid delivery assembly 140 and/or expandable assembly 130 and/or to deliver heat energy to target tissue TT via the delivered fluids. In one embodiment, pumping assembly 340 and/or ADU 330 are configured to deliver one or more supplies of hot fluid, such as hot water or saline when fluid delivery assembly 140 and/or expandable assembly 130 comprises a balloon positioned at the end of one or more fluid delivery tubes, such as fluid delivery tube 141, such as is described in applicant's U.S. Provisional Application Ser. No. 61/603,475, entitled "Heat Ablation Systems, Devices and Methods for the Treatment of Tissue", filed Feb. 27, 2012, the contents of which is incorporated herein by reference in its entirety. In these embodiments, pumping assembly 340 and/or ADU 330 typically includes one or more fluid pumps, such as one or more peristaltic, displacement and/or other fluid pumps; as well as one or more heat exchangers and/or other fluid heating elements internal and/or external to device 100. Pumping assembly 340 and/or ADU 330 can be configured to rapidly deliver and/or withdraw fluid to and/or from fluid delivery assembly 140 and/or expandable assembly 130 via one or more fluid transport means. Fluid transport means can include a pump configured to deliver fluid at a flow rate of at least 50 ml/min and/or a pump and/or vacuum source configured to remove fluid at a flow rate of at least 50 ml/min. In some embodiments, system 10 is configured to deliver fluid, such as a liquid, at a flow rate of at least 500 ml/min, or at least 750 ml/min. A pump and/or vacuum source can be configured to continuously exchange hot fluid and/or to perform a negative pressure priming event to remove fluid from one or more fluid pathways of device 100. Pumping assembly 340, ADU 330 and/or ablation device 100 can include one or more valves in the fluid delivery and/or fluid withdrawal pathways or one or more other valves in the fluid pathway within fluid delivery assembly 140 and/or expandable assembly 130. Valves can be configured to control entry of fluid into an area and/or to maintain pressure of fluid within an area. Valves can be used to cause the transition from a heating fluid being delivered, such as a fluid of 90° C. maintained in a treatment assembly for approximately 12 seconds, to a cooling fluid being delivered, such as a fluid between 4° C. and 10° C. maintained in the treatment assembly for approximately 30 to 60 seconds. Typical valves include but are not limited to: duck-bill valves; slit valves; electronically activated valves; pressure relief valves; and combinations of these. Pumping assembly 340 and/or ADU 330 can be configured to rapidly inflate and/or deflate fluid delivery assembly 140 and/or expandable assembly 130. Pumping assembly 340 and/or ADU 330 can be configured to purge the fluid pathways of device 100 with a gas such as air, such as to remove cold and/or hot fluid from device 100 and/or to remove gas bubbles from device 100.

ADU 330, fluid delivery element 145 and/or other components of system 10 can be configured to treat target tissue TT with a non-desiccating ablation, such as by avoiding tissue temperatures above 100° C., avoiding the creation of steam, or otherwise avoiding deleterious desiccation of tissue. System 10 can be configured to minimize heat production in the outermost 50% of a mucosal layer, such as to ablate the outermost 50% of the mucosal layer via thermal conduction. System 10 can be configured to minimize heat production in the outermost 80% of a mucosal layer, such as to ablate the outermost 80% of the mucosal layer via thermal conduction. System 10 can be configured to maximize the flow of current, such as through the innermost 50% of a mucosal layer, or through the innermost 20% of a mucosal layer. In some embodiments, system 10 can be configured to avoid detachment of tissue particles.

ADU 330, fluid delivery element 145 and/or other components of system 10 can be configured to deliver ablative fluid 331 or other energy to target tissue TT such that the temperature of at least a portion of the target tissue TT rises rapidly, such as at a rate of greater than or equal to 17.5° C. per second. The ablative fluid 331 or other energy can be delivered to cause the temperature of at least a portion of the target tissue TT to reach a setpoint temperature between 60° C. and 90° C., such as a setpoint temperature between 70° C. and 85° C. System 10 can be configured to cause the target tissue TT to elevate to a setpoint temperature and maintain that setpoint temperature, such as by maintaining the setpoint temperature for a time period between 2 and 40 seconds. In these embodiments, the setpoint temperature can be between 60° C. and 90° C., such as a setpoint temperature between 75° C. and 85° C. that is maintained for between 15 and 25 seconds. In some embodiments, after a setpoint temperature is achieved and/or maintained, the ablative fluid 331 or other energy delivered causes a decrease in temperature over time, such as to match a tissue response of the target tissue TT.

Controller 310 typically includes a graphical user interface configured to allow one or more operators of system 10 to perform one or more functions such as entering of one or more system input parameters and visualizing and/or recording of one or more system output parameters. Controller 310 typically includes one or more user input components (e.g. touch screens, keyboards, joysticks, electronic mice and the like), and one or more user output components (e.g. video displays; liquid crystal displays; alphanumeric displays; audio devices such as speakers; lights such as light emitting diodes; tactile alerts such as assemblies including a vibrating mechanism; and the like). Typical system input parameters include but are not limited to: type of ablative fluid to be delivered; rate of ablative fluid to be delivered; volume of ablative fluid to be delivered; type of energy to be delivered such as RF energy, thermal energy and/or mechanical energy; quantity of energy to be delivered such as a cumulative number of joules of energy to be delivered and/or peak amount of energy to be delivered; types and levels of combinations of energies to be delivered; energy delivery duration; pulse width modulation percentage of energy delivered; temperature of a fluid to be delivered to a expandable element such as a balloon; temperature of a cooling fluid to be delivered; flow rate of a hot fluid to be delivered; volume of a hot fluid to be delivered; number of reciprocating motions for an energy delivery element to transverse; temperature for a treatment assembly such as target temperature and/or maximum temperature; insufflation pressure; insufflation duration; and combinations of these. System input parameters can include information based on patient anatomy and/or conditions such as pre-procedural and/or peri-procedural parameters selected from the group consisting of: mucosal density and/or thickness; mucosal "lift" off of submucosa after a submucosal injection; longitudinal location of target tissue within the GI tract; and combinations of these. Typical system output parameters include but are not limited to: temperature information such as tissue and/or treatment assembly temperature information; pressure information such as balloon pressure information and/or insufflation pressure information; force information such as level of force applied to tissue information; patient information such as patient physiologic information recorded by one or more sensors; and combinations of these.

Controller 310 and/or one or more other components of system 10 can include an electronics module, such as an electronics module including a processor, memory, software, and the like. Controller 310 is typically configured to allow an operator to initiate, modify and cease treatment of target tissue TT by the various components of system 10, such as by controlling ADU 330 and/or pumping assembly 340. Controller 310 can be configured to modify one or more ablative fluid delivery parameters, such as a parameter selected from the group consisting of: type of ablative fluid to be delivered; rate of ablative fluid to be delivered; volume of ablative fluid to be delivered; pulse width modulation on-time and/or off-time; a time division multiplexing parameter; and combinations of these. Controller 310 can be configured for manual control, so that the operator first initiates the ablative fluid delivery, then allows the fluid delivery element 145 and/or another associated fluid delivery element to deliver ablative fluid 331 to target tissue TT for some time period, after which the operator terminates the ablative fluid delivery.

Controller 310 and ADU 330 can be configured to deliver ablative fluid 331 in constant, varied, continuous and discontinuous fluid delivery profiles. Pulse width modulation and/or time division multiplexing (TDM) can be incorporated to achieve precision of ablative treatment, such as to ensure ablation of target tissue TT while leaving non-target tissue intact.

In some embodiments, where system 10 is further configured to perform hot fluid ablation, controller 310 can be configured to adjust the temperature, flow rate and/or pressure of fluid delivered to a balloon, such as when expandable assembly 130 comprises a balloon. Controller 310 can be configured to initiate insufflation and/or to adjust insufflation pressure. Controller 310 can be configured to deliver ablative fluid 331 and/or energy (e.g. from pumping assembly 340 and/or ADU 330) in a closed-loop fashion, such as by modifying one or more tissue treatment parameters based on signals from one or more sensors of system 10, such as those described hereabove. Controller 310 can be programmable such as to allow an operator to store predetermined system settings for future use.

Controller 310 can comprise an impedance monitoring assembly, such as an impedance monitoring assembly that receives impedance information from one or both of functional element 138 of expandable assembly 130 and/or functionally element 148 of fluid delivery assembly 140. ADU 330 can deliver RF energy to one or more electrodes of system 10 based on the impedance determined by the impedance monitoring assembly.

Numerous embodiments of the systems, methods and devices for treating target tissue TT described hereabove include controlling and/or monitoring the change in target tissue temperature to cause its ablation, such as a temperature increase above 43° C., typically above 60° C., 70° C. or 80° C., to ablate at least a portion of the target tissue TT. One or more cooling fluids can be delivered to limit or otherwise control ablation, such as to prevent damage to non-target tissue, such as the duodenal adventitia. Pumping assembly 340 can be configured to deliver a fluid to tissue and/or a component and/or assembly of system 10, such as to warm and/or cool the tissue, component and/or assembly. Pumping assembly 340 can be configured to deliver a cooling fluid to a luminal wall such as the duodenal wall, such as prior to a delivery of RF energy, during a delivery of RF energy and/or after a delivery of RF energy. In some embodiments, a chilled fluid is used to cool tissue prior to, during and/or after a high temperature ablation of tissue. System 10 can be configured to deliver a fluid at a temperature below 37° C. or below 20° C. The chilled fluid can be delivered at a temperature between 0° C. and 7° C., and in some embodiments, the chilled fluid is delivered at a temperature less than 0° C. System 10 to can be configured to deliver chilled fluid at multiple temperatures to target tissue TT and/or other tissue. System 10 can be configured to deliver a first chilled fluid at a first temperature for a first time period, followed by a second chilled fluid delivered at a second temperature for a second time period. The first and second chilled fluids can be similar or dissimilar fluids, such as similar or dissimilar liquids and/or gases. In some embodiments, the first chilled fluid is colder than the second chilled fluid, such as a first chilled fluid delivered at approximately 4° C. for a time period of approximately 5 seconds, followed by fluid delivered at a higher temperature (e.g. a temperature between 10° C. and 37° C.) for a time period of at least 5 seconds. The chilled fluid can be delivered between ablation of a first portion of target tissue and a second portion of target tissue and/or between delivery of a first volume of ablative fluid 331 and a second volume of ablative fluid 331 (e.g. to the same or different tissue), such as to remove residual heat remaining after the first treatment. The cooling fluid can be delivered through functional element 138 of expandable assembly 130 and/or functional element 148 of fluid delivery assembly 140, such as when functional elements 138 and/or 148 comprises a fluid delivery element such as a nozzle, an exit hole, a slit, or a permeable membrane. The cooling fluid can be supplied to expandable assembly 130 and/or fluid delivery assembly 140, such as when expandable assembly 130 and/or fluid delivery assembly 140 comprises a balloon configured to contact tissue. Alternatively or additionally, pumping assembly 340 can be fluidly attached to another component of ablation device 100 and/or system 10, the attached component not shown but configured to deliver fluid to tissue and/or a component of system 10 such as to add and/or absorb heat. Pumping assembly 340 can comprise a cryogenic source used to deliver fluids at low temperatures, such as temperatures below 0° C. Typical fluids delivered include but are not limited to: liquids such as water and/or saline; gases such as carbon dioxide, nitrogen, nitrous oxide and/or air; and combinations of these.

Pumping assembly 340 can include a desiccant and/or drying assembly configured to dehydrate or otherwise remove moisture from one or more delivered gases prior to their delivery. In some embodiments, fluid provided to one or more fluid delivery elements 145 has its temperature modified by a component in a distal portion of device 100, such as a heating or cooling element integral or proximal to fluid delivery element 145 (e.g. a peltier cooling element, an expanded gas cooling assembly, or a heating coil integral to fluid delivery element 145). Alternatively or additionally, system 10 can include a component configured to directly contact tissue in order to cool or warm tissue. In some embodiments, radially expandable assembly 130, functional element 138 and/or functional element 148 can be configured to contact tissue and remove and/or add heat from the contacted tissue.

In some embodiments, ablative fluid 331 delivered by fluid delivery element 145 comprises steam, and system 10 is configured to deliver three volumes of steam to target tissue. System 10 can be configured to deliver one or more deliveries of cooling fluid, prior to, during and/or after the delivery of the three volumes of steam, such as to maintain the target tissue at a temperature between 70° C. and 90° C.

System 10 can include a motion control mechanism, such as motion transfer assembly 320. Motion transfer assembly 320 can be configured to rotate, translate and/or otherwise move a component of system 10, such as to move one or more of fluid delivery assembly 140, fluid delivery element 145 and/or expandable assembly 130. In some embodiments, motion transfer assembly 320 is configured to rotate and/or axially translate shafts 111a and/or 111b such that fluid delivery assembly 140 and/or expandable assembly 130, respectively, are rotated and/or translated. Motion transfer assembly 320 can be configured to rotate fluid delivery assembly 140 and/or expandable assembly 130 independently or in unison. Motion transfer assembly 320 can be configured to translate fluid delivery assembly 140 as ablative fluid 331 is being delivered by fluid delivery element 145. In some embodiments, contiguous tissue portions are treated by device 100 continuously as motion transfer assembly 320 causes fluid delivery assembly 140 to translate at a rate of at least 10 cm per minute, or at a rate of least 20 cm per minute. In some embodiments, fluid delivery assembly 140 is manually translated, such as at a rate of at least 10 cm per minute, or at least 20 cm per minute. Motion transfer assembly 320 can be configured to translate fluid delivery assembly 140 between a first ablative fluid delivery and a second ablative fluid delivery. Motion transfer assembly 320 can include one or more rotational and/or linear drive assemblies, such as those including rotational motors, magnetic, lead screw and/or other linear actuators, and the like which are operably connected to shaft 111a and/or 111b. Shafts 111a and/or 111b are constructed with sufficient column strength and/or torque transfer properties to sufficiently rotate and/or translate fluid delivery assembly 140 and/or expandable assembly 130, respectively. Motion transfer assembly 320 can be in communication with controller 310, such as to activate, adjust and/or otherwise control motion transfer assembly 320 and thus the motion of fluid delivery assembly 140 and/or expandable assembly 130. Motion transfer assembly 320 can be manually driven and/or automatically (e.g. motor) driven. Alternatively or additionally, motion transfer assembly 320 can be used to advance and/or retract fluid delivery assembly 140 and/or expandable assembly 130 from a first position to treat a first portion of target tissue, to a second position to treat a second portion of target tissue. In this embodiment, repositioning of fluid delivery assembly 140 and/or expandable assembly 130 can be configured to provide overlapping treatment, such as the overlapping treatment described in reference to FIG. 2 herebelow.

Fluid delivery assembly 140 or another component or assembly of system 10 can be configured to agitate the ablative fluid 331, such as an agitation that is performed prior to, during and/or after ablative fluid 331 exits one or more fluid delivery elements 145. Agitation can be performed to create a uniform dispersion of ablative fluid 331 and/or other fluids delivered by system 10. Agitation can be performed to create turbulence of one or more delivered fluids, such as turbulence of the fluid while in a segment of the gastrointestinal tract. System 10 can be configured to cause agitation by rapidly evacuating fluids from or rapidly delivering fluids to a segment of gastrointestinal lumen. Fluid evacuation can be performed through one or more fluid delivery elements 145, or through a separate outflow drain, such as drain 155 of FIG. 7A. In some embodiments, system 10 is configured to vary the distance between a fluid delivery port (e.g. fluid delivery element 145) and a fluid extraction or evacuation port (e.g. drain 155 of FIG. 7A) to cause agitation of fluid within a body lumen. Agitation can be performed by one or more devices or components of system 10 by varying the rate of fluid delivery, such as by varying the rate of ablative fluid 331 delivery from one or more fluid delivery elements 145. System 10 can be configured to cause agitation by moving one or more fluid delivery elements 145, such as a movement selected from the group consisting of: rotation about an axis of GI tract; translation along an axis of GI tract; advancement toward GI luminal wall; retraction from GI luminal wall; and combinations of these. System 10 can be configured to cause fluid agitation by rapidly expanding and/or contracting fluid delivery assembly 140 and/or radially expandable assembly 130. System 10 can include two or more radially expandable elements configured to occlude a tissue lumen, such as a component of fluid delivery assembly 140, expandable assembly 130 and/or another radially expandable assembly of system 10 configured to occlude a tissue lumen. The two or more radially expandable, occlusive elements can be moved towards each other or away from each other, such as via motion transfer assembly 320, to cause agitation of fluid within the lumen between the two occlusive elements. Agitation can be performed after a fluid is dispensed, such as by rotating and/or translating expandable assembly 130 or otherwise causing air or other fluid flow within a segment of the gastrointestinal tract containing the delivered ablative fluid 331. In some embodiments, functional element 138 and/or 148 comprise an air movement device such as a rotating fan blade configured to cause agitation of ablative fluid 331 within the gastrointestinal tract. In some embodiments, system 10 is configured to perform a non-desiccating treatment of tissue and system 10 comprises an agitating assembly configured to improve ablation of duodenal mucosa. In these embodiments, ablative fluid delivery can comprise delivery of one or more volumes of fluid over a period of at least three seconds to at least a portion of target tissue TT.

System 10 can include a second ablation device 100' configured to treat target tissue TT. Second ablation device 100' can be of similar or dissimilar construction to ablation device 100. In some embodiments, second ablation device 100' comprises an expandable assembly with a different diameter than expandable assembly 130 of device 100. In some embodiments, second ablation device 100' comprises a fluid delivery element with a different construction and arrangement (e.g. a different spray pattern or a different ablative fluid delivered) than fluid delivery element 145 of ablation device 100. In some embodiments, second ablation device 100' comprises a device selected from the group consisting of: hot fluid filled balloon device; RF energy delivery device; vapor ablation device; cryoablation device; laser ablation device; ultrasound ablation device; mechanical abrasion device; and combinations of these. Second ablation device 100' can comprise at least one ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these.

System 10 can further include one or more imaging devices, such as imaging device 410. Imaging device 410 can be configured to be inserted into the patient and can comprise a visual light camera; an ultrasound imager; an optical coherence domain reflectometry (OCDR) imager; and/or an optical coherence tomography (OCT) imager, such as when integral to, attached to, contained within and/or proximate to shaft 111a and/or 111b. Imaging device 410 can be inserted through a separate working channel of endoscope 350, lumen not shown. In one embodiment, imaging device 410 is an ultrasound transducer connected to a shaft, not shown but surrounded by shaft 111a and typically rotated and/or translated to create a multi-dimensional image of the area surrounding imaging device 410. Alternatively or additionally, imaging device 410 can be external to the patient, such as an imaging device selected from the group consisting of: an X-ray; a fluoroscope; an ultrasound image; an MRI; a PET Scanner; a near-infrared imaging camera; a fluorescence imaging camera; and combinations of these. Image and other information provided by imaging device 410 can be provided to an operator of system 10 and/or used by a component of system 10, such as controller 310, to automatically or semi-automatically adjust one or more system parameters such as one or more energy delivery parameters.

System 10 can further include protective element 191, configured to be positioned proximate tissue to prevent damage to certain tissue during ablative fluid delivery, other energy delivery and/or other tissue treatment event. Protective element 191 can comprise an element selected from the group consisting of: a deployable and/or recoverable cap and/or covering; an advanceable and/or retractable protective sheath; and combinations of these. Protective element 191 can be delivered with endoscope 350 and/or another elongate device such that element 191 can be placed over or otherwise positioned to protect non-target tissue, such as tissue selected from the group consisting of: ampulla of Vater; bile duct; pancreas; pylorus; muscularis externae; serosa; and combinations of these. In a typical embodiment, protective element 191 is removed within 24 hours of placement, such as by being removed during the procedure after treatment of the target tissue TT. System 10 can be configured to identify non-target tissue, such as via a camera used to identify the ampulla of Vater.

System 10 can be configured to prevent excessive distension of the duodenum such as would cause tearing of the serosa. In some embodiments, system 10 is configured such that all tissue contacting components and/or fluids delivered by system 10 maintain forces applied on a gastrointestinal wall below 1.0 psi, such as less than 0.5 psi, or less than 0.3 psi. System 10 can be configured to avoid or otherwise minimize damage to the muscularis layer of the gastrointestinal tract, such as by controlling pressure of ablative fluid 331 delivery (e.g. via use of a pressure regulator) and/or by minimizing trauma imparted by one or more components of system 10.

System 10 can further include one or more pharmaceutical and/or other agents 420, such as an agent configured for systemic and/or local delivery to a patient. These agents can be delivered pre-procedurally, peri-procedurally and/or post-procedurally. The agents can be configured to improve healing, such as agents selected from the group consisting of: antibiotics, steroids, mucosal cytoprotective agents such as sucralfate, proton pump inhibitors and/or other acid blocking drugs; and combinations of these. Alternative or in addition to these agents, pre-procedural and/or post-procedural diets can be employed. Pre-procedural diets can include food intake that is low in carbohydrates and/or low in calories. Post-procedural diets can include food intake that comprise a total liquid diet and/or a diet that is low in calories and/or low in carbohydrates.

In some embodiments, system 10 does not include a chronically implanted component and/or device, only body inserted devices that are removed at the end of the clinical procedure or shortly thereafter, such as devices removed within 8 hours of insertion, within 24 hours of insertion and/or within one week of insertion. In an alternative embodiment, implant 192 can be included. Implant 192 can comprise at least one of: a stent; a sleeve; and/or a drug delivery device such as a coated stent, a coated sleeve and/or an implanted pump. Implant 192 can be inserted into the patient and remain implanted for a period of at least one month, at least 6 months or at least 1 year.

Any of the components of system 10 can include a coating, such as a lubricous coating. In some embodiments, fluid delivery elements 145 and/or radially expandable elements such as balloons include a lubricous or other material property modifying coating. In some embodiments, a radially expandable fluid delivery assembly 140 and/or expandable assembly 130 comprise a hydrophilic coating configured to disperse or otherwise move ablative fluid 331.

Each of the components and/or devices of system 10 can be removably attached to another component, particularly ablation device 100, controller 310, ADU 330, motion transfer assembly 320, pumping assembly 340, ground pad 70, endoscope 350 and/or second ablation device 100'. Typical attachment means include but are not limited to mechanical or electromechanical connectors providing an electrical, optical and/or fluidic connection between the attached components.

Referring now to FIG. 2, a side sectional view of the distal portion of an ablation device inserted into a curvilinear section of duodenum is illustrated, consistent with the present inventive concepts. Ablation device 100 comprises shaft 110, a relatively flexible, biocompatible, elongate structure configured for insertion into a body lumen such as the duodenal lumen shown. Shaft 110 is typically connected to a handle on its proximal end, not shown but configured to allow an operator to advance, retract and otherwise manipulate or control ablation device 100. Ablation device 100 can be configured for delivery over a guidewire, via a lumen from a proximal portion to a distal portion, or via a rapid exchange sidecar in the distal portion of the device (lumen and sidecar not shown but described hereebelow). Expandable assembly 130 comprises two expandable assemblies 130a and 130b, which are each mounted to a distal portion of shaft 110. Expandable assemblies 130a and 130b can comprise a balloon or other expandable element as has been described hereabove, and can be configured to be expanded in unison or independently. Shaft 110 is shown inserted through introducer 50 which can comprise an endoscope, sheath, or other body introduction device. Positioned between expandable assemblies 130a and 130b are multiple nozzles 145', mounted to a mid portion of expandable assembly 130. In some embodiments, expandable assembly 130 comprises a single, dog-bone shaped balloon with nozzles 145' mounted on the central portion and configured to deliver fluid to a region between distal and proximal enlarged ends of the dog-bone shaped balloon as shown in FIG. 2. Alternatively, expandable assembly 130a and 130b can comprise two different, independently inflatable balloons. Nozzles 145' can be positioned in partial or full circumferential arrangement, such that they deliver a pattern of ablative fluid toward a partial or full circumferential segment of target tissue. Expandable assembly 130 has been positioned in a distal portion of duodenal tissue, such as a section that has had a segment of submucosal tissue expanded (expansion not shown). Expandable assembly 130 has been radially expanded such as to contact the mucosal surface of the duodenum at a 1.sup.st target tissue or treatment portion, which is distal to a series of target tissue or treatment portions comprising sequential target tissue portions 2 through 6 as shown in FIG. 2. Nozzles 145' are in fluid communication with fluid delivery tube 141 which travels proximally within shaft 110 to a proximal handle, not shown but configured to fluidly attach tube 141 to a source of ablative fluid, such as agent delivery unit 330 of FIG. 1. Nozzles 145' can comprise similar or dissimilar nozzles, such as nozzles with similar or dissimilar spray patterns. In some embodiments, one or more nozzles 145' is attached to a fluid delivery tube different than a different one or more nozzles 145', such as to permit independent delivery of two or more similar or dissimilar ablative fluids.

Expandable assembly 130 is sized to allow positioning in the curved segments of a gastrointestinal segment such as a curved segment of the duodenum, such that expandable assembly 130 can be expanded to fully contact the mucosal wall without exerting undesired force onto tissue. In some embodiments, expandable assembly 130 comprises a length less than or equal to 30 mm, such as less than or equal to 25 mm, less than or equal to 20 mm or less than or equal to 15 mm. After application of the ablative fluid, expandable assembly 130 will be repositioned to the 2.sup.nd target tissue portion, just proximal to the 1.sup.st target tissue portion, with or without contracting assembly 130 prior to the repositioning. Subsequently, second energy delivery can be performed. The steps of repositioning and delivering energy are repeated until target tissue portions 3, 4, 5 and 6 have been treated, typically greater than 50% of the length of the duodenal mucosa, or greater than 90% of the duodenal mucosal length. Alternatively or additionally, other tissue can be treated, such as has been described hereabove.

Target tissue portions 1 through 6 typically include common or overlapping tissue portions, such as is shown in FIG. 2. While the embodiment of FIG. 2 shows six target tissue portions being treated, more or less segments can be treated. Treatments (e.g. ablative fluid deliveries) are typically done in a contiguous manner (e.g. 1.sup.st portion followed by 2.sup.nd portion, followed by 3.sup.rd portion, etc), however any order can be performed. In some embodiments, multiple contiguous or discontiguous tissue portions are treated simultaneously. In some embodiments, contiguous tissue portions are treated by device 100 continuously, as expandable assembly 130 is translated proximally and/or distally, such as via a manual or automated retraction and/or advancement, respectively, as has been described in reference to FIG. 1 hereabove. In some embodiments, ablative fluid 331 is delivered as expandable assembly 130 translates at a rate of at least 10 cm per minute.

Referring now to FIGS. 3A and 3B, side views of the proximal and distal portions, respectively, of an ablation device comprising individual fluid delivery tubes is illustrated, consistent with the present inventive concepts. Ablation device 100 comprises shaft 110, a relatively flexible, biocompatible, elongate structure configured for insertion into a body lumen such as a duodenal lumen. Shaft 110 is connected to handle 105 on its proximal end. Handle 105 is configured to allow an operator to advance, retract and otherwise manipulate or control ablation device 100. Ablation device 100 can be configured for delivery over a guidewire, via a lumen from a proximal portion to a distal portion, or via a rapid exchange sidecar in the distal portion of the device (lumen and sidecar not shown but described hereebelow). Device 100 can include or otherwise be inserted through a body introduction device, such as introducer 50 shown, typically an endoscope, sheath, or other body introduction device including port 55 on its proximal end.

Expandable assembly 130 comprises an array of two or more splines, such as the three splines 131a-c shown. Splines 131a-c can be arranged in a symmetric pattern (e.g. three splines spaced 120° apart) or in an asymmetric arrangement. Expandable assembly 130 comprises one or more fluid delivery elements, such as fluid delivery elements 145*a-c* shown attached to splines 131*a-c* and fluidly attached to three independent fluid delivery tubes, tubes 141*a-c* as shown. Fluid delivery tubes 141*a-c* travel proximally through shaft 110 and fluidly attach to ports 107*a-c*, respectively. Ports 107*a-c* are configured to fluidly attach to one or more sources of ablative fluid, such as agent delivery unit 330 of FIG. 1. Ports 107*a-c* and fluid delivery tubes 141*a-c* are configured to allow delivery of individual ablative fluids to fluid delivery elements 145*a-c* respectively. In alternative embodiments, fluid delivery elements 145*a-c* are attached to two or less fluid delivery tubes, such as a single fluid delivery tube.

Fluid delivery elements 145*a-c* and other multiple fluid delivery element embodiments can comprise fluid delivery elements of similar or dissimilar construction. In some embodiments, a first fluid delivery element, such as fluid delivery element 145*a* of FIG. 3B, is attached to a source of ablative fluid, and a second fluid delivery element, such as fluid delivery element 145*b* of FIG. 3B, is attached to a source of non-ablative fluid, such as cooling fluid, counteracting fluid, washing fluid, or other non-ablative fluid as has been described hereabove. The non-ablative fluid can be delivered to perform a function selected from the group consisting of: limit the area of tissue ablated; stop ablation of a portion of tissue; reduce ablation of a portion of tissue; wash tissue; cool a device component; wash a device component; and combinations of these.

Splines 131*a-c* can be biased, such as a stainless steel or nickel titanium alloy spline elastically biased in a linear (not shown) or curvilinear (as shown in FIG. 3B) geometry. Splines 131*a-c* are connected at their distal end to hub 133, typically with a rounded or otherwise atraumatic distal surface. Device 100 can include control rod 135, which is attached on its distal end to hub 133 and/or the distal ends of one or more splines 131*a-c*. Control rod 135 can be operably attached on its proximal end to control 106 of handle 105, such as a control connected to a cam or other motion transfer assembly configured to cause advancement and/or retraction of control rod 135 as control 106 is rotated. Advancement of rod 135 causes expandable assembly 130 to radially compact (e.g. to pull away from a luminal tissue wall and/or prepare for capture within a lumen of introducer 50), while retraction of rod 135 causes expandable assembly 130 to radially expand (e.g. to move toward a luminal tissue wall after having been positioned at a portion of target tissue to be treated). In alternative embodiments, rod 135 is attached to the proximal end of one or more splines 131*a-c*, such that advancement of rod 135 causes assembly 130 to expand and retraction of rod 135 causes assembly 130 to compact. A diametric measurement of tubular tissue can be performed by precision measurement of control rod 135 advancement (e.g. when control rod position correlates to expandable assembly diameter). Alternatively or additionally, tubular tissue diameter can be determined by measuring the diameter of expandable assembly 130 when it initially, circumferentially contacts the wall of tubular tissue (e.g. when a specific radial force is achieved and/or when contact is observed such as using fluoroscopy or ultrasound visualization devices).

Fluid delivery elements 145*a-c* shown in FIG. 3B are configured to deliver one or more ablative fluids to target tissue, such as duodenal wall tissue, while minimizing trauma to non-target tissue, such as duodenal adventitial tissue, as has been described in detail in reference to FIG. 1 hereabove. Ablative fluid can be delivered in one or more sequential or simultaneous steps, as has been described in reference to FIG. 2 hereabove.

Referring now to FIG. 4, a side view of the distal portion of an ablation device comprising a distal heating element is illustrated, consistent with the present inventive concepts. Ablation device 100 comprises shaft 110, a relatively flexible, biocompatible, elongate structure configured for insertion into a body lumen such as a duodenal lumen. Shaft 110 is typically connected to a handle on its proximal end, not shown but configured to allow an operator to advance, retract and otherwise manipulate or control ablation device 100. Ablation device 100 can be configured for delivery over a guidewire, via a lumen from a proximal portion to a distal portion, or via a rapid exchange sidecar in the distal portion of device 100 such as sidecar 113 shown. Device 100 can include or otherwise be inserted through a body introduction device, such as introducer 50 shown, typically an endoscope, sheath, or other body introduction device.

Expandable assembly 130 comprises an inflatable balloon 132 positioned on the end of shaft 110 as shown. The distal end of device 100 includes tip 114, attached to the distal end of balloon 132 and including a profile configured for atraumatic insertion and advancement of device 100 within a body lumen such as the gastrointestinal tract. Mounted on, in and/or within the walls of balloon 132 are multiple fluid delivery elements 145, such as similar or dissimilar nozzles, openings, slits or other fluid delivery elements as have been described herein. Fluid delivery elements 145 are positioned to deliver ablative fluid to a full or partial circumferential segment of tubular tissue, such as a segment of the duodenum. Fluid delivery tube 141 is in fluid communication with balloon 132 such that ablative fluid delivered through fluid delivery tube 141, as has been described hereabove, causes balloon 132 to expand and ablative fluid to be delivered through fluid delivery elements 145. Balloon 132 is configured such that negative pressure applied through fluid delivery tube 141 causes balloon 132 to collapse.

Expandable assembly 130 further includes one or more heating elements, such as coils 144 which are attached to wires 143 as shown. Wires 143 travel proximally through shaft 110 to a handle, not shown but configured to attach to a supply of electrical energy such as that provided by ADU 330 or another device or component of system 10 of FIG. 1. Coils 144 can be configured to elevate the temperature of one or more fluids contained within balloon 132, such as to turn water into steam or to increase the temperature of steam contained within balloon 132 prior to their delivery through fluid delivery elements 145. Coils 144 can be used to expand one or more fluids contained within balloon 132 such as to propel the expanded fluid through balloon 132. Coils 144 can comprise a heating wire, such as a heatable nickel titanium alloy wire. Coils 144 can be positioned in various locations within device 100, such as a location selected from the group consisting of: in radially expandable element 130; on an inner and/or outer surface of radially expandable element 130; proximal to radially expandable element 130; proximal to shaft 110; proximate to at least one fluid delivery element 145; within at least one fluid delivery element 145; within shaft 110; and combinations of these.

Fluid delivery tube 141 can include one or more valves, such as valve 159 configured to regulate flow in one or both directions through fluid delivery tube 141. Valve 159 can be configured to maintain a minimum pressure in balloon 132, such as during delivery of ablative fluid through fluid delivery elements 145. Valve 159 can be configured to allow fluid extraction from balloon 132 when the pressure across valve 159 exceeds a threshold.

Fluid delivery elements 145 of FIG. 4 are configured to deliver one or more ablative fluid to target tissue, such as duodenal wall tissue, while minimizing trauma to non-target tissue, such as duodenal adventitial tissue, as has been described in detail in reference to FIG. 1 hereabove. Ablative fluid can be delivered in one or more sequential or simultaneous steps, as has been described in reference to FIG. 2 hereabove.

Figure 5:
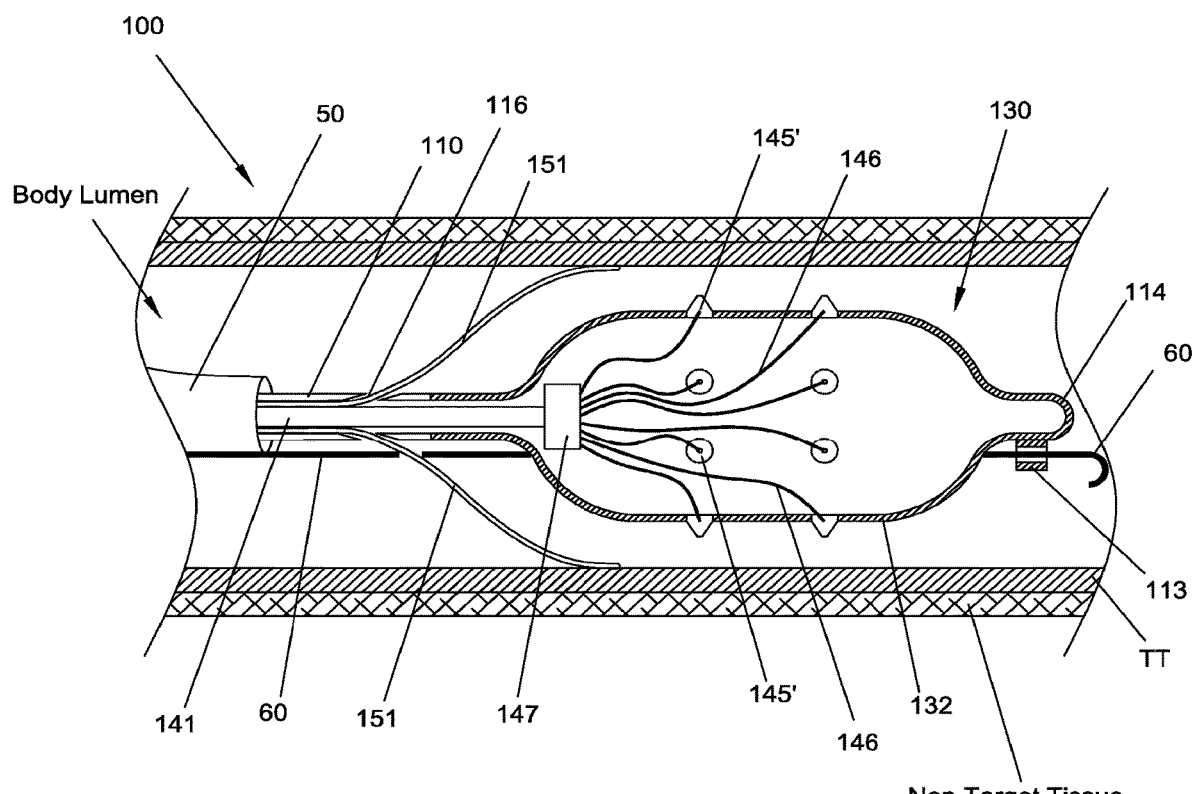
FIG. 5 is a side sectional view of the distal portion of an ablation device comprising a luminal positioning assembly, consistent with the present inventive concepts.

Referring now to FIG. 5, a side sectional view of the distal portion of an ablation device comprising a luminal positioning assembly is illustrated, consistent with the present inventive concepts. Ablation device 100 comprises shaft 110, a relatively flexible, biocompatible, elongate structure configured for insertion into a body lumen such as the duodenal lumen shown. Shaft 110 is typically connected to a handle on its proximal end, not shown but configured to allow an operator to advance, retract and otherwise manipulate or control ablation device 100. Ablation device 100 can be configured for delivery over a guidewire, via a lumen from a proximal portion to a distal portion, or via a rapid exchange sidecar in the distal portion of device 100 such as sidecar 113 shown having been advanced over guidewire 60. Device 100 can include or otherwise be inserted through a body introduction device, such as introducer 50 shown, typically an endoscope, sheath, or other body introduction device.

Device 100 includes an expandable assembly 130, positioned in a segment of tubular tissue including target tissue TT and non-target tissue. Target tissue TT can comprise mucosal tissue and at least a portion of submucosal tissue, such as submucosal tissue which has been expanded as described in reference to FIG. 1 hereabove. Expandable assembly 130 comprises an inflatable balloon 132 positioned on the distal end of shaft 110 as shown. The distal end of device 100 includes tip 114, attached to the distal end of balloon 132 and including a profile configured for atraumatic insertion and advancement of device 100 within a body lumen such as the gastrointestinal tract. Mounted on, in and/or within the walls of balloon 132 in a circumferential array of multiple nozzles 145', of similar or dissimilar construction and arrangement to each other. Nozzles 145' are positioned to deliver ablative fluid to a full or partial circumferential segment of tubular tissue, such as a full circumferential segment of the duodenum. Individual fluid delivery tubes 146 are connected on their distal end to each nozzle 145', and on their proximal end to manifold 147. Fluid delivery tube 141 is in fluid communication within manifold 147, such that ablative fluid delivered through fluid delivery tube 141, as has been described hereabove, passes through manifold 147 for delivery to the target tissue TT through the array of nozzles 145'. Balloon 132 is configured such that negative pressure applied through fluid delivery tube 141 causes balloon 132 to collapse.

Device 100 further includes a luminal positioning assembly comprising two or more radially deployable arms 151 which are configured to be advanced out of two or more aligned openings 116 in shaft 110. Arms 151 are configured such that when deployed, arms 151 cause shaft 110 and/or expandable assembly 130 to tend to be centered within the body lumen as shown. Arms 151 and/or a control rod attached thereto travel proximally through shaft 110, and operably attach to a control on a handle not shown but configured to advance and retract deployable arms 151.

Nozzles 145' of FIG. 5 are configured to deliver one or more ablative fluid to target tissue, such as duodenal wall tissue, while minimizing trauma to non-target tissue, such as duodenal adventitial tissue, as has been described in detail in reference to FIG. 1 hereabove. Ablative fluid can be delivered in one or more sequential or simultaneous steps, as has been described in reference to FIG. 2 hereabove.

Figure 6:
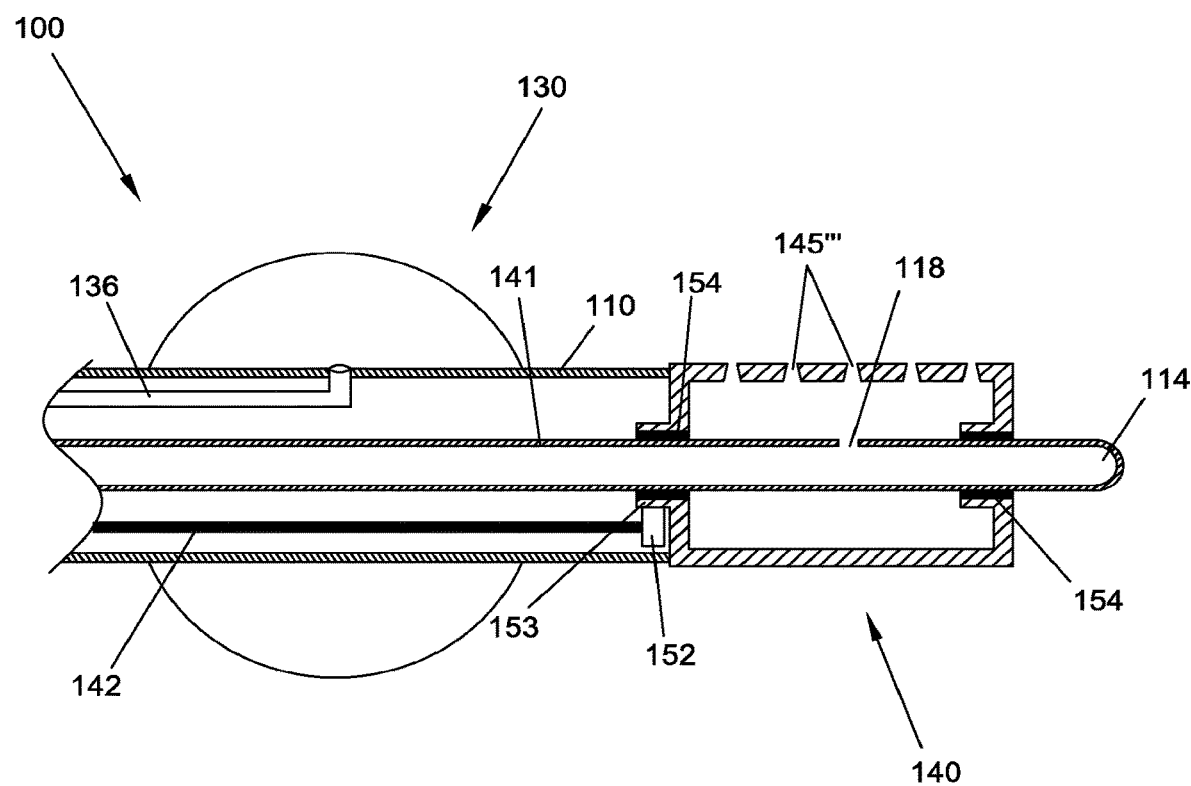
FIG. 6 is a side sectional view of the distal portion of an ablation device comprising a rotating fluid delivery assembly, consistent with the present inventive concepts.

Referring now to FIG. 6, a side sectional view of the distal portion of an ablation device comprising a rotating fluid delivery assembly is illustrated, consistent with the present inventive concepts. Ablation device 100 comprises shaft 110, a relatively flexible, biocompatible, elongate structure configured for insertion into a body lumen such as the duodenal lumen shown. Shaft 110 is typically connected to a handle on its proximal end, not shown but configured to allow an operator to advance, retract and otherwise manipulate or control ablation device 100. Ablation device 100 can be configured for delivery over a guidewire, via a lumen from a proximal portion to a distal portion, or via a rapid exchange sidecar as has been described herein. Device 100 can include or otherwise be inserted through a body introduction device such as an endoscope or introducer sheath.

Device 100 includes an expandable assembly 130, positioned on a distal portion of shaft 110. Expandable assembly 130 can comprise one or more various forms of expandable elements such as a balloon or expandable cage, such as a balloon in fluid communication with inflation tube 136 as shown. Expandable assembly 130 is configured to cause the distal portion of shaft 110 to tend to be centered within a body lumen. The distal end of device 100 includes tip 114, attached to the distal end of shaft 110 and including a profile configured for atraumatic insertion and advancement of device 100 within a body lumen such as the gastrointestinal tract.

Device 100 further includes fluid delivery assembly 140 attached to shaft 110 distal to expandable assembly 130. In some embodiments, expandable assembly 130 is distal to fluid delivery assembly 140. In other embodiments, device 100 includes a second radially expandable assembly wherein fluid delivery assembly 140 is positioned between two radially expandable assemblies, such as to allow an operator to cause fluid delivery assembly 140 to be relatively centered in a body lumen as has been described hereabove. Fluid delivery assembly 140 includes multiple fluid delivery elements, slits 145''', shown positioned along a linear segment of fluid delivery assembly 140 but alternatively positioned in one or more various geometric arrangements. Fluid delivery assembly 140 is fluidly attached to fluid delivery tube 141, such that ablative or other fluids passing through fluid delivery tube 141 pass through opening 118 into fluid delivery assembly 140. In some embodiments, slits 145''' can be sized to accelerate one or more ablative fluids passing therethrough. In some embodiments, fluid delivery assembly 140 comprises a sufficiently flexible material such that slits 145''' widen as pressure within fluid delivery assembly 140 increases.

Fluid delivery assembly 140 is configured to be rotated, such as via a motion transfer mechanism such as motion transfer assembly 320 of system 10 of FIG. 1. In the embodiment of FIG. 6, ablation device 100 includes a drive shaft 142 which includes drive gear 152 at its distal end. Draft shaft 142 travels proximally through shaft 110 to a connection port on a handle, not shown but configured to attach to a rotatable drive. Fluid delivery assembly 140 includes gear 153 which operably mates or otherwise engages gear 152, such that rotation of drive shaft 142 causes fluid delivery assembly 140 to rotate. Fluid delivery assembly 140 comprises one or more O-rings 154, such as those shown positioned to create a fluid seal between fluid delivery tube 141 and fluid delivery assembly 140. In use, ablative fluid is delivered from fluid delivery tube 141, through opening 118, to fluid delivery assembly 140. Fluid can be delivered prior to, during and/or after rotation of fluid delivery assembly 140 by drive shaft 142. Rotation of fluid delivery assembly 140 causes a full circumferential delivery of ablative fluid through slits 145''' to target tissue positioned proximate slits 145'''.

Rotation of fluid delivery assembly 140 can be accomplished manually and/or automatically. Rotation of fluid delivery assembly 140 can be accomplished by an operator and/or by a motion controlling device such as motion transfer assembly 320 of FIG. 1 when the motion transfer assembly is operably attached to drive shaft 142. Rotation of fluid delivery assembly 140 can be performed based on a signal received from one or more sensors (e.g. one or more sensors as described in reference to FIG. 1 hereabove). Alternatively or additionally, rotation of fluid delivery assembly 140 can be performed based on the analysis and/or processing of one or more images, such as one or more images produced by ablation device 100 and/or another imaging device (e.g. imaging device 410 of FIG. 1). Rotation of fluid delivery assembly 140 can be performed prior to, during and/or after delivery of ablative fluid from fluid delivery element 145''' to target tissue.

Slits 145''' of FIG. 6 are configured to deliver one or more ablative fluid to target tissue, such as duodenal wall tissue, while minimizing trauma to non-target tissue, such as duodenal adventitial tissue, as has been described in detail in reference to FIG. 1 hereabove. Ablative fluid can be delivered in one or more sequential or simultaneous steps, as has been described in reference to FIG. 2 hereabove.

Figure 7:
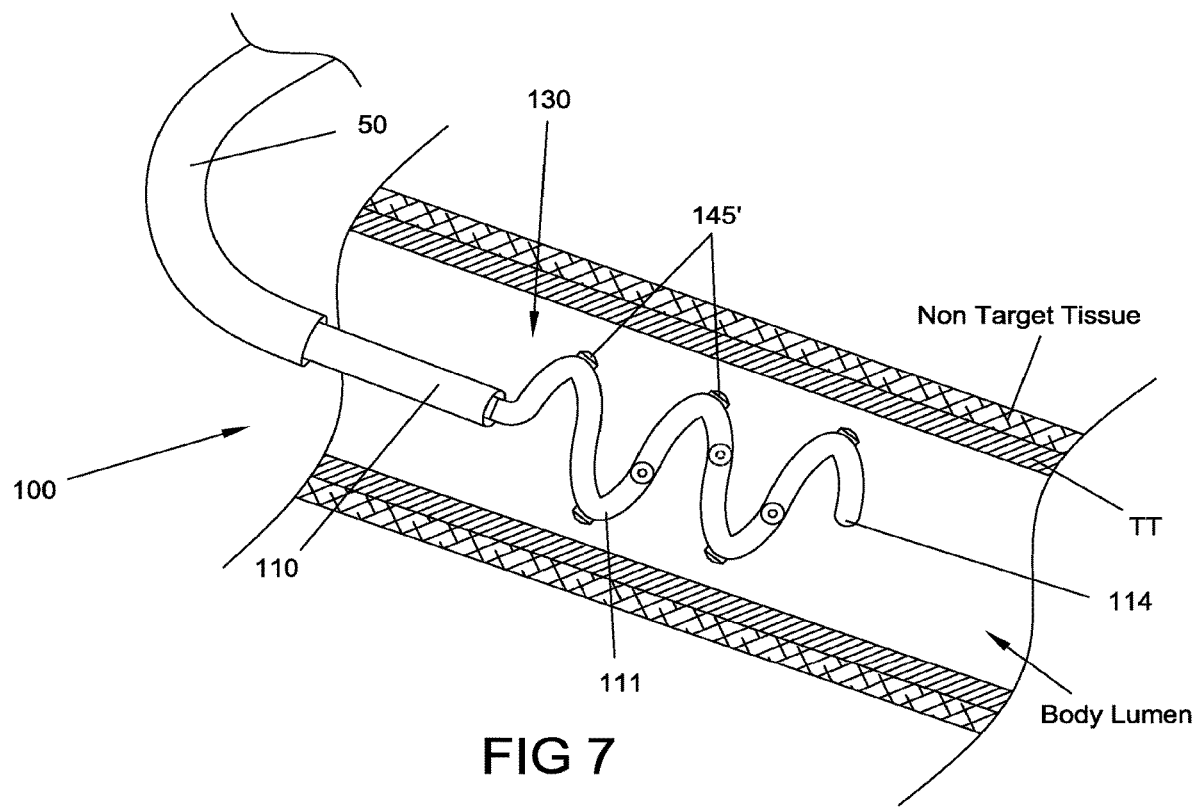
FIGS. 7 and 7A are side sectional views of the distal portion of an ablation device comprising a helical array of fluid delivery elements, consistent with the present inventive concepts.

Referring now to FIG. 7, a side sectional view of the distal portion of an ablation device comprising a helical array of fluid delivery elements is illustrated, consistent with the present inventive concepts. Ablation device 100 comprises shaft 110, a relatively flexible, biocompatible, elongate structure configured for insertion into a body lumen such as the duodenal lumen shown. Shaft 110 is typically connected to a handle on its proximal end, not shown but configured to allow an operator to advance, retract and otherwise manipulate or control ablation device 100. Ablation device 100 can be configured for delivery over a guidewire, via a lumen from a proximal portion to a distal portion, or via a rapid exchange sidecar in the distal portion of the device as has been described hereabove. Device 100 can include or otherwise be inserted through a body introduction device, such as introducer 50 shown, typically an endoscope, sheath, or other body introduction device.

Device 100 includes an expandable assembly 130, positioned in a segment of tubular tissue including target tissue TT and non-target tissue. Target tissue TT can comprise mucosal tissue and at least a portion of submucosal tissue, such as submucosal tissue which has been expanded as described in reference to FIG. 1 hereabove. Expandable assembly 130 comprises a resiliently biased helical coil, shaft 111, such as a flexible plastic shaft surrounding a helical mandrel, mandrel not shown but typically a stainless steel or nickel titanium alloy mandrel elastically biased in a helical configuration. Shaft 111 is configured to be radially compressible such as via retraction into shaft 110 and/or introducer 50.

The distal end of shaft 111 includes tip 114, including a profile configured for atraumatic insertion and advancement of device 100 within a body lumen such as the gastrointestinal tract. Positioned along shaft 111 are multiple nozzles 145', such as multiple nozzles positioned to deliver ablative fluid to a full or partial circumference of an axial segment of tubular tissue, such as a segment of duodenal mucosa as shown in FIG. 7. The multiple nozzles 145' are fluidly attached to one or more sources of ablative fluid, such as ADU 330 of FIG. 1.

Figure 7A:
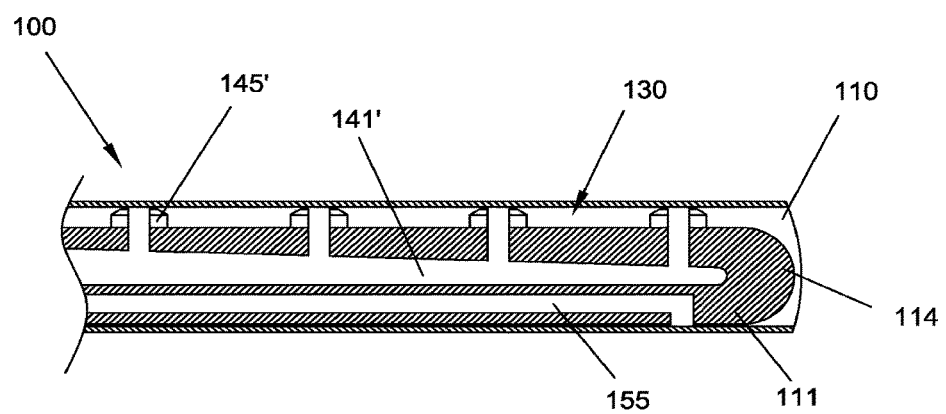

Referring now to FIG. 7A, a sectional view of device 100 of FIG. 7 is shown. Shaft 111 has been retracted into shaft 110 (e.g. via a lever or other control on a handle on the proximal end of shaft 110) such that shaft 111 has been radially compressed as shown. Shaft 111 includes fluid delivery tube 141' which is fluidly attached to the multiple nozzles 145'. Fluid delivery tube 141' comprises a non-uniform diameter, such as a diameter which reduces as it travels distally along shaft 111. The decreasing diameter can be configured to cause equal pressure distribution of ablative fluid delivered from tube 141' to the various nozzles 145'. Shaft 111 further comprises a fluid extraction element, drain 155, which can be used to remove fluids from a body lumen, such as ablative fluids delivered by nozzles 145' to a body lumen. Drain 155 travels proximally, through shaft 111 and shaft 110, such as to connect to an extraction port, not shown but typically positioned on a proximal handle. In some embodiments, the fluid removed through drain 155 is recirculated, such as for delivery through nozzles 145'. In some embodiments, drain 155 is configured to remove fluid from one or more portions of device 100. In some embodiments, one or more nozzles 145' are configured to remove fluid from a body lumen.

Nozzles 145' of FIGS. 7 and 7A are configured to deliver one or more ablative fluid to target tissue, such as duodenal wall tissue, while minimizing trauma to non-target tissue, such as duodenal adventitial tissue, as has been described in detail in reference to FIG. 1 hereabove. Ablative fluid can be delivered in one or more sequential or simultaneous steps, as has been described in reference to FIG. 2 hereabove.

Referring now to FIGS. 8A-C, side sectional views of the distal portion of an ablation device comprising a rotatable fluid delivery element are illustrated, consistent with the present inventive concepts. Ablation device 100 comprises shaft 110, a relatively flexible, biocompatible, elongate structure configured for insertion into a body lumen such as the duodenal lumen shown. Shaft 110 is typically connected to a handle on its proximal end, not shown but configured to allow an operator to advance, retract and otherwise manipulate or control ablation device 100. Ablation device 100 can be configured for delivery over a guidewire, via a lumen from a proximal portion to a distal portion, or via a rapid exchange sidecar as has been described herein. The distal end of device 100 includes tip 114, attached to the distal end of shaft 110 and including a profile configured for atraumatic insertion and advancement of device 100 within a body lumen such as the gastrointestinal tract. Device 100 can include or otherwise be inserted through a body introduction device such as an endoscope or introducer sheath.

Device 100 includes a fluid delivery element 145, such as a nozzle or other fluid delivery element as has been described hereabove. Fluid delivery element 145 is fluidly attached to fluid delivery tube 141, which travels proximally through shaft 110 to be attachable to a source of ablative fluid, such as via a fluid connection on a proximal handle, as has been described in detail hereabove. Fluid delivery element 145 is attached to rotating member 158 which is rotatably attached to a portion of shaft 110 via pin 157. Control rod 156 is attached to rotating member 158 such that advancement and retraction of rod 156 causes rotating member 158 and fluid delivery element 145 to rotate. Control rod 156 travels proximally through shaft 110 and is attached to a lever or other control, not shown but a control attached to a proximal handle as has been described hereabove.

Referring now to FIGS. 8B and 8C, side sectional views of the distal portion of ablation device 100 of FIG. 8A are shown. In FIG. 8B, control rod 156 has been retracted (e.g. by a control on a proximal handle) to cause rotating member 158 and fluid delivery element 145 to rotate clockwise as shown. In FIG. 8C, control rod 156 has been advanced to cause rotating member 158 and fluid delivery element 145 to rotate counterclockwise as shown.

Rotation of fluid delivery element 145 can be accomplished manually and/or automatically. Rotation of fluid delivery element 145 can be accomplished by an operator and/or by a motion controlling device such as motion transfer assembly 320 of FIG. 1 when the motion transfer assembly is operably attached to control rod 156. Rotation of fluid delivery element 145 can be performed based on a signal received from one or more sensors (e.g. one or more sensors as described in reference to FIG. 1 hereabove). Alternatively or additionally, rotation of fluid delivery element 145 can be performed based on the analysis and/or processing of one or more images, such as one or more images produced by ablation device 100 and/or another imaging device (e.g. imaging device 410 of FIG. 1), Rotation of fluid delivery element 145 can be performed prior to, during and/or after delivery of ablative fluid from fluid delivery element 145 to target tissue.

In alternative embodiments, rotating member 158 inserted within a ball joint, not including pin 157, such that two degree of freedom of fluid delivery element 145 can be achieved, such as via one or more control rods 156 which attach to one or more controls on a proximal handle.

Fluid delivery element 145 of FIGS. 8A-C is configured to deliver one or more ablative fluid to target tissue, such as duodenal wall tissue, while minimizing trauma to non-target tissue, such as duodenal adventitial tissue, as has been described in detail in reference to FIG. 1 hereabove. Ablative fluid can be delivered in one or more sequential or simultaneous steps, as has been described in reference to FIG. 2 hereabove.

Referring now to FIG. 9, a side view of the distal portion of an ablation device comprising multiple expandable assemblies is illustrated, consistent with the present inventive concepts. Ablation device 100 comprises shaft 110, a relatively flexible, biocompatible, elongate structure configured for insertion into a body lumen such as the duodenal lumen shown. Shaft 110 is typically connected to a handle on its proximal end, not shown but configured to allow an operator to advance, retract and otherwise manipulate or control ablation device 100. Ablation device 100 can be configured for delivery over a guidewire, via a lumen from a proximal portion to a distal portion, or via a rapid exchange sidecar in the distal portion of the device as has been described hereabove. Device 100 can include or otherwise be inserted through a body introduction device, such as introducer 50 shown, typically an endoscope, sheath, or other body introduction device.

Device 100 includes fluid delivery assembly 140, positioned between a first expandable assembly 130a and a second expandable assembly 130b. Expandable assemblies 130a and 130b can comprise one or more expandable elements such as a balloon, cage or other expandable element as has been described herein. Fluid delivery assembly 140 of FIG. 9 comprises a tube-shaped, inflatable balloon 134 which is fluidly attached to a fluid delivery tube, not shown but traveling proximally to be attached to a fluid delivery device such as ADU 330 of FIG. 1. Balloon 134 can comprise a non-compliant balloon.

Device 100 includes shaft 111a which is slidingly received by shaft 110. Device 100 further includes shaft 111b which is slidingly received by shaft 111a. The distal end of device 100 includes tip 114, attached to the distal end of shaft 111b and including a profile configured for atraumatic insertion and advancement of device 100 within a body lumen such as the gastrointestinal tract. Expandable assembly 130b is attached to a distal portion of shaft 111b. Balloon 134 of fluid delivery assembly 140 is attached to the distal end of shaft 111a. Expandable assembly 130a is attached to the distal end of shaft 110.

Fluid delivery assembly 140 comprises one or more elongate openings, slits 145''' around at least a portion of the circumference of balloon 134. Balloon 134 thickness and slits 145''' dimensions are configured such that as fluid is delivered into balloon 134, balloon 134 expands to a first diameter while slits 145''' maintain a relatively tight fluid seal.

Independent or combined movement of shafts 110, 111a and/or 111b can be used to manipulate tissue, such as to linearize or distend tubular tissue, such as when balloon 134 and/or expandable assemblies 130a and/or 130b is radially expanded to contact tissue. Balloon 134 and/or expandable assemblies 130a and/or 130b can be expanded to occlude a body lumen, such as to occlude the proximal and distal end of a segment of gastrointestinal tissue.

In some embodiments, fluid delivery assembly 140 and expandable assemblies 130a and 130b comprise a single component, such as a dog-bone shaped balloon. In some embodiments, expandable assembly 130a and/or 130b comprise a balloon with one or more fluid delivery elements, such as slits 145'''' as shown. In these embodiments, expandable assemblies 130a and/or 130b can receive fluid from the same fluid delivery tube as balloon 134 and/or a different fluid delivery tube, such as to deliver the same or different ablative fluids through slits 145''''.

Referring now to FIG. 9A, fluid has been introduced into balloon 134 such that balloon 134 is fully expanded and slits 145''' have expanded to allow ablative fluid to exit therethrough (dispersion of ablative fluid not shown).

Slits 145''' of FIGS. 9 and 9A are configured to deliver one or more ablative fluids to target tissue, such as duodenal wall tissue, while minimizing trauma to non-target tissue, such as duodenal adventitial tissue, as has been described in detail in reference to FIG. 1 hereabove. Ablative fluid can be delivered in one or more sequential or simultaneous steps, as has been described in reference to FIG. 2 hereabove. Fluid delivery elements 145'''' of FIGS. 9 and 9A can also be configured to deliver ablative fluids to target tissue.

Figure 10:
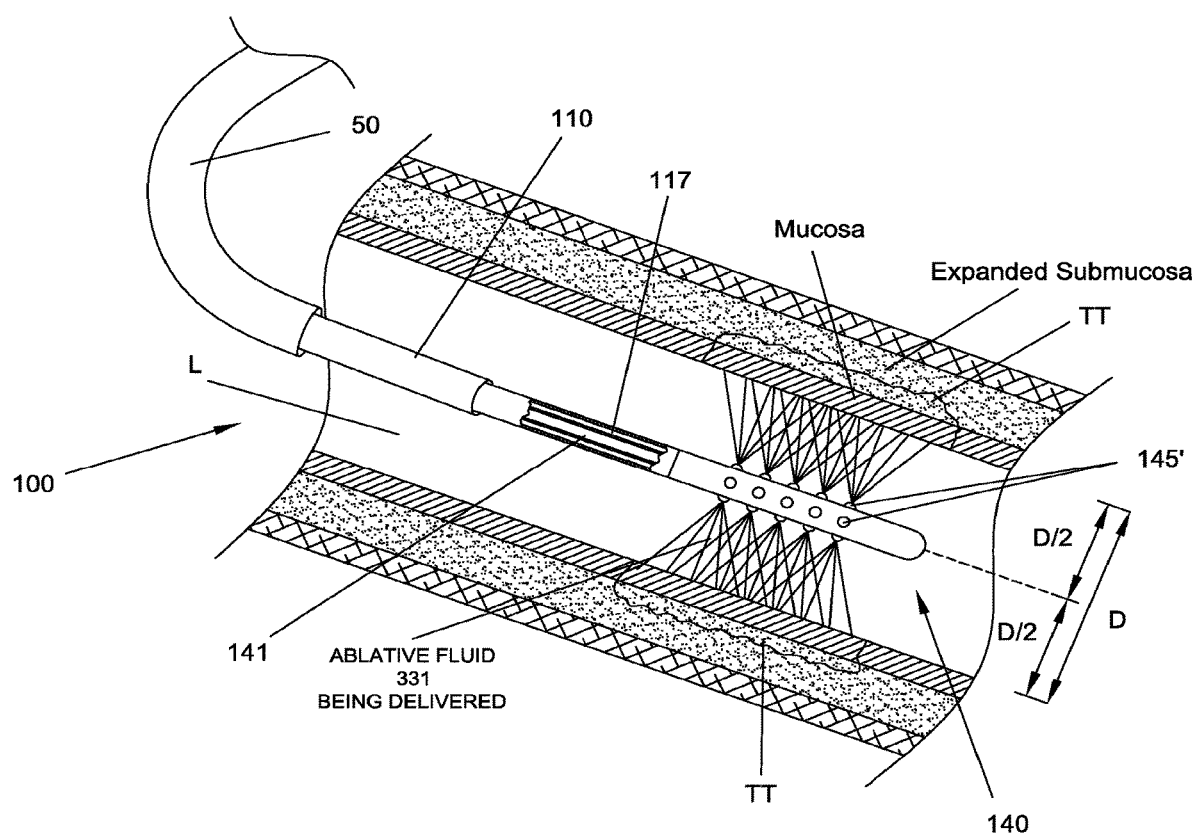
FIG. 10 is a side sectional view of the distal portion of an ablation device comprising a circumferential array of fluid delivery elements, consistent with the present inventive concepts.

Referring now to FIG. 10, a side sectional view of the distal portion of an ablation device comprising a circumferential array of fluid delivery elements is illustrated, consistent with the present inventive concepts. Ablation device 100 comprises shaft 110, a relatively flexible, biocompatible, elongate structure configured for insertion into a body lumen such as the duodenal lumen shown. Shaft 110 is typically connected to a handle on its proximal end, not shown but configured to allow an operator to advance, retract and otherwise manipulate or control ablation device 100. Ablation device 100 can be configured for delivery over a guidewire, via a lumen from a proximal portion to a distal portion, or via a rapid exchange sidecar in the distal portion of the device as has been described hereabove. Device 100 can include or otherwise be inserted through a body introduction device, such as introducer 50 shown, typically an endoscope, sheath, or other body introduction device.

Device 100 includes fluid delivery assembly 140 comprising multiple fluid delivery elements, nozzles 145'. Fluid delivery assembly 140 has been axially positioned within a body lumen L to treat target tissue TT. Target tissue TT comprises a full circumferential portion of mucosal tissue, as well as a partial depth of submucosal tissue. The submucosal tissue has been expanded, such as by using tissue expansion device 200 as described in reference to FIG. 1 hereabove. Device 100 is configured to prevent damage to tissue layers deeper than the expanded submucosal layer, such as to avoid damaging the adventitia.

Nozzles 145' are fluidly connected to fluid delivery tube 141, which extends proximally to a fluid attachment port, not shown but mounted to a proximal handle for attachment to an agent delivery assembly as has been described hereabove. The multiple nozzles 145' are positioned to deliver ablative fluid 331 to a full or partial circumference of an axial segment of tubular tissue as has been described hereabove. A lumen 117 can be positioned to surround fluid delivery tube 141. One or more fluids can be introduced into and/or through lumen 117, such as a recirculating fluid delivered by a fluid delivery device attached to the proximal end of device 100 as is described herein. Fluids introduced into and/or through lumen 117 can be used to pre-heat fluid delivery tube 141, warm fluid delivery tube 141, cool fluid delivery tube 141 and/or insulate fluid delivery tube 141.

Device 100 and nozzles 145' are configured such that one or more reactive forces result as ablative fluid 331 is delivered through at least one nozzle 145', such as the reactive forces generated by nozzles included in hovercraft devices. In some embodiments, the one or more reactive forces can be used to position at least one nozzle 145' at a fixed or minimum distance from a tissue surface. In other embodiments, multiple reactive forces are used to position fluid delivery assembly 140 in a relative center of a body lumen, such as the relative center of body lumen L (e.g. the axis of shaft 110 is relatively positioned at half the diameter D of lumen L as shown). Rate of fluid delivery can be varied through at least one nozzle 145' to cause any nozzle 145' to move.

Nozzles 145' of FIG. 10 are configured to deliver one or more ablative fluids to target tissue TT, such as duodenal wall tissue, while minimizing trauma to non-target tissue, such as duodenal adventitial tissue, as has been described in detail in reference to FIG. 1 hereabove. Ablative fluid 331 can be delivered in one or more sequential or simultaneous steps, as has been described in reference to FIG. 2 hereabove.

Figure 11:
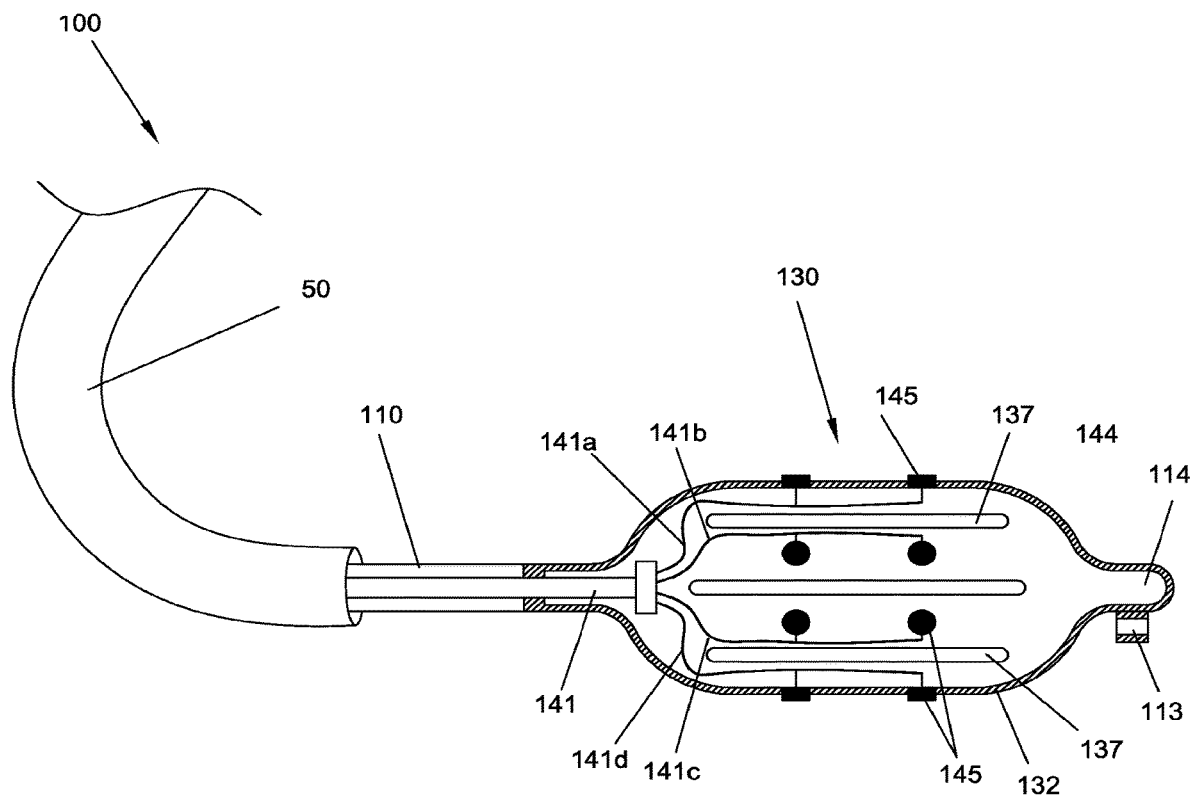
FIGS. 11 and 11A are side and end views, respectively, of the distal portion of an ablation device comprising an expandable assembly with centering members, consistent with the present inventive concepts.
Figure 11A:
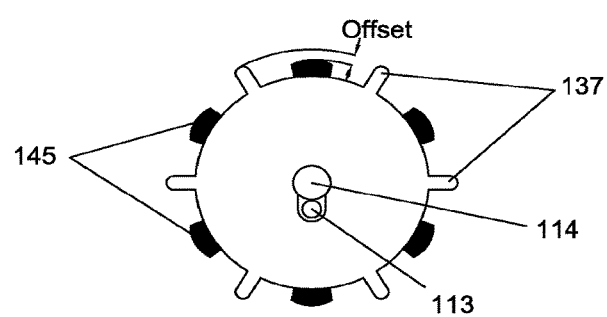

Referring now to FIGS. 11 and 11A, side and end views of the distal portion of an ablation device comprising an expandable assembly with centering members are illustrated, consistent with the present inventive concepts. Ablation device 100 comprises shaft 110, a relatively flexible, biocompatible, elongate structure configured for insertion into a body lumen. Shaft 110 is typically connected to a handle on its proximal end, not shown but configured to allow an operator to advance, retract and otherwise manipulate or control ablation device 100. Ablation device 100 can be configured for delivery over a guidewire, via a lumen from a proximal portion to a distal portion, or via a rapid exchange sidecar in the distal portion of device 100 such as sidecar 113 shown. Device 100 can include or otherwise be inserted through a body introduction device, such as introducer 50 shown, typically an endoscope, sheath, or other body introduction device.

Device 100 includes expandable assembly 130, typically comprising balloon 132, or other expandable element such as an expandable cage as has been described hereabove. Balloon 132 can comprise a compliant or non-compliant balloon. The distal end of device 100 includes tip 114, attached to the distal end of balloon 132 and including a profile configured for atraumatic insertion and advancement of device 100 within a body lumen such as the gastrointestinal tract.

Mounted in, on, and/or within balloon 132 are multiple fluid delivery elements 145, typically each comprising a nozzle oriented radially out from the surface of balloon 132 when expanded. Fluid delivery elements 145 can be arranged in one or more patterns, such as a full or partial circumferential pattern of nozzles as has been described hereabove.

A fluid delivery tube 141 fluidly connects to multiple delivery tubes 141*a-d* which fluidly connect to the multiple fluid delivery elements 145 in one or more patterns such as the pattern shown in FIG. 11. Fluid delivery tube 141 travels proximally through shaft 110 and is configured to fluidly attach to a fluid delivery device such as ADU 330 of FIG. 1.

Device 100 further includes multiple centering elements, longitudinal ridges 137 which are positioned on the external surface of balloon 132. In some embodiments, at least 4, or at least 8 ridges 137 are included on the surface of balloon 132, such as equidistantly spaced ridges positioned along the 360° circumference of balloon 132 (e.g. 4 ridges spaced 90° apart, 6 ridges spaced 60° apart or 8 ridges spaced 45° apart). In some embodiments, fluid delivery elements 145 are relatively equidistantly spaced along the length and/or circumference of balloon 132, such as at a distance less than 5 mm apart, less than 2 mm apart, or less than 1 mm apart. Ridges 137 comprise a height of at least 250 microns, or at least 500 microns. Alternatively, ridges 137 can be offset from a top surface of fluid delivery elements 145 by a distance of 250 microns, or 500 microns. In some embodiments, ridges 137 can be formed by pinching and bonding folds in balloon 132. Alternatively or additionally, ridges 137 can be formed by bonding filamentous material to balloon 132, such as tubes or strips of polyethylene terephthalate (PET) or nylon.

Fluid delivery elements 145 of FIGS. 11 and 11A are configured to deliver one or more ablative fluids to target tissue, such as duodenal wall tissue, while minimizing trauma to non-target tissue, such as duodenal adventitial tissue, as has been described in detail in reference to FIG. 1 hereabove. Ablative fluid can be delivered in one or more sequential or simultaneous steps, as has been described in reference to FIG. 2 hereabove.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A method of ablating mucosal tissue in a patient's duodenum, the method comprising:
introducing an ablation device into the patient's gastrointestinal (GI) tract, the ablation device comprising:
an elongate shaft;
a proximal radially expandable element attached to the elongate shaft and having a proximal radially expandable element contracted state and a proximal radially expandable element expanded state;
a distal radially expandable element attached to the elongate shaft and having a distal radially expandable element contracted state and a distal radially expandable element expanded state;
identifying an ampulla of Vater in the patient's GI tract;
advancing the ablation device to a first location in the patient's duodenum distal to the ampulla of Vater with the proximal radially expandable element in the proximal radially expandable element contracted state and with the distal radially expandable element in the distal radially expandable element contracted state;
at the first location in the patient's duodenum distal to the ampulla of Vater:
moving the proximal radially expandable element to the proximal radially expandable element expanded state and the distal radially expandable element to the distal radially expandable element expanded state such that each radially expandable element directly contacts a respective circumferential ring of mucosal tissue of a GI wall of the first location and together define a first treatment region of mucosal tissue therebetween; and
causing a first delivery of ablative fluid via a fluid delivery element positioned on the elongate shaft between the proximal and distal radially expandable elements, the ablative fluid directly contacting the mucosal tissue of the first treatment region;
after the first delivery of ablative fluid, moving the ablation device to a second location in the patient's duodenum distal to the ampulla of Vater; and
at the second location in the patient's duodenum distal to the ampulla of Vater:
the proximal and distal radially expandable elements in their respective expanded states together define a second treatment region of mucosal tissue therebetween; and
causing a second delivery of ablative fluid, the ablative fluid directly contacting the mucosal tissue of the second treatment region via the fluid delivery element;
wherein the ablative fluid ablates contacted duodenal mucosal tissue while avoiding damaging duodenal adventitial tissue, and
wherein the method comprises treating at least 50% of an axial length of the patient's duodenum distal to the patient's ampulla of Vater by causing delivery of ablative fluid to additional locations after the first and second locations,
wherein the first location, the second location, and the additional locations are confined to the duodenum.

2. The method of claim 1, further comprising, after the first delivery of ablative fluid, moving the proximal and distal radially expandable elements to their respective contracted states and then, at the second location, moving the proximal and distal radially expandable elements to their respective expanded states before the second delivery of ablative fluid.

3. The method of claim 1, wherein at least one of the proximal and the distal radially expandable elements is configured to seal a portion of the GI tract in their respective expanded state.

4. The method of claim 3, wherein the proximal and distal radially expandable elements in their respective expanded states form an enclosed volume in the GI tract.

5. The method of claim 1, wherein the ablative fluid comprises steam.

6. The method of claim 1, wherein introducing the ablation device into the patient's GI tract comprises passing the ablation device through a working channel of an endoscope.

7. The method of claim 6, wherein advancing the ablation device to the first location in the patient's duodenum comprises distally extending the ablation device beyond a distal end of the working channel of the endoscope.

8. The method of claim 1, wherein at least one of the proximal and the distal radially expandable elements comprises a radially expandable material resiliently biased in the respective expanded state.

9. The method of claim 1, wherein the first location and the second location are adjacent or partially overlapping.

10. The method of claim 1, wherein all of the additional locations are distal the ampulla of Vater.

11. The method of claim 1, further comprising selecting the first location, the second location, and the additional locations to protect the ampulla of Vater.

12. A method of ablating mucosal tissue in a patient's duodenum, the method comprising:
introducing an ablation device into the patient's gastrointestinal (GI) tract, the ablation device comprising:
an elongate shaft;
a proximal radially expandable element attached to the elongate shaft and having a proximal radially expandable element contracted state and a proximal radially expandable element expanded state;
a distal radially expandable element attached to the elongate shaft and having a distal radially expandable element contracted state and a distal radially expandable element expanded state;
identifying an ampulla of Vater in the patient;
based on identifying the ampulla of Vater in the patient, selecting a plurality of treatment locations in the duodenum at which to treat the mucosal tissue with the ablation device while avoiding damage to the patient's ampulla of Vater, the plurality of treatment locations being confined to the patient's duodenum,
advancing the ablation device to a first location of the plurality of treatment locations in the patient's duodenum with the proximal radially expandable element in the proximal radially expandable element contracted state and with the distal radially expandable element in the distal radially expandable element contracted state;
at the first location in the patient's duodenum:
moving the proximal radially expandable element to the proximal radially expandable element expanded state and the distal radially expandable element to the distal radially expandable element expanded state such that each radially expandable element directly contacts a respective circumferential ring of mucosal tissue of a GI wall of the first location and together define a first treatment region of mucosal tissue therebetween; and
causing a first delivery of ablative fluid via a fluid delivery element positioned on the elongate shaft between the proximal and distal radially expandable elements, the ablative fluid directly contacting the mucosal tissue of the first treatment region;

after the first delivery of ablative fluid, moving the ablation device to a second location of the plurality of treatment locations in the patient's duodenum; and at the second location in the patient's duodenum:

the proximal and distal radially expandable elements in their respective expanded states together define a second treatment region of mucosal tissue therebetween; and causing a second delivery of ablative fluid, the ablative fluid directly contacting the mucosal tissue of the second treatment region via the fluid delivery element;

wherein the ablative fluid ablates contacted duodenal mucosal tissue while avoiding damaging duodenal adventitial tissue.

13. The method of claim 12, further comprising, after the first delivery of ablative fluid, moving the proximal radially expandable element to the proximal radially expandable element contract state and the distal radially expandable element to the distal radially expandable element contracted state and then, at the second location, moving the proximal radially expandable element to the proximal radially expandable element expanded state and the distal radially expandable element to distal radially expandable element expanded state before the second delivery of ablative fluid.

14. The method of claim 12, wherein at least one of the proximal radially expandable element in the proximal radially expandable element expanded state and the distal radially expandable element in the distal radially expandable element expanded state is configured to seal a portion of the patient's GI tract.

15. The method of claim 14, wherein in combination the proximal radially expandable element in the proximal radially expandable element expanded state and the distal radially expandable element in the distal radially expandable element expanded state form an enclosed volume in the patient's GI tract.

16. The method of claim 12, wherein the ablative fluid comprises steam.

17. The method of claim 12, wherein introducing the ablation device into the patient's GI tract comprises passing the ablation device through a working channel of an endoscope.

18. The method of claim 17, wherein advancing the ablation device to the first location in the patient's duodenum comprises distally extending the ablation device beyond a distal end of the working channel of the endoscope.

19. The method of claim 12, wherein at least one of the proximal radially expandable element and the distal radially expandable element comprises a radially expandable material resiliently biased in the respective expanded state.

20. The method of claim 12, wherein the method comprises treating at least 50% of an axial length of the patient's duodenum.

* * * * *